US007057012B1

(12) United States Patent
Gardella et al.

(10) Patent No.: US 7,057,012 B1
(45) Date of Patent: Jun. 6, 2006

(54) PTH FUNCTIONAL DOMAIN CONJUGATE PEPTIDES, DERIVATIVES THEREOF AND NOVEL TETHERED LIGAND-RECEPTOR MOLECULES

(75) Inventors: Thomas J. Gardella, Needham, MA (US); Henry M. Kronenberg, Belmont, MA (US); John T. Potts, Jr., Newton, MA (US); Harald Jüppner, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/475,158

(22) Filed: Dec. 30, 1999

Related U.S. Application Data

(60) Provisional application No. 60/114,577, filed on Dec. 31, 1998.

(51) Int. Cl.
C07K 14/635 (2006.01)
A61K 38/29 (2006.01)

(52) U.S. Cl. .................................... 530/324; 514/12
(58) Field of Classification Search ............... 530/399, 530/300
See application file for complete search history.

(56) References Cited

U.S. PATENT DOCUMENTS

| 4,675,189 A | 6/1987 | Kent et al. .................. 424/490 |
| 4,698,328 A | 10/1987 | Neer et al. ..................... 514/12 |
| 4,736,866 A | 4/1988 | Leder et al. .................... 800/1 |
| 4,761,406 A | 8/1988 | Flora et al. ................... 514/86 |
| 5,527,772 A | 6/1996 | Holick .......................... 514/12 |
| 5,840,690 A | 11/1998 | Holick .......................... 514/12 |
| 5,977,070 A | 11/1999 | Piazza et al. .................. 514/12 |

OTHER PUBLICATIONS

Abou-Samra, A.-B., et al., "Non-Homologous Sequences of Parathyroid Hormone and the Parathyroid Hormone Related Peptide Bind to a Common Receptor on ROS 17/2.8 Cells," *Endocrinol.* 125:2215-2217 (1989).

Azarani, A., et al., "Structurally Diverse N-terminal Peptides of Parathyroid Hormone (PTH) and PTH-related Peptide (PTHRP) Inhibit the Na+/H+ Exchanger NHE3 Isoform by Binding to the PTH/PTHRP Receptor Type I and Activating Distinct Signaling Pathways," *J. Biol. Chem.* 271:14931-14936 (1996).

Bergwitz, C., et al., "Full Activation of Chimeric Receptors by Hybrids between Parathyroid Hormone and Calcitonin," *J. Biol. Chem.* 271:26469-26472 (1996).

Bergwitz, C., et al., "Residues in the Membrane-spanning and Extracellular Loop Regions of the Parathyroid Hormone (PTH)-2 Receptor Determine Signaling Selectivity for PTH and PTH-related Peptide," *J. Biol. Chem.* 272:28861-28868 (Nov. 1997).

Bisello, A., et al., "Parathyroid Hormone-Receptor Interactions Identified Directly by Photocross-linking and Molecular Modeling Studies," *J. Biol. Chem.* 273:22498-22505 (Aug. 1998).

Broadus, A.E. and Stewart, A.F., "Parathyroid Hormone-Related Protein Structure, Processing, and Physiological Actions," in *The Parathyroids Basic and Clinical Concepts*, Bilezikian et al., eds., Raven Press Ltd., New York, New York (1994).

Caulfield, M.P., et al., "The Bovine Renal Parathyroid Hormone (PTH) Receptor Has Equal Affinity for Two Different Amino Acid Sequences: The Receptor Binding Domains of PTH and PTH-Related Protein Are Located within the 14-34 Region," *Endocrinol.* 127:83-87 (1990).

Cleland, J.L., et al., "The Development of Stable Protein Formulations: A Close Look at Protein Aggregation, Deamidation, and Oxidation," *Critical Rev. Ther. Drug. Carrier Sys.* 10:307-377 (1993).

Cohen, F.E., et al., "Analogues of Parathyroid Hormone Modified at Positions 3 and 6. Effects on Receptor Binding and Activation of Adenylyl Cyclase in Kidney and Bone," *J. Biol. Chem.* 266:1997-2004 (1991).

Colquhoun, D., Binding, gating, affinity, and efficacy: The interpretation of structure-activity relationships for agonists and of the effects of mutating receptors, *Br. J. Pharmacol.* 125:924-947 (Nov. 1998).

Dautzenberg, F.M., et al., "Mapping of the ligand-selective domain of the *Xenopus laevis* corticotropin-releasing factor receptor 1: Implications for the ligand-binding site," *Proc. Natl. Acad. Sci. USA* 95:4941-4946 (Apr. 1998).

Dempster, D.W., et al., "Anabolic Actions of Parathyroid Hormone on Bone," *Endocrine Rev.* 14:690-709 (1993).

Dempster, D.W., et al., "Anabolic Actions of Parathyroid Hormone on Bone (Erratum)," *Endocrine Rev.* 15:261 (1994).

Gardella, T.J., et al., "Mutational Analysis of the Receptor-activating Region of Human Parathyroid Hormone," *J. Biol. Chem.* 266:13141-13146 (1991).

Gardella, T.J., et al., "Analysis of Parathyroid Hormone's Principal Receptor-Binding Region by Site-Directed Mutagenesis and Analog Design," *Endocrinol.* 132:2024-2030 (1993).

(Continued)

*Primary Examiner*—Ruixiang Li
(74) *Attorney, Agent, or Firm*—Sterne, Kessler, Goldstein & Fox P.L.L.C.

(57) ABSTRACT

Novel parathyroid hormone (PTH) peptides and analogs thereof of the PTH(1–34) fragment are disclosed that combine the N-terminal signaling domain (residues 1–9) and the C-terminal binding domain (residues 15–31) via a linker. Nucleic acid molecules and peptides for PTH(1–9)-(Gly)5-PTH(15–31) (PG5) and (1–9)-(Gly)7-PTH(15–31) and a novel PTH receptor are disclosed. Additionally, methods of screening for PTH agonists, pharmaceutical compositions and methods of treatment are disclosed.

11 Claims, 25 Drawing Sheets

OTHER PUBLICATIONS

Gardella, T.J., et al., "Determinants of [Arg$^2$]PTH-(1-34) Binding and Signaling in the Transmembrane Region of the Parathyroid Hormone Receptor," *Endocrinol.* 135:1186-1194 (1994).

Gardella, T.J., et al., "Parathyroid Hormone (PTH)-PTH-related Peptide Hybrid Peptides Reveal Functional Interactions between the 1-14 and 15-34 Domains of the Ligand," *J. Biol. Chem.* 270:6584-6588 (1995).

Gombert, F.O., et al., "Alanine and D-Amino Acid Scan of Human Parathyroid Hormone," in *Peptides: Chemistry. Structure and Biology*, Pravin et al., eds., Mayflower Scientific Ltd., Switzerland, pp. 661-662 (1996).

Gardella, T.J., et al., "Converting Parathyroid Hormone-related Peptide (PTHrP) into a Potent PTH-2 Receptor Agonist," *J. Biol. Chem.* 271:19888-19893 (1996).

Goltzman, D., et al., "Analysis of the Requirements for Parathyroid Hormone Action in Renal Membranes with the Use of Inhibiting Analogues," *J. Biol. Chem.* 250:3199-3203 (1975).

Goud, N.A., et al., "Solid-Phase Synthesis and Biologic Activity of Human Parathyroid Hormone (1-84)," *J. Bone Min. Res.* 6:781-789 (1991).

Holtmann, M.H., et al., "Critical Contributions of Amino-terminal Extracellular Domains in Agonist Binding and Activation of Secretin and Vasoactive Intestinal Polypeptide Receptors," *J. Biol. Chem.* 270:14394-14398 (1995).

Horiuchi, N. et al., "A Parathyroid Hormone Inhibitor in vivo: Design and Biological Evaluation of a Hormone Analog," *Science* 220:1053-1055 (1993).

Ishihara, T., et al., "Molecular cloning and expression of a cDNA encoding the secretin receptor," *EMBO J.* 10:1635-1641 (1991).

Jelinek, L.J., et al., "Expression Cloning and Signaling Properties of the Rat Glucagon Receptor," *Science* 259:1614-1616 (1993).

Jüppner, H., et al., "The Parathyroid Hormone-like Peptide Associated with Humoral Hypercalcemia of Malignancy and Parathyroid Hormone Bind to the Same Receptor on the Plasma Membrane of ROS 17/2.8 Cells," *J. Biol. Chem.* 263:8557-8560 (1988).

Jüppner, H., et al., "The Extracellular Amino-Terminal Region of the Parathyroid Hormone (PTH)/PTH-Related Peptide Receptor Determines the Binding Affinity for Carboxyl-Terminal Fragments of PTH-(1-34)," *Endocrinol.* 134:879-884 (1994).

Karaplis, A.C., et al., "Lethal skeletal dysplasia from targeted disruption of the parathyroid hormone-related peptide gene," *Genes & Develop.* 8:277-289 (1994).

Kolakowski, L.F., "GCRDb: A G-Protein-Coupled Receptor Database," *Receptors and Channels* 2:1-7 (1994).

Kronenberg, H.M., et al., "Parathyroid Hormone: Biosynthesis, Secretion, Chemistry, and Action," in *Physiol. Pharmacol. of Bone*, Mundy, G.R. and Martin, T.J., eds., Springer-Verlag, Berlin pp. 508-567 (1993).

Lanske, B., et al., "PTH/PTHrP Receptor in Early Development and Indian Hedgehog-Regulated Bone Growth," *Science* 273:663-666 (1996).

Lin, H.Y., et al., "Expression Cloning of an Adenylate Cyclase-Coupled Calcitonin Receptor," *Science* 254:1022-1024 (1991).

Luck, M.D., et al., "The (1-14) Fragment of Parathyroid Hormone (PTH) Activates Intact and Amino-Terminally Truncated PTH-1 Receptors," *Mol. Endocrinol.* 13:670-680 (May 1999).

Mannstadt, M., et al., "Evidence for a Ligand Interaction Site at the Amino-Terminus of the Parathyroid Hormone (PTH)/PTH-related Protein Receptor from Cross-linking and Mutational Studies," *J. Biol. Chem.* 273:16890-16896 (Jul. 1998).

Nissenson, R.A., et al., "Synthetic Peptides Comprising the Amino-terminal Sequence of a Parathyroid Hormone-like Protein from Human Malignancies. Binding to Parathyroid Hormone Receptors and Activation of Adenylate Cyclase in Bone Cells and Kidney," *J. Biol. Chem.* 263:12866-12871 (1988).

Nussbaum, S.R., et al., "Parathyroid Hormone-Renal Receptor Interactions," *J. Biol. Chem.* 255:10183-10187 (1980).

Van Ostade, X., et al., "Human TNF mutants with selective activity on the p55 receptor," *Nature* 361:266-269 (1993).

Pinckard, R.N., et al., "Factors Influencing the Immune Response I. Effects of the Physical State of the Antigen and of Lymphoreticular Cell Proliferation on the Response to Intravenous Injection of Bovine Serum Albumin in Rabbits," *Clin. Exp. Immunol.* 2:331-341 (1967).

Rixon, R.H., et al., "Parathyroid Hormone Fragments May Stimulate Bone Growth in Ovariectomized Rats by Activating Adenylyl Cyclase," *J. Bone Min. Res.* 9:1179-1189 (1994).

Robbins, D.C., et al., "Antibodies to Covalent Aggregates of Insulin in Blood of Insulin-Using Diabetic Patients," *Diabetes* 36:838-841 (1987).

Rosenblatt, M., "Parathyroid Hormone: Chemistry and Structure-Activity Relations," *Pathobiol. Annu.* 11:53-86 (1981).

Shen, V., et al., "Effects of Combined and Separate Intermittent Administration of Low-Dose Human Parathyroid Hormone Fragment (1-34) and 17β-Estradiol on Bone Histomorphometry in Ovariectomized Rats with Established Osteopenia," *Calcif. Tissue Int.* 50:214-220 (1992).

Shimizu, M., et al.,Abstract F398, "Type-Substitution Analysis of the Amino-Terminal Fragment of Parathyroid Hormone, PTH(1-14): An Approach toward New Low Molecular Weight PTH Agonists," *J. Bone Min. Res. Program & Abstracts* 14:S289 (Sep. 1999).

Slovik, D.M., et al., "Restoration of Spinal Bone in Osteoporotic Men by Treatment With Human Parathyroid Hormone (1-34) and 1,25-Dihydroxyvitamin D," *J. Bone Min. Res.* 1:377-381 (1986).

Stroop, S.D., et al., "Chimeric Human Calcitonin and Glucagon Receptors Reveal Two Dissociable Calcitonin Interaction Sites," *Biochem.* 34:1050-1057 (1995).

Takasu, H., et al., "Amino-Terminal Modifications of Human Parathyroid Hormone (PTH) Selectively Alter Phospholipase C Signaling via the Type 1 PTH Receptor: Implications for Design of Signal-Specific PTH Ligands," *Biochemistry* 38:13453-13460 (1999).

Tregear, G.W., et al., "Bovine Parathyroid Hormone: Minimum Chain Length of Synthetic Peptide Required for Biological Activity," *Endocrinol.* 93:1349-1353 (1973).

Turner, P.R., et al., "A Putative Selectivity Filter in the G-protein-coupled Receptors for Parathyroid Hormone and Secretin," *J. Biol. Chem.* 271:9205-9208 (1996).

Turner, P.R., et al., Abstract 121, "Single Mutations Allow the PTH2 Receptor to Respond to PTHrP," *J. Bone Min. Res. Program & Abstracts* 12:S133 (Aug. 1997).

Ureña, P., et al., "Regulation of Parthyroid Hormone (PTH)/PTH-Related Peptide Receptor Messenger Ribonucleic Acid by Glucocorticoids and PTH in ROS 17/2.8 and OK Cells," *Endocrinol.* 134:451-456 (1994).

Usdin, T.B., et al., "Identification and Functional Expression of a Receptor Selectively Recognizing Parathyroid Hormone, the PTH2 Receptor," *J. Biol. Chem.* 270:15455-15458 (1995).

Whitfield, J.F., et al., "Restoration of Severely Depleted Femoral Trabecular Bone in Ovariectomized Rats by Parathyroid Hormone-(1-34)," *Calcif. Tissue Int.* 56:227-231 (1995).

Whitfield, J.F., et al., "Stimulation of the Growth of Femoral Trabecular Bone in Ovariectomized Rats by the Novel Parathyroid Hormone Fragment, hPTH-(1-31)$NH_2$ (Ostabolin)," *Calcif. Tissue Int.* 58:81-87 (1996).

Whitfield, J.F., et al., "Comparison of the Ability of Recombinant Human Parathyroid Hormone, rhPTH-(1-84), and hPTH-(1-31)$NH_2$ to Simulate Femoral Trabecular Bone Growth in Ovariectomized Rats," *Calcif. Tissue Int.* 60:26-29 (Jan. 1997).

Whitfield, J.F. and Morley, P., "Small bone-building fragments of parathyroid hormone: new therapeutic agents for osteoporosis," *Trends in Pharmacol. Sci.* 16:382-386 (1995).

Iwakura, M. and Nakamura, T., "Effects of the length of a glycine linker connecting the N-and C-termini of a circularly permuted dihydrofolate reductase," *Protein Engineering* 11:707-713, Oxford University Press (Aug. 1998).

Tsomaia, N., et al., "Cooperative Interaction of Arginine-19 and the N-Terminal Signaling Domain in the Affinity and Potency of Parathyroid Hormone," *Biochem.* 43:3459-3470, American Chemical Society (Mar. 2004).

PG5    PTH(1-9)/(Gly)₅PTH(15-31)

1                                                                          31
A-V-S-E-I-Q-L-M-H-g-g-g-g-g-L-N-S-M-E-R-V-E-W-L-R-K-K-L-Q-D-V-NH2    (SEQ ID NO:9)

1  GCUGUUCCG AAAUCCAGCU GAUGCACGGU GGUGGUGGUG GUCUGAACUC

51 CAUGGAACGU GUUGAAUGGC UGCGUAAAAA ACUGCAGGAC GUU              (SEQ ID NO:14)

---

PG7    PTH(1-9)/(Gly)₇PTH(17-31)

1                                                                          31
A-V-S-E-I-Q-L-M-H-g-g-g-g-g-g-g-S-M-E-R-V-E-W-L-R-K-K-L-Q-D-V-NH2    (SEQ ID NO:11)

1  GCUGUUCCG AAAUCCAGCU GAUGCACGGU GGUGGUGGUG GUGGUGGUUC

51 CAUGGAACGU GUUGAAUGGC UGCGUAAAAA ACUGCAGGAC GUU              (SEQ ID NO:15)

---

PG9    PTH(1-5)/(Gly)₉PTH(15-31)

1                                                                          31
A-V-S-E-I-g-g-g-g-g-g-g-g-g-L-N-S-M-E-R-V-E-W-L-R-K-K-L-Q-D-V-NH2    (SEQ ID NO:13)

1  GCUGUUCCGU UGGUGGUGG GGUGGUGGUG GUCUGAACUC

51 CAUGGAACGU GUUGAAUGGC UGCGUAAAAA ACUGCAGGAC GUU              (SEQ ID NO:16)

FIG.1

Family B Ligands

This is a list-- not an alignment:

```
             1         5          15         25
hpth         1 SVSEI QLMHNLGKHL NSMERVEWLR KKLQDVHNF                                              (SEQ ID NO:17)
hpthrp       1 AVSEH QLLHDKGKSI QDLRRRFFLH HLIAEIHTA                                              (SEQ ID NO:18)
hpacap       1 HSDGI FTDSYSRYRK QMAVKKYLAA VLGKRYKQR VNK                                          (SEQ ID NO:19)
hvip         1 HSDAV FTDNYTRLRK QMAVKKYLNS ILN                                                    (SEQ ID NO:20)
hgrf         1 YADAI FTNSYRKVLG QLSARKLLQD IMSR                                                   (SEQ ID NO:21)
hphm         1 HADGV FTSDFSKLLG QLSAKKYLES LM                                                     (SEQ ID NO:22)
hglp1        7 HAEGT FTSDVSSYLE GQAAKEFIAW LVKGRG                                                 (SEQ ID NO:23)
hglucagon    1 HSQGT FTSDYSKYLD SRRAQDFVQW LMNT                                                   (SEQ ID NO:24)
gip          1 YAEGT FISDYSIAMD KIHQQDFVNW LLAQKGKKN DWKHNITQ                                     (SEQ ID NO:25)
hsecretin    1 HSDGT FTSELSRLRE GARLQRLLQG LV                                                     (SEQ ID NO:26)
hcalcitonin  1 CGNLS TCMLGTYTQD FNKFHTFPQT AIGVGAP                                                (SEQ ID NO:27)
hcgrp-2      1 ACNTA TCVTHRLAGL LSRSGGMVKS NFVPTNVGSKAF                                           (SEQ ID NO:28)
hcgrp1       1 ACDTA TCVTHRLAGL LSRSGGVVKN NFVPTNVGSKAF                                           (SEQ ID NO:29)
hamylin      1 KCNTA TCATQRLANF LVHSSNNFGA ILSSTNVGSNTY                                           (SEQ ID NO:30)
hadrenomedu  1 GCRFG TCTVQKLAHQ IYQFTDKDKD NVAPRSKISPQ                                            (SEQ ID NO:31)
hcrf         1 SEEPP ISLDLTFHLL REVLEMARAE QLAQQAHSNRKLMEII                                       (SEQ ID NO:32)
sauvagine    1 EEPPI SIDLSLELLR KMIEIEKQEK EKQQAANNRLLLDTI                                        (SEQ ID NO:33)
msdh         1 TGAQS LSIVAPLDVL RQRLMNELNR RRMRELQGSRIQQNRQLLTSI                                   (SEQ ID NO:34)
Maxadilin    1 CDATC QFRKAIDDCQ KQAHHSNVLQ TSVQTTATFTSMDTSQLPGNSVFKECMKQKKKEFSSGK                  (SEQ ID NO:35)
```

FIG.2

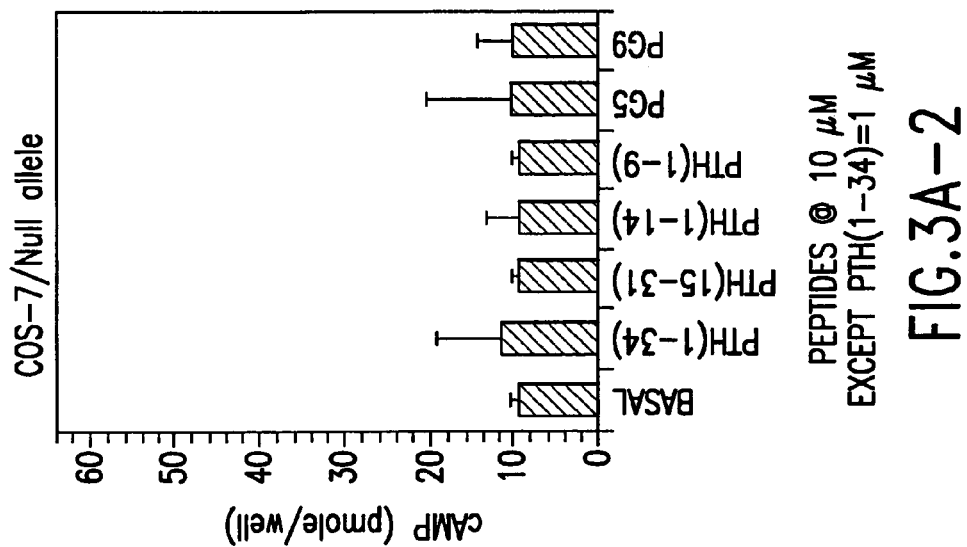
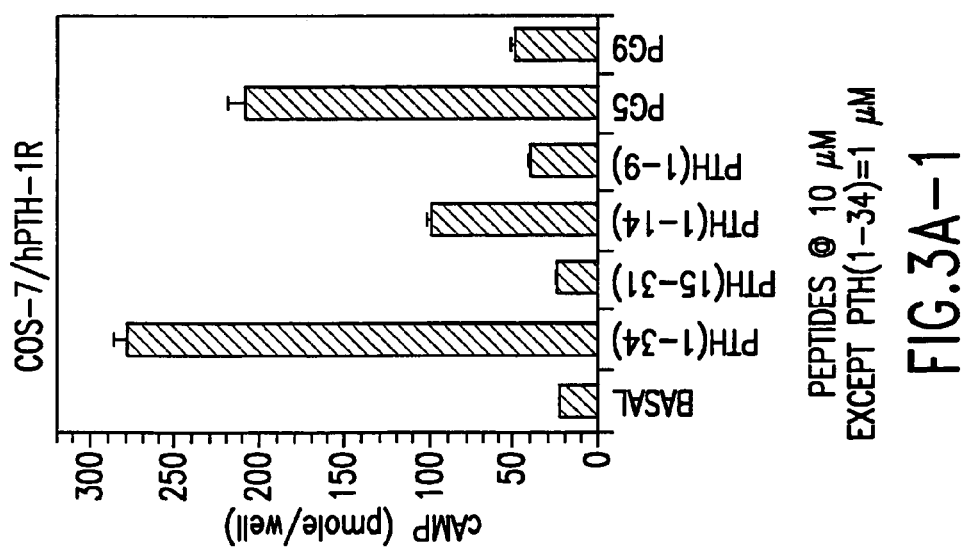

| ALANINE SCAN OF PTH (17–31) |||||
|---|---|---|---|
| NATIVE PTH(17–31) || BINDING IC$_{50}$ ($\mu$M) 1.0±0.1 | n 14 |
| POSITION | SUBSTITUTION | | |
| 17 | Ser→Ala | 1.5±0.2 | 14 |
| 18 | Met→Ala | 1.5±0.3 | 5 |
| 19 | Glu→Ala | 0.7±0.1 | 5 |
| 20 | Arg→Ala | 90.5±50.0 | 5 |
| 21 | Val→Ala | 1.7±0.2 | 5 |
| 22 | Glu→Ala | 0.6±0.2 | 8 |
| 23 | Trp→Ala | >100 | 8 |
| 24 | Leu→Ala | 67.5±14.3 | 5 |
| 25 | Arg→Ala | 3.8±0.9 | 5 |
| 26 | Lys→Ala | 8.3±1.2 | 5 |
| 27 | Lys→Ala | 1.1±0.1 | 5 |
| 28 | Leu→Ala | 9.9±1.4 | 5 |
| 29 | Gln→Ala | 0.9±0.1 | 5 |
| 30 | Asp→Ala | 1.1±0.2 | 5 |
| 31 | Val→Ala | 3.8±0.6 | 5 |

Competition binding analysis for each PTH(17–31) peptide analog was performed in COS-7 cells transfected with PTH-2 receptors. IC$_{50}$ is the dose of a peptide analog which inhibited by 50% the binding of $^{125}$I-rPTH(1–34). Each analysis was performed the number of times indicated(n).

FIG.6

MAP of: tether-1.seq from: 2319 to: 3698
PTH(1-9) linked to Glu-182 of rat receptor. insert immediately
after Tyr23 cleavage site.

```
ATGGGGGCCGCCCGGATCGCACCCAGCCTGGCGCTCCTACTCTGCTGCCCAGTGCTCAGC
 M  G  A  A  R  I  A  P  S  L  A  L  L  L  C  C  P  V  L  S  -
TCCGCcTATGCGGUUUCCGAAAUCCAGCUGAUGCACggcggaggaggcGAGGTATTTGAC
 S  A  Y  A  V  S  E  I  Q  L  M  H  G  G  G  E  V  F  D  -
CGCCTAGGCATGATCTACACCGTGGGATACTCCATGTCTCTCGCCTCCCTCACGGTGGCT
 R  L  G  M  I  Y  T  V  G  Y  S  M  S  L  A  S  L  T  V  A  -
GTGCTCATCCTGGCCTATTTTAGGCGGCTGCACTGCACGCGCAACTACATCCACATGCAC
 V  L  I  L  A  Y  F  R  R  L  H  C  T  R  N  Y  I  H  M  H  -
ATGTTCCTGTCGTTTATGCTGCGCGCCGCGAGCATCTTCGTGAAGGACGCTGTGCTCTAC
 M  F  L  S  F  M  L  R  A  A  S  I  F  V  K  D  A  V  L  Y  -
TCTGGCTTCACGCTGGATGAGGCCGAGCGCCTCACAGAGGAAGAGTTGCACATCATCGCG
 S  G  F  T  L  D  E  A  E  R  L  T  E  E  E  L  H  I  I  A  -
CAGGTGCCACCTCCGCCGGCCGCTGCCGCCGTAGGCTACGCTGGCTGCCGCGTGGCGGTG
 Q  V  P  P  P  P  A  A  A  A  V  G  Y  A  G  C  R  V  A  V  -
ACCTTCTTCCTCTACTTCCTGGCTACCAACTACTACTGGATcCTGGTGGAGGGGCTGTAC
 T  F  F  L  Y  F  L  A  T  N  Y  Y  W  I  L  V  E  G  L  Y  -
TTGCACAGCCTCATCTTCATGGCCTTTTTCTCAGAGAAGAAGTACCTGTGGGGCTTCACC
 L  H  S  L  I  F  M  A  F  F  S  E  K  K  Y  L  W  G  F  T  -
ATCTTTGGCTGGGGTCTACCGGCTGTCTTCGTGGCTGTGTGGGTCGGTGTCAGAGCAACC
 I  F  G  W  G  L  P  A  V  F  V  A  V  W  V  G  V  R  A  T  -
TTGGCCAACACTGGGTGCTGGGATCTGAGCTCCGGGCACAAGAAGTGGATCATCCAGGTG
 L  A  N  T  G  C  W  D  L  S  S  G  H  K  K  W  I  I  Q  V  -
CCCATCCTGGCATCTGTTGTGCTCAACTTCATCCTTTTTATCAACATCATCCGGGTGCTT
 P  I  L  A  S  V  V  L  N  F  I  L  F  I  N  I  I  R  V  L  -
GCCACTAAGCTTCGGGAGACCAATGCGGGCCGGTGTGACACCAGGCAGCAGTACCGGAAG
 A  T  K  L  R  E  T  N  A  G  R  C  D  T  R  Q  Q  Y  R  K  -
CTGCTCAGGTCCACGTTGGTGCTCGTGCCGCTCTTTGGTGTgCACTACACCGTCTTCATG
 L  L  R  S  T  L  V  L  V  P  L  F  G  V  H  Y  T  V  F  M  -
GCCTTGCCGTACACCGAGGTCTCAGGGACATTGTGGCAGATCCAGATGCATTATGAGATG
 A  L  P  Y  T  E  V  S  G  T  L  W  Q  I  Q  M  H  Y  E  M  -
CTCTTCAACTCCTTCCAGGGATTTTTTGTTGCCATCATATACTGTTTCTGCAATGGTGAG
 L  F  N  S  F  Q  G  F  F  V  A  I  I  Y  C  F  C  N  G  E  -
GTGCAGGCAGAGATTAGGAAGTCATGGAGCCGCTGGACACTGGCGTTGGACTTCAAGCGC
 V  Q  A  E  I  R  K  S  W  S  R  W  T  L  A  L  D  F  K  R  -
AAAGCACGAAGTGGGAGTAGCAGCTACAGCTATGGCCCAATGGTGTCTCACACGAGTGTG
 K  A  R  S  G  S  S  S  Y  S  Y  G  P  M  V  S  H  T  S  V  -
ACCAATGTGGGCCCCCGTGCAGGACTCAGCCTCCCCCTCAGCCCCCGCCTGCCTCCTGCC
 T  N  V  G  P  R  A  G  L  S  L  P  L  S  P  R  L  P  P  A  -
ACTACCAATGGCCACTCCCAGCTGCCTGGCCATGCCAAGCCAGGGGCTCCAGCCACTGAG
 T  T  N  G  H  S  Q  L  P  G  H  A  K  P  G  A  P  A  T  E  -
ACTGAAACCCTACCAGTCACTATGGCGGTTCCCAAGGACGATGGATTCCTTAACGGCTCC
 T  E  T  L  P  V  T  M  A  V  P  K  D  D  G  F  L  N  G  S  -
TGCTCAGGCCTGGATGAGGAGGCCTCCGGGTCTGCGCGGCCGCCTCCATTGTTGCAGGAA
 C  S  G  L  D  E  E  A  S  G  S  A  R  P  P  P  L  L  Q  E  -
GGATGGGAAACAGTCATGTGA           (SEQ ID NO:36)
 G  W  E  T  V  M  *             (SEQ ID NO:37)
```

FIG.7 rHA-WT

FIG.8A-1

Del-NT

FIG.8A-2

Tether-1

FIG.8A-3

MAP of: tether-1C.seq  check: 6795  from: 2319  to: 3326
Stop codon at 481 added to Tether-1

```
     ATGGGGGCCGCCCGGATCGCACCCAGCCTGGCGCTCCTACTCTGCTGCCCAGTGCTCAGC
a    M  G  A  A  R  I  A  P  S  L  A  L  L  L  C  C  P  V  L  S  -

TCCGCcTATGCGGUUUCCGAAAUCCAGCUGAUGCACggcggaggaggcGAGGTATTTGAC
a    S  A  Y  A  V  S  E  I  Q  L  M  H  G  G  G  G  E  V  F  D  -

CGCCTAGGCATGATCTACACCGTGGGATACTCCATGTCTCTCGCCTCCCTCACGGTGGCT
a    R  L  G  M  I  Y  T  V  G  Y  S  M  S  L  A  S  L  T  V  A  -

GTGCTCATCCTGGCCTATTTTAGGCGGCTGCACTGCACGCGCAACTACATCCACATGCAC
a    V  L  I  L  A  Y  F  R  R  L  H  C  T  R  N  Y  I  H  M  H  -

ATGTTCCTGTCGTTTATGCTGCGCGCCGCGAGCATCTTCGTGAAGGACGCTGTGCTCTAC
a    M  F  L  S  F  M  L  R  A  A  S  I  F  V  K  D  A  V  L  Y  -

TCTGGCTTCACGCTGGATGAGGCCGAGCGCCTCACAGAGGAAGAGTTGCACATCATCGCG
a    S  G  F  T  L  D  E  A  E  R  L  T  E  E  E  L  H  I  I  A  -

CAGGTGCCACCTCCGCCGGCCGCTGCCGCCGTAGGCTACGCTGGCTGCCGCGTGGCGGTG
a    Q  V  P  P  P  P  A  A  A  A  V  G  Y  A  G  C  R  V  A  V  -

ACCTTCTTCCTCTACTTCCTGGCTACCAACTACTACTGGATcCTGGTGGAGGGGCTGTAC
a    T  F  F  L  Y  F  L  A  T  N  Y  Y  W  I  L  V  E  G  L  Y  -

TTGCACAGCCTCATCTTCATGGCCTTTTTCTCAGAGAAGAAGTACCTGTGGGGCTTCACC
a    L  H  S  L  I  F  M  A  F  F  S  E  K  K  Y  L  W  G  F  T  -

ATCTTTGGCTGGGGTCTACCGGCTGTCTTCGTGGCTGTGTGGGTCGGTGTCAGAGCAACC
a    I  F  G  W  G  L  P  A  V  F  V  A  V  W  V  G  V  R  A  T  -

TTGGCCAACACTGGGTGCTGGGATCTGAGCTCCGGGCACAAGAAGTGGATCATCCAGGTG
a    L  A  N  T  G  C  W  D  L  S  S  G  H  K  K  W  I  I  Q  V  -

CCCATCCTGGCATCTGTTGTGCTCAACTTCATCCTTTTTATCAACATCATCCGGGTGCTT
a    P  I  L  A  S  V  V  L  N  F  I  L  F  I  N  I  I  R  V  L  -

GCCACTAAGCTTCGGGAGACCAATGCGGGCCGGTGTGACACCAGGCAGCAGTACCGGAAG
a    A  T  K  L  R  E  T  N  A  G  R  C  D  T  R  Q  Q  Y  R  K  -

CTGCTCAGGTCCACGTTGGTGCTCGTGCCGCTCTTTGGTGTgCACTACACCGTCTTCATG
a    L  L  R  S  T  L  V  L  V  P  L  F  G  V  H  Y  T  V  F  M  -

GCCTTGCCGTACACCGAGGTCTCAGGGACATTGTGGCAGATCCAGATGCATTATGAGATG
a    A  L  P  Y  T  E  V  S  G  T  L  W  Q  I  Q  M  H  Y  E  M  -

CTCTTCAACTCCTTCCAGGGATTTTTTGTTGCCATCATATACTGTTTCTGCAATGGTGAG
a    L  F  N  S  F  Q  G  F  F  V  A  I  I  Y  C  F  C  N  G  E  -

GTGCAGGCAGAGATTAGGAAGTCATGGAGCCGCTGGACACTGGCGTaG    (SEQ ID NO:38)
a    V  Q  A  E  I  R  K  S  W  S  R  W  T  L  A  *   - (SEQ ID NO:39)
```

FIG.9

MAP of rdel(Nt/Ct)

```
    ATGGGGGCCGCCCGGATCGCACCCAGCCTGGCGCTCCTACTCTGCTGCCCAGTGCTCAGC
a   M  G  A  A  R  I  A  P  S  L  A  L  L  L  C  C  P  V  L  S  -

TCCGCATATGCGCTGGAGGTATTTGACCGCCTAGGCATGATCTACACCGTGGGATACTCC
a   S  A  Y  A  L  E  V  F  D  R  L  G  M  I  Y  T  V  G  Y  S  -

ATGTCTCTCGCCTCCCTCACGGTGGCTGTGCTCATCCTGGCCTATTTTAGGCGGCTGCAC
a   M  S  L  A  S  L  T  V  A  V  L  I  L  A  Y  F  R  R  L  H  -

TGCACGCGCAACTACATCCACATGCACATGTTCCTGTCGTTTATGCTGCGCGCCGCGAGC
a   C  T  R  N  Y  I  H  M  H  M  F  L  S  F  M  L  R  A  A  S  -

ATCTTCGTGAAGGACGCTGTGCTCTACTCTGGCTTCACGCTGGATGAGGCCGAGCGCCTC
a   I  F  V  K  D  A  V  L  Y  S  G  F  T  L  D  E  A  E  R  L  -

ACAGAGGAAGAGTTGCACATCATCGCGCAGGTGCCACCTCCGCCGGCCGCTGCCGCCGTA
a   T  E  E  E  L  H  I  I  A  Q  V  P  P  P  P  A  A  A  A  V  -

GGCTACGCTGGCTGCCGCGTGGCGGTGACCTTCTTCCTCTACTTCCTGGCTACCAACTAC
a   G  Y  A  G  C  R  V  A  V  T  F  F  L  Y  F  L  A  T  N  Y  -

TACTGGATcCTGGTGGAGGGGCTGTACTTGCACAGCCTCATCTTCATGGCCTTTTTCTCA
a   Y  W  I  L  V  E  G  L  Y  L  H  S  L  I  F  M  A  F  F  S  -

GAGAAGAAGTACCTGTGGGGCTTCACCATCTTTGGCTGGGGTCTACCGGCTGTCTTCGTG
a   E  K  K  Y  L  W  G  F  T  I  F  G  W  G  L  P  A  V  F  V  -

GCTGTGTGGGTCGGTGTCAGAGCAACCTTGGCCAACACTGGGTGCTGGGATCTGAGCTCC
a   A  V  W  V  G  V  R  A  T  L  A  N  T  G  C  W  D  L  S  S  -

GGGCACAAGAAGTGGATCATCCAGGTGCCCATCCTGGCATCTGTTGTGCTCAACTTCATC
a   G  H  K  K  W  I  I  Q  V  P  I  L  A  S  V  V  L  N  F  I  -

CTTTTTATCAACATCATCCGGGTGCTTGCCACTAAGCTTCGGGAGACCAATGCGGGCCGG
a   L  F  I  N  I  I  R  V  L  A  T  K  L  R  E  T  N  A  G  R  -

TGTGACACCAGGCAGCAGTACCGGAAGCTGCTCAGGTCCACGTTGGTGCTCGTGCCGCTC
a   C  D  T  R  Q  Q  Y  R  K  L  L  R  S  T  L  V  L  V  P  L  -

TTTGGTGTgCACTACACCGTCTTCATGGCCTTGCCGTACACCGAGGTCTCAGGGACATTG
a   F  G  V  H  Y  T  V  F  M  A  L  P  Y  T  E  V  S  G  T  L  -

TGGCAGATCCAGATGCATTATGAGATGCTCTTCAACTCCTTCCAGGGATTTTTTGTTGCC
a   W  Q  I  Q  M  H  Y  E  M  L  F  N  S  F  Q  G  F  F  V  A  -

ATCATATACTGTTTCTGCAATGGTGAGGTGCAGGCAGAGATTAGGAAGTCATGGAGCCGC
a   I  I  Y  C  F  C  N  G  E  V  Q  A  E  I  R  K  S  W  S  R  -

TGGACACTGGCGTaG                    (SEQ ID NO:40)
a   W  T  L  A  *  -                  (SEQ ID NO:41)
```

FIG.10

Oligo is designed to join PTH(1-9) sequence to core of receptor using a Gly linker.
Test for constitutive activation.
Insert immediately after predicted signal peptidase cleavage site @Tyr23, use Ala24 as Ala1 of PTH.
Join to Glu-182, = boundry of exonG/M1.

rHA.WT map   underline = flanking homology (1-40)

```
a   ATGGGGGCCGCCCGGATCGCACCCAGCCTGGCGCTCCTACTCTGCTGCTGCCAGTGCTCAGC   -
    M  G  A  A  R  I  A  P  S  L  A  L  L  L  C  C  P  V  L  S   -
          NDEI--
a   TCCGCATATGCGCTGGTGGATGCGGACGATGTCTTTACCAAAGAGGAACAGATTTTCCTG   -        (SEQ ID NO:46)
    S  A  Y  A  L  V  D  A  D  D  V  F  T  K  E  E  Q  I  F  L   -        (SEQ ID NO:53)
```

(161-200)

```
a   AACCGGACGTGGGCCAACTACAGCGAGTGCCTCAAGTTCATGACCAATGAGACCCGGGAA  612
553 -------+---------+---------+---------+---------+---------+---  -
    N  R  T  W  A  N  Y  S  E  C  L  K  F  M  T  N  E  T  R  E   - a   CGGGAGGTATTTGACCGCCTAGGCATGATCTACACCGTGGGATACTCCATGTCTCTCGCC  672     (SEQ ID NO:47)
613 -------+---------+---------+---------+---------+---------+---  -     (SEQ ID NO:54)
    R  E  V  F  D  R  L  G  M  I  Y  T  V  G  Y  S  M  S  L  A   -
```

FIG.11A

Backtranslate PTH(1-9)Gly4.:

```
                GCUGUUUCCGAAAUCCAGCUGAUGCACggcggagaggc          (SEQ ID NO:48)
```

Insert PTH(2-9).Gly4 between A24 and E182, use about 30 nts for flanking homology
5'flank Hom = 33 nt, 3'flank Hom = 30 nt, total = 99 nts.

FIG.11B

Oligo: Sequence ID#: E16631A1
CTCTGCTGCCCAGTGCTCAGCTCCGCcTATGCGGTTTCCGAAATCCAGCTGATGCACggcggaggaggc
GAGGTATTTGACCGCCTAGGCATGATCTAC                                    (SEQ ID NO:49)

GCG check:
MAP of: Y23E182G4PTH1-9.seq from: 1 to: 99
DNA sequence for making Tethered PTH ligand/receptor
Receptor = rat PTH1 Rec
Insert PTH(1-9)-Gly4 sequence between Tyr23 and Glu182.
USe Ala24 as codon 1 of PTH, flanking homology of ~30 nts
Takes out NDEI site at Ala 22 GCA->GCC
With 1 enzymes: NDEI

FIG.11C

```
    CTCTGCTGCCCAGTGCTCAGCTCCGCcTATGCGGTTTCCGAAATCCAGCTGATGCACggc
a    L  C  C  P  V  L  S  S  A  Y  A  V  S  E  I  Q  L  M  H  G  - ggaggaggcGAGGTATTTGACCGCCTAGGCATGATCTAC      (SEQ ID NO:50)
a    G  G  G  E  V  F  D  R  L  G  M  I  Y  -   (SEQ ID NO:55)
```

Helix II: ~/rec-dna>more tether-1 map from: 2350 to:2650

Tethered PTH (1-9) to core receptor.
PTH (1-9) linked to Glu-182 of rat receptor.
Insert immediately after Tyr23 cleavage site.
Oligo tether-1 spans 2358 to 2891
takes out NDEI at 2390 Ala-22.

FIG.11D

NdeI CA'TA_TG                    Cuts at:    1790         1790
                         Size:           5769
PSORT of : rDelE1-G.seq from: 1 to:5736
*To be used as template SS DNA for Tether-1 OM.
Th.1 enzymes: NDEI NdeI CA'TA_TG Cuts at:    1790         2384         1790
Size:                594          5142

FIG.11E (1-40)
Oligo Mini-HA-1:

Sequence ID#: E16853A1

CTCTGCTGCCCAGTGCTCAGCTCCGCATATccctacgacgtcccgactacgccggcGAGGTATTTGACCGCCTAGGCATGATCTAC  (SEQ ID NO:51)

FIG. 11F

MAP of: mini-HA.seq from: 1 to: 96
Oligo sequence for adding HA Epitope tag to Headless rat P1R.
Insert 9 aa tag, YPYDVPDYA, between Tyr23 and Glu182, using
Tyr 23 as codon 1 of tag, and add 4 glys for spacer. Flanking homology of ~30
nts. Takes out NDEI site at Ala 24 GCG->ccc (31-33).

With 1 enzymes: NDEI          September 15, 1998 17:16 ..

```
    CTCTGCTGCCCAGTGCTCAGCTCCGCATATccctacgacgtcccgactacgccggcgga
1   ---------+---------+---------+---------+---------+---------+ 60
a     L  C  C  P  V  L  S  S  A  Y  P  Y  D  V  P  D  Y  A  G  G    - ggaggcGAGGTATTTGACCGCCTAGGCATGATCTAC     (SEQ ID NO:52)
61  ---------+---------+---------+------ 96
a    G  G  E  V  F  D  R  L  G  M  I  Y  -    (SEQ ID NO:56)
```

FIG. 11G

Enzymes that do not cut: NdeI hTether-1  From human PTH-1 receptor by replacing Ala24 to Arg181 with
Ala1 to His9 of PTH, then 4-Gly linker between His9 and Glu182 by
oligonucleotide mutagenesis with oligo E20986

```
        atgggGAccGCccggatcgcacccggcctggcgctcctgctctgctgccccgtgctcagc
   2287 ---+---------+---------+---------+---------+---------+------ 2346
      a   M  G  T  A  R  I  A  P  G  L  A  L  L  L  C  C  P  V  L  S  -
        tccgcgtacgcggtttccgaaatccagctgatgcacggcggaggaggcgaggtgtttgac
   2347 ---+---------+---------+---------+---------+---------+------ 2406
      a   S  A  Y  A  V  S  E  I  Q  L  M  H  G  G  G  G  E  V  F  D  -
        cgcctgggcatgatttacaccgtgggctactccgtgtccctggcgtccctcaccgtagct
   2407 ---+---------+---------+---------+---------+---------+------ 2466
      a   R  L  G  M  I  Y  T  V  G  Y  S  V  S  L  A  S  L  T  V  A  -
        gtgctcatcctggcctactttaggcggctgcactgcacgcgcaactacatccacatgcac
   2467 ---+---------+---------+---------+---------+---------+------ 2526
      a   V  L  I  L  A  Y  F  R  R  L  H  C  T  R  N  Y  I  H  M  H  -
        ctgttcctgtccttcatgctgcgcgccgtgagcatcttcgtcaaggacgctgtgctctac
   2527 ---+---------+---------+---------+---------+---------+------ 2586
      a   L  F  L  S  F  M  L  R  A  V  S  I  F  V  K  D  A  V  L  Y  -
        tctggcgccacgcttgatgaggctgagcgcctcaccgaggaggagctgcgcgccatcgcc
   2587 ---+---------+---------+---------+---------+---------+------ 2646
      a   S  G  A  T  L  D  E  A  E  R  L  T  E  E  E  L  R  A  I  A  -
        caggcgcccccgccgcctgccaccgccgctgccggctacgcgggctgcagggtggctgtg
   2647 ---+---------+---------+---------+---------+---------+------ 2706
      a   Q  A  P  P  P  P  A  T  A  A  A  G  Y  A  G  C  R  V  A  V  -
        accttcttcctttacttcctggccaccaactactactggattctggtggaggggctgtac
   2707 ---+---------+---------+---------+---------+---------+------ 2766
      a   T  F  F  L  Y  F  L  A  T  N  Y  Y  W  I  L  V  E  G  L  Y  -
        ctgcacagcctcatcttcatggccttcttctcagagaagaagtacctgtggggcttcaca
   2767 ---+---------+---------+---------+---------+---------+------ 2826
      a   L  H  S  L  I  F  M  A  F  F  S  E  K  K  Y  L  W  G  F  T  -
        gtcttcggctggggtctgcccgctgtcttcgtggctgtgtgggtcagtgtcagagctacc
   2827 ---+---------+---------+---------+---------+---------+------ 2886
      a   V  F  G  W  G  L  P  A  V  F  V  A  V  W  V  S  V  R  A  T  -
        ctggccaacaccgggtgctgggacttgagctccgggaacaaaaagtggatcatccaggtg
   2887 ---+---------+---------+---------+---------+---------+------ 2946
      a   L  A  N  T  G  C  W  D  L  S  S  G  N  K  K  W  I  I  Q  V  -
        cccatcctggcctccattgtgctcaacttcatcctcttcatcaatatcgtccgggtgctc
   2947 ---+---------+---------+---------+---------+---------+------ 3006
      a   P  I  L  A  S  I  V  L  N  F  I  L  F  I  N  I  V  R  V  L  -
        gccaccaagctgcgggagaccaacgccggccggtgtgacacacggcagcagtaccggaag
   3007 ---+---------+---------+---------+---------+---------+------ 3066
      a   A  T  K  L  R  E  T  N  A  G  R  C  D  T  R  Q  Q  Y  R  K  -
```

FIG.17A

```
        ctgctcaaatccacgctggtgctcatgcccctctttggcgtccactacattgtcttcatg
   3067 ---+---------+---------+---------+---------+---------+------ 3126
 a      L  L  K  S  T  L  V  L  M  P  L  F  G  V  H  Y  I  V  F  M  -
        gccacaccatacaccgaggtctcagggacgctctggcaagtccagatgcactatgagatg
   3127 ---+---------+---------+---------+---------+---------+------ 3186
 a      A  T  P  Y  T  E  V  S  G  T  L  W  Q  V  Q  M  H  Y  E  M  -
        ctcttcaactccttccagggattttttgtcgcaatcatatactgtttctgcaatggcgag
   3187 ---+---------+---------+---------+---------+---------+------ 3246
 a      L  F  N  S  F  Q  G  F  F  V  A  I  I  Y  C  F  C  N  G  E  -
        gtacaagctgagatcaagaaatcttggagccgctggacactggcactggacttcaagcga
   3247 ---+---------+---------+---------+---------+---------+------ 3306
 a      V  Q  A  E  I  K  K  S  W  S  R  W  T  L  A  L  D  F  K  R  -
        aaggcacgcagcgggagcagcagctatagctacggccccatggtgtcccacacaagtgtg
   3307 ---+---------+---------+---------+---------+---------+------ 3366
 a      K  A  R  S  G  S  S  S  Y  S  Y  G  P  M  V  S  H  T  S  V  -
        accaatgtcggccccgtgtgggactcggcctgcccctcagcccccgcctactgcccact
   3367 ---+---------+---------+---------+---------+---------+------ 3426
 a      T  N  V  G  P  R  V  G  L  G  L  P  L  S  P  R  L  L  P  T  -
        gccaccaccaacggccaccctcagctgcctggccatgccaagccagggaccccagccctg
   3427 ---+---------+---------+---------+---------+---------+------ 3486
 a      A  T  T  N  G  H  P  Q  L  P  G  H  A  K  P  G  T  P  A  L  -
        gagaccctcgagaccacaccacctgccatggctgctcccaaggacgatgggttcctcaac
   3487 ---+---------+---------+---------+---------+---------+------ 3546
 a      E  T  L  E  T  T  P  P  A  M  A  A  P  K  D  D  G  F  L  N  -
        ggctcctgctcaggcctggacgaggaggcctctgggcctgagcggccacctgccctgcta
   3547 ---+---------+---------+---------+---------+---------+------ 3606
 a      G  S  C  S  G  L  D  E  E  A  S  G  P  E  R  P  P  A  L  L  -
        caggaagagtgggagacagtcatgtgaccaggcgctgggggct        (SEQ ID NO:61)
   3607 ---+---------+---------+---------+---------     3649
 a      Q  E  E  W  E  T  V  M  *                         (SEQ ID NO:62)
```

FIG.17B

```
hdelNT
human PTH-1 rec deleted for 24-181; Joins Tyr23 to Glu182.
February 25, 1999 13:38

TGGATCCCGCCGGCCCTAGGCGGTGGCGatgggGAccGCccgatcgcaccggcctggcg
2260   +---------+---------+---------+---------+---------+---------+  2319
                               M  G  T  A  R  I  A  P  G  L  A ctcctgctctgctgccccgtgctcagctccgcAtaTgaggtgtttgaccgcctgggcatg
2320   +---------+---------+---------+---------+---------+---------+  2379
       L  L  C  C  P  V  L  S  S  A  Y  E  V  F  D  R  L  G  M atttacacggtgggctactccgtgtccctggcgtcccttgccactacatccacctgtcctg
2380   +---------+---------+---------+---------+---------+---------+  2439
       I  Y  T  V  G  Y  S  V  S  L  A  S  L  T  V  A  V  I  L gcctactttaggcgcgtgcactgcaacgcgcaactacatccacatgcacctgttcctgtcc
2440   +---------+---------+---------+---------+---------+---------+  2499
       A  Y  F  R  R  L  H  C  T  R  N  Y  I  H  M  H  L  F  L  S ttcatgctgcgcgccgtgagcatcttcgtcaaggacgctgtgctcctactctggcgccacg
2500   +---------+---------+---------+---------+---------+---------+  2559
       F  M  L  R  A  V  S  I  F  V  K  D  A  V  L  Y  S  G  A  T cttgatgaggctgagcgcctcaccgaggaggagctgcgcaggtggctgtgacctttcttcctt
2560   +---------+---------+---------+---------+---------+---------+  2619
       L  D  E  A  E  R  L  T  E  E  E  L  R  A  I  A  Q  A  P  P ccgcctgccaccgccgctgccacaactactactggagagaagtacctgtggggcttcacagcctc
2620   +---------+---------+---------+---------+---------+---------+  2679
       P  P  A  T  A  A  A  G  Y  A  G  C  R  V  A  V  T  F  F  L tacttcctgccacaactactactggagagaagtacctgtgggcttcacagtcttcggctgg
2680   +---------+---------+---------+---------+---------+---------+  2739
       Y  F  L  A  T  N  Y  Y  W  I  L  V  E  G  L  Y  L  H  S  L atcttcatggccttcttcttctcagagaagaagtacctgtggggcttcacagtcttcggctgg
2740   +---------+---------+---------+---------+---------+---------+  2799
       I  F  M  A  F  F  S  E  K  K  Y  L  W  G  F  T  V  F  G  W ggtctgccccgctgtgtcttcgtggccgtggaacaaaaagtgatcatccaggtgccatcctggcc
2800   +---------+---------+---------+---------+---------+---------+  2859
       G  L  P  A  V  F  V  A  V  W  V  S  V  R  A  T  L  A  N  T gggtgctgggacttgagctccgggaacaaaaagtggatcatccaggtgccgggtgctgccaccaagctg
2860   +---------+---------+---------+---------+---------+---------+  2919
       G  L  P  A  V  F  V  A  V  W  V  S  V  R  A  T  L  A  N  T tccattgtgctcaacttcatcctcttcatcaatatcgtccgggtgctcgccaccaagctg
2860   +---------+---------+---------+---------+---------+---------+  2919
       G  C  W  D  L  S  S  G  N  K  W  I  L  Q  V  P  I  L  A cggagaccaacgccgccgtgtgacacacggagcagcagtaccggaagctgctcaaatcc
2920   +---------+---------+---------+---------+---------+---------+  2979
       S  I  V  L  N  F  I  L  F  I  N  I  V  R  V  L  A  T  K  L 2980   +---------+---------+---------+---------+---------+---------+  3039
       R  E  T  N  A  G  R  C  D  T  R  Q  Q  Y  R  K  L  L  K  S
```

FIG. 18A

```
3040  acgctggtgctcatgcccctctttggcgtccactacattgtctttcatgccacaccatac
 a    ----+----+----+----+----+----+----+----+----+----+----+----+  3099
      T   L   V   L   M   P   L   F   G   V   H   Y   I   V   F   M   A   T   P   Y 3100  accgaggtctcagggacgctctggcaagtccagatgcactatgagatgctctttcaactcc
 a    ----+----+----+----+----+----+----+----+----+----+----+----+  3159
      T   E   V   S   G   T   L   W   Q   V   Q   M   H   Y   E   M   L   F   N   S 3160  ttccagggatttttttgtcgcaatcatatactgttttctgcaatggcgaggtacaagctgag
 a    ----+----+----+----+----+----+----+----+----+----+----+----+  3219
      F   Q   G   F   F   V   A   I   I   Y   C   F   C   N   G   E   V   Q   A   E 3220  atcaagaaatcttggagccgctggacactggacttcaagcgaaggcacgcagc
 a    ----+----+----+----+----+----+----+----+----+----+----+----+  3279
      I   K   K   S   W   S   R   W   T   L   D   F   K   R   K   A   R   S 3280  gggagcagcagctatagctacggcccatggtgtcccacacaagtgtgaccaatgtcggc
 a    ----+----+----+----+----+----+----+----+----+----+----+----+  3339
      G   S   S   S   Y   S   Y   G   P   M   V   S   H   T   S   V   T   N   V   G 3340  ccccgtgtgggactcggcctgcccctcagccccgcctactgccactgccaccaccaac
 a    ----+----+----+----+----+----+----+----+----+----+----+----+  3399
      P   R   V   G   L   G   L   P   L   S   P   R   L   L   P   T   A   T   T   N 3400  ggccaccctcagctgcctggccatgccaaggacgatggttcctcaacggctcctgctca
 a    ----+----+----+----+----+----+----+----+----+----+----+----+  3459
      G   H   P   Q   L   P   G   H   A   K   P   G   T   P   A   L   E   T   L   E 3460  accacaccctgccaccctgctccaaggacgatggtttcctcaacggctcctgctca
 a    ----+----+----+----+----+----+----+----+----+----+----+----+  3519
      T   T   P   P   A   M   A   A   P   K   D   D   G   F   L   N   G   S   C   S 3520  ggcctggacgaggaggcctctggcctgagcggctacctgcctgctacaggaagagtgg
 a    ----+----+----+----+----+----+----+----+----+----+----+----+  3579
      G   L   D   E   E   A   S   G   P   E   R   P   P   A   L   L   Q   E   E   W 3580  gagacagtcatgtgaccagccgctggggggctggacctgctgacatagtggatggacagat
 a    ----+----+----+----+----+----+----+----+----+----+----+----+  3639
      E   T   V   M   *

(SEQ ID NO:59)
                                                              (SEQ ID NO:60)
```

FIG.18B hTether-R11
Made from hTether-1 by inserting Asn10-Arg11 between His9 and first Gly of linker by oligonucleotide mutagenesis with Oligo = E27309

```
       atgggGAccGCccgatgcaccggcctgctctgctgcccgtgcttagc
2287 ---+---------+---------+---------+---------+---------+--- 2346
      M  G  T  A  R  I  A  P  G  L  A  L  L  L  C  C  P  V  L  S tccgcgtacgcggtttccgaaatccagctgatgcaTAATCGTggcggagaggcgaggtg
2347 ---+---------+---------+---------+---------+---------+--- 2406
      S  A  Y  A  V  S  E  I  Q  L  M  H  N  R  G  G  G  E  V tttgaccgcctggcatgatcatcctactccgtgtcctggcgtccctcacc
2407 ---+---------+---------+---------+---------+---------+--- 2466
      F  D  R  L  G  M  I  Y  T  V  G  Y  S  V  S  L  A  S  L  T gtagctgtgctcatcctggcctttaggcggctgcactgcacgcaactacatccac
2467 ---+---------+---------+---------+---------+---------+--- 2526
      V  A  V  L  I  L  A  Y  F  R  R  L  H  C  T  R  N  Y  I  H atgcacctgttcctgtccttcatgctgcgcgcctgagcatcttcgtcaaggacgctgtg
2527 ---+---------+---------+---------+---------+---------+--- 2586
      M  H  L  F  L  S  F  M  L  R  A  V  S  I  F  V  K  D  A  V ctctactctggcgccacgcttgatgaggctgagcgcctcaccgaggagagctgcgcc
2587 ---+---------+---------+---------+---------+---------+--- 2646
      L  Y  S  G  A  T  L  D  E  A  E  R  L  T  E  E  L  R  A atcgccaggcgcccccggcttctcctttacttcctgccaccaactactcgattctggtgagggg
2647 ---+---------+---------+---------+---------+---------+--- 2706
      I  A  Q  P  P  P  A  T  A  A  G  Y  A  G  C  R  V gctgtgacctttttcctttcttttcctttcatgctttctcagagaagaagtacctgtggggc
2707 ---+---------+---------+---------+---------+---------+--- 2766
      A  V  T  F  F  L  Y  F  L  A  T  N  Y  Y  W  I  L  V  E  G ctgtacctgcacagtcttcggctgggtcttgcccgctctgtcttgtggctgtgttcagtgtcaga
2767 ---+---------+---------+---------+---------+---------+--- 2826
      L  Y  L  H  S  L  I  F  M  A  F  F  S  E  K  K  Y  L  W  G ttcacagtcttcggctgggtcttgcccgctgtcttcgtggcctgtggctgtcagtgtcaga
2827 ---+---------+---------+---------+---------+---------+--- 2886
      F  T  V  F  G  W  G  L  P  A  V  F  V  A  V  W  V  S  V  R gctaccctggccaacacgggtgctggactgagctccgggaacaaaagtggatcatc
2887 ---+---------+---------+---------+---------+---------+--- 2946
      A  T  L  A  N  T  G  C  W  D  L  S  S  G  N  K  K  W  I  I
```

FIG. 19A

FIG. 19B (SEQ ID NO:57)
(SEQ ID NO:58)

```
                           SEQUENCE LISTING

<160> NUMBER OF SEQ ID NOS: 74

<210> SEQ ID NO 1
   <211> LENGTH: 9
   <212> TYPE: PRT
   <213> ORGANISM: Homo sapiens

<400> SEQUENCE: 1

Ala Val Ser Glu Ile Gln Leu Met His
    1               5

<210> SEQ ID NO 2
   <211> LENGTH: 17
   <212> TYPE: PRT
   <213> ORGANISM: Homo sapiens

<400> SEQUENCE: 2

Leu Asn Ser Met Glu Arg Val Glu Trp Leu Arg Lys Lys Leu Gln Asp
    1               5                  10                  15

Val

<210> SEQ ID NO 3
   <211> LENGTH: 31
   <212> TYPE: PRT
   <213> ORGANISM: Artificial Sequence
   <220> FEATURE:
   <223> OTHER INFORMATION: modified PTH sequence

<400> SEQUENCE: 3

Ala Val Ser Glu Ile Gln Leu Met His Gly Gly Gly Gly Gly Leu Asn
    1               5                  10                  15

Ser Met Glu Arg Val Glu Trp Leu Arg Lys Lys Leu Gln Asp Val
               20                  25                  30

<210> SEQ ID NO 4
   <211> LENGTH: 5
   <212> TYPE: PRT
   <213> ORGANISM: Homo sapiens

<400> SEQUENCE: 4

Ala Val Ser Glu Ile
    1               5

<210> SEQ ID NO 5
   <211> LENGTH: 31
   <212> TYPE: PRT
   <213> ORGANISM: Artificial Sequence
   <220> FEATURE:
   <223> OTHER INFORMATION: modified PTH sequence
```

```
<400> SEQUENCE: 5

Ala Val Ser Glu Ile Gly Gly Gly Gly Gly Gly Gly Gly Leu Asn
1               5                   10                  15

Ser Met Glu Arg Val Glu Trp Leu Arg Lys Lys Leu Gln Asp Val
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: modified PTH sequence

<400> SEQUENCE: 6

Ala Val Ser Glu Ile Gln Leu Met His Gly Gly Gly Gly Gly Gly
1               5                   10                  15

Ser Met Glu Arg Val Glu Trp Leu Arg Lys Lys Leu Gln Asp Val
            20                  25                  30

<210> SEQ ID NO 7
<211> LENGTH: 9
<212> TYPE: PRT
<213> ORGANISM: Homo sapiens

<400> SEQUENCE: 7

Ala Val Ser Glu His Gln Leu Leu His
1               5

<210> SEQ ID NO 8
<211> LENGTH: 17
<212> TYPE: PRT
<213> ORGANISM: Homo sapiens

<400> SEQUENCE: 8

Ile Gln Asp Leu Arg Arg Arg Phe Phe Leu His His Leu Ile Ala Glu
1               5                   10                  15

Ile

<210> SEQ ID NO 9
<211> LENGTH: 31
<212> TYPE: PRT
<213> ORGANISM: Artificial Sequence
<220> FEATURE:
<223> OTHER INFORMATION: modified PTH sequence
<220> FEATURE:
<221> NAME/KEY: MOD_RES
<222> LOCATION: (31)..(31)
<223> OTHER INFORMATION: AMIDATION

<400> SEQUENCE: 9

Ala Val Ser Glu Ile Gln Leu Met His Gly Gly Gly Gly Gly Leu Asn
1               5                   10                  15

Ser Met Glu Arg Val Glu Trp Leu Arg Lys Lys Leu Gln Asp Val
            20                  25                  30

<210> SEQ ID NO 10
<211> LENGTH: 5
<212> TYPE: PRT
<213> ORGANISM: Homo sapiens

<400> SEQUENCE: 10

Ala Val Ser Glu His
1               5
```

```
<210> SEQ ID NO 11
<211> LENGTH: 31
<212> TYPE: PRT
<213> ORGANISM: Artificial Sequence
<220> FEATURE:
<223> OTHER INFORMATION: modified PTH sequence
<220> FEATURE:
<221> NAME/KEY: MOD_RES
<222> LOCATION: (31)..(31)
<223> OTHER INFORMATION: AMIDATION

<400> SEQUENCE: 11

Ala Val Ser Glu Ile Gln Leu Met His Gly Gly Gly Gly Gly Gly
 1               5                  10                  15

Ser Met Glu Arg Val Glu Trp Leu Arg Lys Lys Leu Gln Asp Val
            20                  25                  30

<210> SEQ ID NO 12
<211> LENGTH: 15
<212> TYPE: PRT
<213> ORGANISM: Homo sapiens

<400> SEQUENCE: 12

Asp Leu Arg Arg Arg Phe Phe Leu His His Leu Ile Ala Glu Ile
 1               5                  10                  15

<210> SEQ ID NO 13
<211> LENGTH: 31
<212> TYPE: PRT
<213> ORGANISM: Artificial Sequence
<220> FEATURE:
<223> OTHER INFORMATION: modified PTH sequence
<220> FEATURE:
<221> NAME/KEY: MOD_RES
<222> LOCATION: (31)..(31)
<223> OTHER INFORMATION: AMIDATION

<400> SEQUENCE: 13

Ala Val Ser Glu Ile Gly Gly Gly Gly Gly Gly Gly Gly Leu Asn
 1               5                  10                  15

Ser Met Glu Arg Val Glu Trp Leu Arg Lys Lys Leu Gln Asp Val
            20                  25                  30

<210> SEQ ID NO 14
<211> LENGTH: 93
<212> TYPE: RNA
<213> ORGANISM: Artificial Sequence
<220> FEATURE:
<223> OTHER INFORMATION: Description of Artificial Sequence: modified
      PTH sequence

<400> SEQUENCE: 14
gcuguuuccg aaauccagcu gaugcacggu ggugguggug gucugaacuc cauggaacgu    60
guugaauggc ugcguaaaaa acugcaggac guu                                  93

<210> SEQ ID NO 15
<211> LENGTH: 93
<212> TYPE: RNA
<213> ORGANISM: Artificial Sequence
<220> FEATURE:
<223> OTHER INFORMATION: Description of Artificial Sequence: modified
      PTH sequence

<400> SEQUENCE: 15
gcuguuuccg aaauccagcu gaugcacggu ggugguggug guggugguuc cauggaacgu    60
```
guugaauggc ugcguaaaaa acugcaggac guu         93

```
<210> SEQ ID NO 16
<211> LENGTH: 93
<212> TYPE: RNA
<213> ORGANISM: Artificial Sequence
<220> FEATURE:
<223> OTHER INFORMATION: Description of Artificial Sequence: modified
      PTH sequence

<400> SEQUENCE: 16
```
gcuguuuccg aaaucggugg uggugguggu ggugguggug gucugaacuc cauggaacgu         60
guugaauggc ugcguaaaaa acugcaggac guu         93

```
<210> SEQ ID NO 17
<211> LENGTH: 34
<212> TYPE: PRT
<213> ORGANISM: Homo sapiens

<400> SEQUENCE: 17
```

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe

```
<210> SEQ ID NO 18
<211> LENGTH: 34
<212> TYPE: PRT
<213> ORGANISM: Homo sapiens

<400> SEQUENCE: 18
```

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
                20                  25                  30

Thr Ala

```
<210> SEQ ID NO 19
<211> LENGTH: 37
<212> TYPE: PRT
<213> ORGANISM: Homo sapiens

<400> SEQUENCE: 19
```

His Ser Asp Gly Ile Phe Thr Asp Ser Tyr Ser Arg Tyr Arg Lys Gln
 1               5                  10                  15

Met Ala Val Lys Lys Tyr Leu Ala Ala Val Leu Gly Lys Arg Tyr Lys
                20                  25                  30

Gln Arg Val Asn Lys
            35

```
<210> SEQ ID NO 20
<211> LENGTH: 28
<212> TYPE: PRT
<213> ORGANISM: Homo sapiens

<400> SEQUENCE: 20
```

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
                20                  25

-continued

<210> SEQ ID NO 21
<211> LENGTH: 29
<212> TYPE: PRT
<213> ORGANISM: Homo sapiens

<400> SEQUENCE: 21

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg
            20                  25

<210> SEQ ID NO 22
<211> LENGTH: 27
<212> TYPE: PRT
<213> ORGANISM: Homo sapiens

<400> SEQUENCE: 22

His Ala Asp Gly Val Phe Thr Ser Asp Phe Ser Lys Leu Leu Gly Gln
 1               5                  10                  15

Leu Ser Ala Lys Lys Tyr Leu Glu Ser Leu Met
            20                  25

<210> SEQ ID NO 23
<211> LENGTH: 31
<212> TYPE: PRT
<213> ORGANISM: Homo sapiens

<400> SEQUENCE: 23

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 24
<211> LENGTH: 29
<212> TYPE: PRT
<213> ORGANISM: Homo sapiens

<400> SEQUENCE: 24

His Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr
            20                  25

<210> SEQ ID NO 25
<211> LENGTH: 42
<212> TYPE: PRT
<213> ORGANISM: Homo sapiens

<400> SEQUENCE: 25

Tyr Ala Glu Gly Thr Phe Ile Ser Asp Tyr Ser Ile Ala Met Asp Lys
 1               5                  10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 26
<211> LENGTH: 27
<212> TYPE: PRT
<213> ORGANISM: Homo sapiens -continued

```
<400> SEQUENCE: 26

His Ser Asp Gly Thr Phe Thr Ser Glu Leu Ser Arg Leu Arg Glu Gly
 1               5                  10                  15

Ala Arg Leu Gln Arg Leu Leu Gln Gly Leu Val
            20                  25

<210> SEQ ID NO 27
<211> LENGTH: 32
<212> TYPE: PRT
<213> ORGANISM: Homo sapiens

<400> SEQUENCE: 27

Cys Gly Asn Leu Ser Thr Cys Met Leu Gly Thr Tyr Thr Gln Asp Phe
 1               5                  10                  15

Asn Lys Phe His Thr Phe Pro Gln Thr Ala Ile Gly Val Gly Ala Pro
            20                  25                  30

<210> SEQ ID NO 28
<211> LENGTH: 37
<212> TYPE: PRT
<213> ORGANISM: Homo sapiens

<400> SEQUENCE: 28

Ala Cys Asn Thr Ala Thr Cys Val Thr His Arg Leu Ala Gly Leu Leu
 1               5                  10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 29
<211> LENGTH: 37
<212> TYPE: PRT
<213> ORGANISM: Homo sapiens

<400> SEQUENCE: 29

Ala Cys Asp Thr Ala Thr Cys Val Thr His Arg Leu Ala Gly Leu Leu
 1               5                  10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 30
<211> LENGTH: 37
<212> TYPE: PRT
<213> ORGANISM: Homo sapiens

<400> SEQUENCE: 30

Lys Cys Asn Thr Ala Thr Cys Ala Thr Gln Arg Leu Ala Asn Phe Leu
 1               5                  10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 31
<211> LENGTH: 36
<212> TYPE: PRT
<213> ORGANISM: Homo sapiens
```

<400> SEQUENCE: 31

Gly Cys Arg Phe Gly Thr Cys Thr Val Gln Lys Leu Ala His Gln Ile
1               5                   10                  15

Tyr Gln Phe Thr Asp Lys Asp Lys Asp Asn Val Ala Pro Arg Ser Lys
            20                  25                  30

Ile Ser Pro Gln
        35

<210> SEQ ID NO 32
<211> LENGTH: 41
<212> TYPE: PRT
<213> ORGANISM: Homo sapiens

<400> SEQUENCE: 32

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 33
<211> LENGTH: 40
<212> TYPE: PRT
<213> ORGANISM: Homo sapiens

<400> SEQUENCE: 33

Glu Glu Pro Pro Ile Ser Ile Asp Leu Ser Leu Glu Leu Leu Arg Lys
1               5                   10                  15

Met Ile Glu Ile Glu Lys Gln Glu Lys Gln Gln Ala Ala Asn
            20                  25                  30

Asn Arg Leu Leu Leu Asp Thr Ile
        35                  40

<210> SEQ ID NO 34
<211> LENGTH: 46
<212> TYPE: PRT
<213> ORGANISM: Homo sapiens

<400> SEQUENCE: 34

Thr Gly Ala Gln Ser Leu Ser Ile Val Ala Pro Leu Asp Val Leu Arg
1               5                   10                  15

Gln Arg Leu Met Asn Glu Leu Asn Arg Arg Arg Met Arg Glu Leu Gln
            20                  25                  30

Gly Ser Arg Ile Gln Gln Asn Arg Gln Leu Leu Thr Ser Ile
        35                  40                  45

<210> SEQ ID NO 35
<211> LENGTH: 63
<212> TYPE: PRT
<213> ORGANISM: Homo sapiens

<400> SEQUENCE: 35

Cys Asp Ala Thr Cys Gln Phe Arg Lys Ala Ile Asp Asp Cys Gln Lys
1               5                   10                  15

Gln Ala His His Ser Asn Val Leu Gln Thr Ser Val Gln Thr Thr Ala
            20                  25                  30

Thr Phe Thr Ser Met Asp Thr Ser Gln Leu Pro Gly Asn Ser Val Phe
        35                  40                  45

```
            Lys Glu Cys Met Lys Gln Lys Lys Glu Phe Ser Ser Gly Lys
                 50                  55                  60

<210> SEQ ID NO 36
<211> LENGTH: 1335
<212> TYPE: DNA
<213> ORGANISM: Artificial Sequence
<220> FEATURE:
<223> OTHER INFORMATION: Description of Artificial Sequence: modified
      PTH receptor sequence
<220> FEATURE:
<221> NAME/KEY: CDS
<222> LOCATION: (1)..(1332)

<400> SEQUENCE: 36 atg ggg gcc gcc cgg atc gca ccc agc ctg gcg ctc cta ctc tgc tgc        48
Met Gly Ala Ala Arg Ile Ala Pro Ser Leu Ala Leu Leu Leu Cys Cys
 1               5                  10                  15 cca gtg ctc agc tcc gcc tat gcg gcc gaa acc agc gag cac ggc gga        96
Pro Val Leu Ser Ser Ala Tyr Ala Ala Glu Thr Ser Glu His Gly Gly
             20                  25                  30 gga ggc gag gta ttt gac cgc cta ggc atg atc tac acc gtg gga tac       144
Gly Gly Glu Val Phe Asp Arg Leu Gly Met Ile Tyr Thr Val Gly Tyr
         35                  40                  45 tcc atg tct ctc gcc tcc ctc acg gtg gct gtg ctc atc ctg gcc tat       192
Ser Met Ser Leu Ala Ser Leu Thr Val Ala Val Leu Ile Leu Ala Tyr
     50                  55                  60 ttt agg cgg ctg cac tgc acg cgc aac tac atc cac atg cac atg ttc       240
Phe Arg Arg Leu His Cys Thr Arg Asn Tyr Ile His Met His Met Phe
 65                  70                  75                  80 ctg tcg ttt atg ctg cgc gcc gcg agc atc ttc gtg aag gac gct gtg       288
Leu Ser Phe Met Leu Arg Ala Ala Ser Ile Phe Val Lys Asp Ala Val
                 85                  90                  95 ctc tac tct ggc ttc acg ctg gat gag gcc gag cgc ctc aca gag gaa       336
Leu Tyr Ser Gly Phe Thr Leu Asp Glu Ala Glu Arg Leu Thr Glu Glu
            100                 105                 110 gag ttg cac atc atc gcg cag gtg cca cct ccg ccg gcc gct gcc gcc       384
Glu Leu His Ile Ile Ala Gln Val Pro Pro Pro Pro Ala Ala Ala Ala
        115                 120                 125 gta ggc tac gct ggc tgc cgc gtg gcg gtg acc ttc ttc ctc tac ttc       432
Val Gly Tyr Ala Gly Cys Arg Val Ala Val Thr Phe Phe Leu Tyr Phe
    130                 135                 140 ctg gct acc aac tac tac tgg atc ctg gtg gag ggg ctg tac ttg cac       480
Leu Ala Thr Asn Tyr Tyr Trp Ile Leu Val Glu Gly Leu Tyr Leu His
145                 150                 155                 160 agc ctc atc ttc atg gcc ttt ttc tca gag aag aag tac ctg tgg ggc       528
Ser Leu Ile Phe Met Ala Phe Phe Ser Glu Lys Lys Tyr Leu Trp Gly
                165                 170                 175 ttc acc atc ttt ggc tgg ggt cta ccg gct gtc ttc gtg gct gtg tgg       576
Phe Thr Ile Phe Gly Trp Gly Leu Pro Ala Val Phe Val Ala Val Trp
            180                 185                 190 gtc ggt gtc aga gca acc ttg gcc aac act ggg tgc tgg gat ctg agc       624
Val Gly Val Arg Ala Thr Leu Ala Asn Thr Gly Cys Trp Asp Leu Ser
        195                 200                 205 tcc ggg cac aag aag tgg atc atc cag gtg ccc atc ctg gca tct gtt       672
Ser Gly His Lys Lys Trp Ile Ile Gln Val Pro Ile Leu Ala Ser Val
    210                 215                 220 gtg ctc aac ttc atc ctt ttt atc aac atc atc cgg gtg ctt gcc act       720
Val Leu Asn Phe Ile Leu Phe Ile Asn Ile Ile Arg Val Leu Ala Thr
225                 230                 235                 240 aag ctt cgg gag acc aat gcg ggc cgg tgt gac acc agg cag cag tac       768
Lys Leu Arg Glu Thr Asn Ala Gly Arg Cys Asp Thr Arg Gln Gln Tyr
```

-continued

```
                Lys Leu Arg Glu Thr Asn Ala Gly Arg Cys Asp Thr Arg Gln Gln Tyr
                                245                 250                 255 cgg aag ctg ctc agg tcc acg ttg gtg ctc gtg ccg ctc ttt ggt gtg          816
Arg Lys Leu Leu Arg Ser Thr Leu Val Leu Val Pro Leu Phe Gly Val
            260                 265                 270 cac tac acc gtc ttc atg gcc ttg ccg tac acc gag gtc tca ggg aca          864
His Tyr Thr Val Phe Met Ala Leu Pro Tyr Thr Glu Val Ser Gly Thr
        275                 280                 285 ttg tgg cag atc cag atg cat tat gag atg ctc ttc aac tcc ttc cag          912
Leu Trp Gln Ile Gln Met His Tyr Glu Met Leu Phe Asn Ser Phe Gln
    290                 295                 300 gga ttt ttt gtt gcc atc ata tac tgt ttc tgc aat ggt gag gtg cag          960
Gly Phe Phe Val Ala Ile Ile Tyr Cys Phe Cys Asn Gly Glu Val Gln
305                 310                 315                 320 gca gag att agg aag tca tgg agc cgc tgg aca ctg gcg ttg gac ttc         1008
Ala Glu Ile Arg Lys Ser Trp Ser Arg Trp Thr Leu Ala Leu Asp Phe
                325                 330                 335 aag cgc aaa gca cga agt ggg agt agc agc tac agc tat ggc cca atg         1056
Lys Arg Lys Ala Arg Ser Gly Ser Ser Ser Tyr Ser Tyr Gly Pro Met
            340                 345                 350 gtg tct cac acg agt gtg acc aat gtg ggc ccc cgt gca gga ctc agc         1104
Val Ser His Thr Ser Val Thr Asn Val Gly Pro Arg Ala Gly Leu Ser
        355                 360                 365 ctc ccc ctc agc ccc cgc ctg cct cct gcc act acc aat ggc cac tcc         1152
Leu Pro Leu Ser Pro Arg Leu Pro Pro Ala Thr Thr Asn Gly His Ser
    370                 375                 380 cag ctg cct ggc cat gcc aag cca ggg gct cca gcc act gag act gaa         1200
Gln Leu Pro Gly His Ala Lys Pro Gly Ala Pro Ala Thr Glu Thr Glu
385                 390                 395                 400 acc cta cca gtc act atg gcg gtt ccc aag gac gat gga ttc ctt aac         1248
Thr Leu Pro Val Thr Met Ala Val Pro Lys Asp Asp Gly Phe Leu Asn
                405                 410                 415 ggc tcc tgc tca ggc ctg gat gag gag gcc tcc ggg tct gcg cgg ccg         1296
Gly Ser Cys Ser Gly Leu Asp Glu Glu Ala Ser Gly Ser Ala Arg Pro
            420                 425                 430 cct cca ttg ttg cag gaa gga tgg gaa aca gtc atg tga                     1335
Pro Pro Leu Leu Gln Glu Gly Trp Glu Thr Val Met
        435                 440
```

<210> SEQ ID NO 37
<211> LENGTH: 444
<212> TYPE: PRT
<213> ORGANISM: Artificial Sequence
<220> FEATURE:
<223> OTHER INFORMATION: Description of Artificial Sequence: modified
      PTH receptor sequence

<400> SEQUENCE: 37

```
Met Gly Ala Ala Arg Ile Ala Pro Ser Leu Ala Leu Leu Leu Cys Cys
  1               5                  10                  15

Pro Val Leu Ser Ser Ala Tyr Ala Ala Glu Thr Ser Glu His Gly Gly
              20                  25                  30

Gly Gly Glu Val Phe Asp Arg Leu Gly Met Ile Tyr Thr Val Gly Tyr
          35                  40                  45

Ser Met Ser Leu Ala Ser Leu Thr Val Ala Val Leu Ile Leu Ala Tyr
      50                  55                  60

Phe Arg Arg Leu His Cys Thr Arg Asn Tyr Ile His Met His Met Phe
 65                  70                  75                  80

Leu Ser Phe Met Leu Arg Ala Ala Ser Ile Phe Val Lys Asp Ala Val
                  85                  90                  95
```

```
Leu Tyr Ser Gly Phe Thr Leu Asp Glu Ala Glu Arg Leu Thr Glu Glu
                100                 105                 110

Glu Leu His Ile Ile Ala Gln Val Pro Pro Pro Ala Ala Ala Ala
        115                 120                 125

Val Gly Tyr Ala Gly Cys Arg Val Ala Val Thr Phe Phe Leu Tyr Phe
        130                 135                 140

Leu Ala Thr Asn Tyr Tyr Trp Ile Leu Val Glu Gly Leu Tyr Leu His
145                 150                 155                 160

Ser Leu Ile Phe Met Ala Phe Phe Ser Glu Lys Lys Tyr Leu Trp Gly
                165                 170                 175

Phe Thr Ile Phe Gly Trp Gly Leu Pro Ala Val Phe Val Ala Val Trp
                180                 185                 190

Val Gly Val Arg Ala Thr Leu Ala Asn Thr Gly Cys Trp Asp Leu Ser
        195                 200                 205

Ser Gly His Lys Lys Trp Ile Ile Gln Val Pro Ile Leu Ala Ser Val
        210                 215                 220

Val Leu Asn Phe Ile Leu Phe Ile Asn Ile Ile Arg Val Leu Ala Thr
225                 230                 235                 240

Lys Leu Arg Glu Thr Asn Ala Gly Arg Cys Asp Thr Arg Gln Gln Tyr
                245                 250                 255

Arg Lys Leu Leu Arg Ser Thr Leu Val Leu Val Pro Leu Phe Gly Val
                260                 265                 270

His Tyr Thr Val Phe Met Ala Leu Pro Tyr Thr Glu Val Ser Gly Thr
                275                 280                 285

Leu Trp Gln Ile Gln Met His Tyr Glu Met Leu Phe Asn Ser Phe Gln
        290                 295                 300

Gly Phe Phe Val Ala Ile Ile Tyr Cys Phe Cys Asn Gly Glu Val Gln
305                 310                 315                 320

Ala Glu Ile Arg Lys Ser Trp Ser Arg Trp Thr Leu Ala Leu Asp Phe
                325                 330                 335

Lys Arg Lys Ala Arg Ser Gly Ser Ser Ser Tyr Ser Tyr Gly Pro Met
                340                 345                 350

Val Ser His Thr Ser Val Thr Asn Val Gly Pro Arg Ala Gly Leu Ser
        355                 360                 365

Leu Pro Leu Ser Pro Arg Leu Pro Pro Ala Thr Thr Asn Gly His Ser
        370                 375                 380

Gln Leu Pro Gly His Ala Lys Pro Gly Ala Pro Ala Thr Glu Thr Glu
385                 390                 395                 400

Thr Leu Pro Val Thr Met Ala Val Pro Lys Asp Asp Gly Phe Leu Asn
                405                 410                 415

Gly Ser Cys Ser Gly Leu Asp Glu Glu Ala Ser Gly Ser Ala Arg Pro
                420                 425                 430

Pro Pro Leu Leu Gln Glu Gly Trp Glu Thr Val Met
        435                 440
```

<210> SEQ ID NO 38
<211> LENGTH: 1002
<212> TYPE: DNA
<213> ORGANISM: Artificial Sequence
<220> FEATURE:
<223> OTHER INFORMATION: Description of Artificial Sequence: modified PTH receptor sequence
<220> FEATURE:
<221> NAME/KEY: CDS
<222> LOCATION: (1)..(1002)

<400> SEQUENCE: 38

```
atg ggg gcc gcc cgg atc gca ccc agc ctg gcg ctc cta ctc tgc tgc          48
Met Gly Ala Ala Arg Ile Ala Pro Ser Leu Ala Leu Leu Leu Cys Cys
 1               5                  10                  15 cca gtg ctc agc tcc gcc tat gcg gcc gaa acc agc gag cac ggc gga          96
Pro Val Leu Ser Ser Ala Tyr Ala Ala Glu Thr Ser Glu His Gly Gly
             20                  25                  30 gga ggc gag gta ttt gac cgc cta ggc atg atc tac acc gtg gga tac         144
Gly Gly Glu Val Phe Asp Arg Leu Gly Met Ile Tyr Thr Val Gly Tyr
         35                  40                  45 tcc atg tct ctc gcc tcc ctc acg gtg gct gtg ctc atc ctg gcc tat         192
Ser Met Ser Leu Ala Ser Leu Thr Val Ala Val Leu Ile Leu Ala Tyr
 50                  55                  60 ttt agg cgg ctg cac tgc acg cgc aac tac atc cac atg cac atg ttc         240
Phe Arg Arg Leu His Cys Thr Arg Asn Tyr Ile His Met His Met Phe
 65                  70                  75                  80 ctg tcg ttt atg ctg cgc gcc gcg agc atc ttc gtg aag gac gct gtg         288
Leu Ser Phe Met Leu Arg Ala Ala Ser Ile Phe Val Lys Asp Ala Val
                 85                  90                  95 ctc tac tct ggc ttc acg ctg gat gag gcc gag cgc ctc aca gag gaa         336
Leu Tyr Ser Gly Phe Thr Leu Asp Glu Ala Glu Arg Leu Thr Glu Glu
            100                 105                 110 gag ttg cac atc atc gcg cag gtg cca cct ccg ccg gcc gct gcc gcc         384
Glu Leu His Ile Ile Ala Gln Val Pro Pro Pro Pro Ala Ala Ala Ala
        115                 120                 125 gta ggc tac gct ggc tgc cgc gtg gcg gtg acc ttc ttc ctc tac ttc         432
Val Gly Tyr Ala Gly Cys Arg Val Ala Val Thr Phe Phe Leu Tyr Phe
    130                 135                 140 ctg gct acc aac tac tac tgg atc ctg gtg gag ggg ctg tac ttg cac         480
Leu Ala Thr Asn Tyr Tyr Trp Ile Leu Val Glu Gly Leu Tyr Leu His
145                 150                 155                 160 agc ctc atc ttc atg gcc ttt ttc tca gag aag aag tac ctg tgg ggc         528
Ser Leu Ile Phe Met Ala Phe Phe Ser Glu Lys Lys Tyr Leu Trp Gly
                165                 170                 175 ttc acc atc ttt ggc tgg ggt cta ccg gct gtc ttc gtg gct gtg tgg         576
Phe Thr Ile Phe Gly Trp Gly Leu Pro Ala Val Phe Val Ala Val Trp
            180                 185                 190 gtc ggt gtc aga gca acc ttg gcc aac act ggg tgc tgg gat ctg agc         624
Val Gly Val Arg Ala Thr Leu Ala Asn Thr Gly Cys Trp Asp Leu Ser
        195                 200                 205 tcc ggg cac aag aag tgg atc atc cag gtg ccc atc ctg gca tct gtt         672
Ser Gly His Lys Lys Trp Ile Ile Gln Val Pro Ile Leu Ala Ser Val
    210                 215                 220 gtg ctc aac ttc atc ctt ttt atc aac atc atc cgg gtg ctt gcc act         720
Val Leu Asn Phe Ile Leu Phe Ile Asn Ile Ile Arg Val Leu Ala Thr
225                 230                 235                 240 aag ctt cgg gag acc aat gcg ggc cgg tgt gac acc agg cag cag tac         768
Lys Leu Arg Glu Thr Asn Ala Gly Arg Cys Asp Thr Arg Gln Gln Tyr
                245                 250                 255 cgg aag ctg ctc agg tcc acg ttg gtg ctc gtg ccg ctc ttt ggt gtg         816
Arg Lys Leu Leu Arg Ser Thr Leu Val Leu Val Pro Leu Phe Gly Val
            260                 265                 270 cac tac acc gtc ttc atg gcc ttg ccg tac acc gag gtc tca ggg aca         864
His Tyr Thr Val Phe Met Ala Leu Pro Tyr Thr Glu Val Ser Gly Thr
        275                 280                 285 ttg tgg cag atc cag atg cat tat gag atg ctc ttc aac tcc ttc cag         912
Leu Trp Gln Ile Gln Met His Tyr Glu Met Leu Phe Asn Ser Phe Gln
    290                 295                 300 gga ttt ttt gtt gcc atc ata tac tgt ttc tgc aat ggt gag gtg cag         960
```

```
Gly Phe Phe Val Ala Ile Ile Tyr Cys Phe Cys Asn Gly Glu Val Gln
305                 310                 315                 320 gca gag att agg aag tca tgg agc cgc tgg aca ctg gcg tag          1002
Ala Glu Ile Arg Lys Ser Trp Ser Arg Trp Thr Leu Ala
                325                 330
```

<210> SEQ ID NO 39
<211> LENGTH: 333
<212> TYPE: PRT
<213> ORGANISM: Artificial Sequence
<220> FEATURE:
<223> OTHER INFORMATION: Description of Artificial Sequence: modified
      PTH receptor sequence

<400> SEQUENCE: 39

```
Met Gly Ala Ala Arg Ile Ala Pro Ser Leu Ala Leu Leu Leu Cys Cys
 1               5                  10                  15

Pro Val Leu Ser Ser Ala Tyr Ala Ala Glu Thr Ser Glu His Gly Gly
                20                  25                  30

Gly Gly Glu Val Phe Asp Arg Leu Gly Met Ile Tyr Thr Val Gly Tyr
            35                  40                  45

Ser Met Ser Leu Ala Ser Leu Thr Val Ala Val Leu Ile Leu Ala Tyr
 50                  55                  60

Phe Arg Arg Leu His Cys Thr Arg Asn Tyr Ile His Met His Met Phe
 65                  70                  75                  80

Leu Ser Phe Met Leu Arg Ala Ala Ser Ile Phe Val Lys Asp Ala Val
                85                  90                  95

Leu Tyr Ser Gly Phe Thr Leu Asp Glu Ala Glu Arg Leu Thr Glu Glu
            100                 105                 110

Glu Leu His Ile Ile Ala Gln Val Pro Pro Pro Ala Ala Ala Ala
        115                 120                 125

Val Gly Tyr Ala Gly Cys Arg Val Ala Val Thr Phe Phe Leu Tyr Phe
130                 135                 140

Leu Ala Thr Asn Tyr Tyr Trp Ile Leu Val Glu Gly Leu Tyr Leu His
145                 150                 155                 160

Ser Leu Ile Phe Met Ala Phe Phe Ser Glu Lys Lys Tyr Leu Trp Gly
                165                 170                 175

Phe Thr Ile Phe Gly Trp Gly Leu Pro Ala Val Phe Val Ala Val Trp
            180                 185                 190

Val Gly Val Arg Ala Thr Leu Ala Asn Thr Gly Cys Trp Asp Leu Ser
        195                 200                 205

Ser Gly His Lys Lys Trp Ile Ile Gln Val Pro Ile Leu Ala Ser Val
210                 215                 220

Val Leu Asn Phe Ile Leu Phe Ile Asn Ile Ile Arg Val Leu Ala Thr
225                 230                 235                 240

Lys Leu Arg Glu Thr Asn Ala Gly Arg Cys Asp Thr Arg Gln Gln Tyr
                245                 250                 255

Arg Lys Leu Leu Arg Ser Thr Leu Val Leu Pro Leu Phe Gly Val
            260                 265                 270

His Tyr Thr Val Phe Met Ala Leu Pro Tyr Thr Glu Val Ser Gly Thr
        275                 280                 285

Leu Trp Gln Ile Gln Met His Tyr Glu Met Leu Phe Asn Ser Phe Gln
290                 295                 300

Gly Phe Phe Val Ala Ile Ile Tyr Cys Phe Cys Asn Gly Glu Val Gln
305                 310                 315                 320

Ala Glu Ile Arg Lys Ser Trp Ser Arg Trp Thr Leu Ala
                325                 330
```

-continued

<210> SEQ ID NO 40
<211> LENGTH: 975
<212> TYPE: DNA
<213> ORGANISM: Artificial Sequence
<220> FEATURE:
<223> OTHER INFORMATION: Description of Artificial Sequence: modified
     PTH receptor sequence
<220> FEATURE:
<221> NAME/KEY: CDS
<222> LOCATION: (1)..(972)

<400> SEQUENCE: 40

```
atg ggg gcc gcc cgg atc gca ccc agc ctg gcg ctc cta ctc tgc tgc      48
Met Gly Ala Ala Arg Ile Ala Pro Ser Leu Ala Leu Leu Leu Cys Cys
 1               5                  10                  15 cca gtg ctc agc tcc gca tat gcg ctg gag gta ttt gac cgc cta ggc      96
Pro Val Leu Ser Ser Ala Tyr Ala Leu Glu Val Phe Asp Arg Leu Gly
             20                  25                  30 atg atc tac acc gtg gga tac tcc atg tct ctc gcc tcc ctc acg gtg    144
Met Ile Tyr Thr Val Gly Tyr Ser Met Ser Leu Ala Ser Leu Thr Val
         35                  40                  45 gct gtg ctc atc ctg gcc tat ttt agg cgg ctg cac tgc acg cgc aac    192
Ala Val Leu Ile Leu Ala Tyr Phe Arg Arg Leu His Cys Thr Arg Asn
     50                  55                  60 tac atc cac atg cac atg ttc ctg tcg ttt atg ctg cgc gcc gcg agc    240
Tyr Ile His Met His Met Phe Leu Ser Phe Met Leu Arg Ala Ala Ser
 65                  70                  75                  80 atc ttc gtg aag gac gct gtg ctc tac tct ggc ttc acg ctg gat gag    288
Ile Phe Val Lys Asp Ala Val Leu Tyr Ser Gly Phe Thr Leu Asp Glu
                 85                  90                  95 gcc gag cgc ctc aca gag gaa gag ttg cac atc atc gcg cag gtg cca    336
Ala Glu Arg Leu Thr Glu Glu Glu Leu His Ile Ile Ala Gln Val Pro
            100                 105                 110 cct ccg ccg gcc gct gcc gcc gta ggc tac gct ggc tgc cgc gtg gcg    384
Pro Pro Pro Ala Ala Ala Ala Val Gly Tyr Ala Gly Cys Arg Val Ala
        115                 120                 125 gtg acc ttc ttc ctc tac ttc ctg gct acc aac tac tac tgg atc ctg    432
Val Thr Phe Phe Leu Tyr Phe Leu Ala Thr Asn Tyr Tyr Trp Ile Leu
    130                 135                 140 gtg gag ggg ctg tac ttg cac agc ctc atc ttc atg gcc ttt ttc tca    480
Val Glu Gly Leu Tyr Leu His Ser Leu Ile Phe Met Ala Phe Phe Ser
145                 150                 155                 160 gag aag aag tac ctg tgg ggc ttc acc atc ttt ggc tgg ggt cta ccg    528
Glu Lys Lys Tyr Leu Trp Gly Phe Thr Ile Phe Gly Trp Gly Leu Pro
                165                 170                 175 gct gtc ttc gtg gct gtg tgg gtc ggt gtc aga gca acc ttg gcc aac    576
Ala Val Phe Val Ala Val Trp Val Gly Val Arg Ala Thr Leu Ala Asn
            180                 185                 190 act ggg tgc tgg gat ctg agc tcc ggg cac aag aag tgg atc atc cag    624
Thr Gly Cys Trp Asp Leu Ser Ser Gly His Lys Lys Trp Ile Ile Gln
        195                 200                 205 gtg ccc atc ctg gca tct gtt gtg ctc aac ttc atc ctt ttt atc aac    672
Val Pro Ile Leu Ala Ser Val Val Leu Asn Phe Ile Leu Phe Ile Asn
    210                 215                 220 atc atc cgg gtg ctt gcc act aag ctt cgg gag acc aat gcg ggc cgg    720
Ile Ile Arg Val Leu Ala Thr Lys Leu Arg Glu Thr Asn Ala Gly Arg
225                 230                 235                 240 tgt gac acc agg cag cag tac cgg aag ctg ctc agg tcc acg ttg gtg    768
Cys Asp Thr Arg Gln Gln Tyr Arg Lys Leu Leu Arg Ser Thr Leu Val
                245                 250                 255
```

```
ctc gtg ccg ctc ttt ggt gtg cac tac acc gtc ttc atg gcc ttg ccg         816
Leu Val Pro Leu Phe Gly Val His Tyr Thr Val Phe Met Ala Leu Pro
        260                 265                 270 tac acc gag gtc tca ggg aca ttg tgg cag atc cag atg cat tat gag         864
Tyr Thr Glu Val Ser Gly Thr Leu Trp Gln Ile Gln Met His Tyr Glu
        275                 280                 285 atg ctc ttc aac tcc ttc cag gga ttt ttt gtt gcc atc ata tac tgt         912
Met Leu Phe Asn Ser Phe Gln Gly Phe Phe Val Ala Ile Ile Tyr Cys
        290                 295                 300 ttc tgc aat ggt gag gtg cag gca gag att agg aag tca tgg agc cgc         960
Phe Cys Asn Gly Glu Val Gln Ala Glu Ile Arg Lys Ser Trp Ser Arg
305                 310                 315                 320 tgg aca ctg gcg tag                                                     975
Trp Thr Leu Ala
```

<210> SEQ ID NO 41
<211> LENGTH: 324
<212> TYPE: PRT
<213> ORGANISM: Artificial Sequence
<220> FEATURE:
<223> OTHER INFORMATION: Description of Artificial Sequence: modified
      PTH receptor sequence

<400> SEQUENCE: 41

```
Met Gly Ala Ala Arg Ile Ala Pro Ser Leu Ala Leu Leu Leu Cys Cys
 1               5                  10                  15

Pro Val Leu Ser Ser Ala Tyr Ala Leu Glu Val Phe Asp Arg Leu Gly
            20                  25                  30

Met Ile Tyr Thr Val Gly Tyr Ser Met Ser Leu Ala Ser Leu Thr Val
        35                  40                  45

Ala Val Leu Ile Leu Ala Tyr Phe Arg Arg Leu His Cys Thr Arg Asn
    50                  55                  60

Tyr Ile His Met His Met Phe Leu Ser Phe Met Leu Arg Ala Ala Ser
65                  70                  75                  80

Ile Phe Val Lys Asp Ala Val Leu Tyr Ser Gly Phe Thr Leu Asp Glu
            85                  90                  95

Ala Glu Arg Leu Thr Glu Glu Glu Leu His Ile Ile Ala Gln Val Pro
            100                 105                 110

Pro Pro Pro Ala Ala Ala Val Gly Tyr Ala Gly Cys Arg Val Ala
        115                 120                 125

Val Thr Phe Phe Leu Tyr Phe Leu Ala Thr Asn Tyr Tyr Trp Ile Leu
    130                 135                 140

Val Glu Gly Leu Tyr Leu His Ser Leu Ile Phe Met Ala Phe Phe Ser
145                 150                 155                 160

Glu Lys Lys Tyr Leu Trp Gly Phe Thr Ile Phe Gly Trp Gly Leu Pro
                165                 170                 175

Ala Val Phe Val Ala Val Trp Val Gly Val Arg Ala Thr Leu Ala Asn
            180                 185                 190

Thr Gly Cys Trp Asp Leu Ser Ser Gly His Lys Lys Trp Ile Ile Gln
        195                 200                 205

Val Pro Ile Leu Ala Ser Val Val Leu Asn Phe Ile Leu Phe Ile Asn
    210                 215                 220

Ile Ile Arg Val Leu Ala Thr Lys Leu Arg Glu Thr Asn Ala Gly Arg
225                 230                 235                 240

Cys Asp Thr Arg Gln Gln Tyr Arg Lys Leu Leu Arg Ser Thr Leu Val
                245                 250                 255
```

```
Leu Val Pro Leu Phe Gly Val His Tyr Thr Val Phe Met Ala Leu Pro
                260                 265                 270

Tyr Thr Glu Val Ser Gly Thr Leu Trp Gln Ile Gln Met His Tyr Glu
            275                 280                 285

Met Leu Phe Asn Ser Phe Gln Gly Phe Val Ala Ile Ile Tyr Cys
        290                 295                 300

Phe Cys Asn Gly Glu Val Gln Ala Glu Ile Arg Lys Ser Trp Ser Arg
305                 310                 315                 320

Trp Thr Leu Ala

<210> SEQ ID NO 42
<211> LENGTH: 9
<212> TYPE: PRT
<213> ORGANISM: Artificial Sequence
<220> FEATURE:
<221> NAME/KEY: UNSURE
<222> LOCATION: (1)..(1)
<223> OTHER INFORMATION: May be any amino acid.
<220> FEATURE:
<221> NAME/KEY: UNSURE
<222> LOCATION: (3)..(3)
<223> OTHER INFORMATION: May be any amino acid.
<220> FEATURE:
<221> NAME/KEY: UNSURE
<222> LOCATION: (5)..(8)
<223> OTHER INFORMATION: May be any amino acid.
<220> FEATURE:
<223> OTHER INFORMATION: Description of Artificial Sequence: synthetic
      polypeptide

<400> SEQUENCE: 42

Xaa Val Xaa Glu Xaa Xaa Xaa Xaa His
  1               5

<210> SEQ ID NO 43
<211> LENGTH: 17
<212> TYPE: PRT
<213> ORGANISM: Artificial Sequence
<220> FEATURE:
<221> NAME/KEY: UNSURE
<222> LOCATION: (1)..(5)
<223> OTHER INFORMATION: May be any amino acid.
<220> FEATURE:
<221> NAME/KEY: UNSURE
<222> LOCATION: (7)..(8)
<223> OTHER INFORMATION: May be any amino acid.
<220> FEATURE:
<221> NAME/KEY: UNSURE
<222> LOCATION: (10)
<223> OTHER INFORMATION: May be any amino acid.
<220> FEATURE:
<221> NAME/KEY: UNSURE
<222> LOCATION: (12)
<223> OTHER INFORMATION: May be any amino acid.
<220> FEATURE:
<221> NAME/KEY: UNSURE
<222> LOCATION: (15)..(16)
<223> OTHER INFORMATION: May be any amino acid.
<220> FEATURE:
<223> OTHER INFORMATION: Description of Artificial Sequence: synthetic
      Polypeptide

<400> SEQUENCE: 43

Xaa Xaa Xaa Xaa Xaa Arg Xaa Xaa Trp Xaa Leu Xaa Lys Leu Xaa Xaa
  1               5                  10                  15

Val

<210> SEQ ID NO 44
<211> LENGTH: 9
```

<212> TYPE: PRT
<213> ORGANISM: Homo sapiens

<400> SEQUENCE: 44

Ser Val Ser Glu Ile Gln Leu Met His
 1               5

<210> SEQ ID NO 45
<211> LENGTH: 17
<212> TYPE: PRT
<213> ORGANISM: Homo sapiens

<400> SEQUENCE: 45

Leu Asn Ser Met Glu Arg Val Glu Trp Leu Arg Lys Lys Leu Gln
 1               5                  10                  15

Asp Val

<210> SEQ ID NO 46
<211> LENGTH: 120
<212> TYPE: DNA
<213> ORGANISM: Artificial Sequence
<220> FEATURE:
<223> OTHER INFORMATION: Description of Artificial Sequence: modified
      PTH receptor sequence
<220> FEATURE:
<221> NAME/KEY: CDS
<222> LOCATION: (1)..(120)

<400> SEQUENCE: 46 atg ggg gcc gcc cgg atc gca ccc agc ctg gcg ctc cta ctc tgc tgc        48
Met Gly Ala Ala Arg Ile Ala Pro Ser Leu Ala Leu Leu Leu Cys Cys
 1               5                  10                  15 cca gtg ctc agc tcc gca tat gcg ctg gtg gat gcg gac gat gtc ttt        96
Pro Val Leu Ser Ser Ala Tyr Ala Leu Val Asp Ala Asp Asp Val Phe
                20                  25                  30 acc aaa gag gaa cag att ttc ctg                                        120
Thr Lys Glu Glu Gln Ile Phe Leu
        35                  40

<210> SEQ ID NO 47
<211> LENGTH: 120
<212> TYPE: DNA
<213> ORGANISM: Artificial Sequence
<220> FEATURE:
<223> OTHER INFORMATION: Description of Artificial Sequence: modified
      PTH receptor sequence
<220> FEATURE:
<221> NAME/KEY: CDS
<222> LOCATION: (1)..(120)

<400> SEQUENCE: 47 aac cgg acg tgg gcc aac tac agc gag tgc ctc aag ttc atg acc aat        48
Asn Arg Thr Trp Ala Asn Tyr Ser Glu Cys Leu Lys Phe Met Thr Asn
 1               5                  10                  15 gag acc cgg gaa cgg gag gta ttt gac cgc cta ggc atg atc tac acc        96
Glu Thr Arg Glu Arg Glu Val Phe Asp Arg Leu Gly Met Ile Tyr Thr
                20                  25                  30 gtg gga tac tcc atg tct ctc gcc                                        120
Val Gly Tyr Ser Met Ser Leu Ala
        35                  40

<210> SEQ ID NO 48
<211> LENGTH: 39
<212> TYPE: RNA
<213> ORGANISM: Artificial Sequence
<220> FEATURE:

```
<223> OTHER INFORMATION: Description of Artificial Sequence: modified
      PTH receptor sequence

<400> SEQUENCE: 48 gcuguuccg  aaauccagcu  gaugcacggc  ggaggaggc                          39

<210> SEQ ID NO 49
<211> LENGTH: 99
<212> TYPE: DNA
<213> ORGANISM: Artificial Sequence
<220> FEATURE:
<223> OTHER INFORMATION: Description of Artificial Sequence: modified
      PTH receptor sequence

<400> SEQUENCE: 49
ctctgctgcc cagtgctcag ctccgcctat gcggtttccg aaatccagct gatgcacggc     60
ggaggaggcg aggtatttga ccgcctaggc atgatctac                            99

<210> SEQ ID NO 50
<211> LENGTH: 99
<212> TYPE: DNA
<213> ORGANISM: Artificial Sequence
<220> FEATURE:
<223> OTHER INFORMATION: modified PTH receptor sequence
<220> FEATURE:
<221> NAME/KEY: misc_feature
<222> LOCATION: (1)..(30)
<223> OTHER INFORMATION: flanking region
<220> FEATURE:
<221> NAME/KEY: misc_feature
<222> LOCATION: (31)..(69)
<223> OTHER INFORMATION: insert
<220> FEATURE:
<221> NAME/KEY: misc_feature
<222> LOCATION: (70)..(99)
<223> OTHER INFORMATION: flanking region
<220> FEATURE:
<221> NAME/KEY: CDS
<222> LOCATION: (1)..(99)

<400> SEQUENCE: 50 ctc tgc tgc cca gtg ctc agc tcc gcc tat gcg gtt tcc gaa atc cag       48
Leu Cys Cys Pro Val Leu Ser Ser Ala Tyr Ala Val Ser Glu Ile Gln
1               5                   10                  15 ctg atg cac ggc gga gga ggc gag gta ttt gac cgc cta ggc atg atc       96
Leu Met His Gly Gly Gly Gly Glu Val Phe Asp Arg Leu Gly Met Ile
            20                  25                  30 tac                                                                   99
Tyr

<210> SEQ ID NO 51
<211> LENGTH: 96
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 51
ctctgctgcc cagtgctcag ctccgcatat ccctacgacg tccccgacta cgccggcgga     60
ggaggcgagg tatttgaccg cctaggcatg atctac                               96

<210> SEQ ID NO 52
<211> LENGTH: 96
<212> TYPE: DNA
<213> ORGANISM: Artificial Sequence
<220> FEATURE:
```

```
<223> OTHER INFORMATION: Description of Artificial Sequence: modified
      PTH sequence
<220> FEATURE:
<221> NAME/KEY: misc_feature
<222> LOCATION: (28)..(54)
<223> OTHER INFORMATION: insert
<220> FEATURE:
<221> NAME/KEY: CDS
<222> LOCATION: (1)..(96)

<400> SEQUENCE: 52 ctc tgc tgc cca gtg ctc agc tcc gca tat ccc tac gac gtc ccc gac    48
Leu Cys Cys Pro Val Leu Ser Ser Ala Tyr Pro Tyr Asp Val Pro Asp
1               5                   10                  15 tac gcc ggc gga gga ggc gag gta ttt gac cgc cta ggc atg atc tac    96
Tyr Ala Gly Gly Gly Gly Glu Val Phe Asp Arg Leu Gly Met Ile Tyr
            20                  25                  30

<210> SEQ ID NO 53
<211> LENGTH: 40
<212> TYPE: PRT
<213> ORGANISM: Artificial Sequence
<220> FEATURE:
<223> OTHER INFORMATION: Description of Artificial Sequence: modified
      PTH sequence

<400> SEQUENCE: 53

Met Gly Ala Ala Arg Ile Ala Pro Ser Leu Ala Leu Leu Leu Cys Cys
1               5                   10                  15

Pro Val Leu Ser Ser Ala Tyr Ala Leu Val Asp Ala Asp Asp Val Phe
            20                  25                  30

Thr Lys Glu Glu Gln Ile Phe Leu
        35                  40

<210> SEQ ID NO 54
<211> LENGTH: 40
<212> TYPE: PRT
<213> ORGANISM: Artificial Sequence
<220> FEATURE:
<223> OTHER INFORMATION: Description of Artificial Sequence: modified
      PTH sequence

<400> SEQUENCE: 54

Asn Arg Thr Trp Ala Asn Tyr Ser Glu Cys Leu Lys Phe Met Thr Asn
1               5                   10                  15

Glu Thr Arg Glu Arg Glu Val Phe Asp Arg Leu Gly Met Ile Tyr Thr
            20                  25                  30

Val Gly Tyr Ser Met Ser Leu Ala
        35                  40

<210> SEQ ID NO 55
<211> LENGTH: 33
<212> TYPE: PRT
<213> ORGANISM: Artificial Sequence
<220> FEATURE:
<223> OTHER INFORMATION: Description of Artificial Sequence: modified
      PTH sequence

<400> SEQUENCE: 55

Leu Cys Cys Pro Val Leu Ser Ser Ala Tyr Ala Val Ser Glu Ile Gln
1               5                   10                  15

Leu Met His Gly Gly Gly Gly Glu Val Phe Asp Arg Leu Gly Met Ile
            20                  25                  30

Tyr
```

<210> SEQ ID NO 56
<211> LENGTH: 32
<212> TYPE: PRT
<213> ORGANISM: Artificial Sequence
<220> FEATURE:
<223> OTHER INFORMATION: Description of Artificial Sequence: modified
      PTH sequence

<400> SEQUENCE: 56

```
Leu Cys Cys Pro Val Leu Ser Ser Ala Tyr Pro Tyr Asp Val Pro Asp
 1               5                  10                  15

Tyr Ala Gly Gly Gly Gly Glu Val Phe Asp Arg Leu Gly Met Ile Tyr
             20                  25                  30
```

<210> SEQ ID NO 57
<211> LENGTH: 1380
<212> TYPE: DNA
<213> ORGANISM: Artificial Sequence
<220> FEATURE:
<223> OTHER INFORMATION: Description of Artificial Sequence: modified
      PTH receptor sequence
<220> FEATURE:
<221> NAME/KEY: CDS
<222> LOCATION: (1)..(1353)

<400> SEQUENCE: 57

```
atg ggg acc gcc cgg atc gca ccc ggc ctg gcg ctc ctg ctc tgc tgc      48
Met Gly Thr Ala Arg Ile Ala Pro Gly Leu Ala Leu Leu Leu Cys Cys
 1               5                  10                  15 ccc gtg ctc agc tcc gcg tac gcg gtt tcc gaa atc cag ctg atg cat      96
Pro Val Leu Ser Ser Ala Tyr Ala Val Ser Glu Ile Gln Leu Met His
             20                  25                  30 aat cgt ggc gga gga ggc gag gtg ttt gac cgc ctg ggc atg att tac     144
Asn Arg Gly Gly Gly Gly Glu Val Phe Asp Arg Leu Gly Met Ile Tyr
         35                  40                  45 acc gtg ggc tac tcc gtg tcc ctg gcg tcc ctc acc gta gct gtg ctc     192
Thr Val Gly Tyr Ser Val Ser Leu Ala Ser Leu Thr Val Ala Val Leu
     50                  55                  60 atc ctg gcc tac ttt agg cgg ctg cac tgc acg cgc aac tac atc cac     240
Ile Leu Ala Tyr Phe Arg Arg Leu His Cys Thr Arg Asn Tyr Ile His
 65                  70                  75                  80 atg cac ctg ttc ctg tcc ttc atg ctg cgc gcc gtg agc atc ttc gtc     288
Met His Leu Phe Leu Ser Phe Met Leu Arg Ala Val Ser Ile Phe Val
                 85                  90                  95 aag gac gct gtg ctc tac tct ggc gcc acg ctt gat gag gct gag cgc     336
Lys Asp Ala Val Leu Tyr Ser Gly Ala Thr Leu Asp Glu Ala Glu Arg
            100                 105                 110 ctc acc gag gag gag ctg cgc gcc atc gcc cag gcg ccc ccg cct         384
Leu Thr Glu Glu Glu Leu Arg Ala Ile Ala Gln Ala Pro Pro Pro
        115                 120                 125 gcc acc gcc gct gcc ggc tac gcg ggc tgc agg gtg gct gtg acc ttc     432
Ala Thr Ala Ala Ala Gly Tyr Ala Gly Cys Arg Val Ala Val Thr Phe
    130                 135                 140 ttc ctt tac ttc ctg gcc acc aac tac tac tgg att ctg gtg gag ggg     480
Phe Leu Tyr Phe Leu Ala Thr Asn Tyr Tyr Trp Ile Leu Val Glu Gly
145                 150                 155                 160 ctg tac ctg cac agc ctc atc ttc atg gcc ttc ttc tca gag aag aag     528
Leu Tyr Leu His Ser Leu Ile Phe Met Ala Phe Phe Ser Glu Lys Lys
                165                 170                 175 tac ctg tgg ggc ttc aca gtc ttc ggc tgg ggt ctg ccc gct gtc ttc     576
Tyr Leu Trp Gly Phe Thr Val Phe Gly Trp Gly Leu Pro Ala Val Phe
            180                 185                 190
```

| | | | | | | | | | | | | | | |
|---|---|---|---|---|---|---|---|---|---|---|---|---|---|---|
| gtg | gct | gtg | tgg | gtc | agt | gtc | aga | gct | acc | ctg | gcc | aac | acc | ggg | tgc | 624 |
| Val | Ala | Val | Trp | Val | Ser | Val | Arg | Ala | Thr | Leu | Ala | Asn | Thr | Gly | Cys | |
| | | 195 | | | | 200 | | | | | 205 | | | | | |

```
gtg gct gtg tgg gtc agt gtc aga gct acc ctg gcc aac acc ggg tgc      624
Val Ala Val Trp Val Ser Val Arg Ala Thr Leu Ala Asn Thr Gly Cys
        195                 200                 205 tgg gac ttg agc tcc ggg aac aaa aag tgg atc atc cag gtg ccc atc      672
Trp Asp Leu Ser Ser Gly Asn Lys Lys Trp Ile Ile Gln Val Pro Ile
210                 215                 220 ctg gcc tcc att gtg ctc aac ttc atc ctc ttc atc aat atc gtc cgg      720
Leu Ala Ser Ile Val Leu Asn Phe Ile Leu Phe Ile Asn Ile Val Arg
225                 230                 235                 240 gtg ctc gcc acc aag ctg cgg gag acc aac gcc ggc cgg tgt gac aca      768
Val Leu Ala Thr Lys Leu Arg Glu Thr Asn Ala Gly Arg Cys Asp Thr
                245                 250                 255 cgg cag cag tac cgg aag ctg ctc aaa tcc acg ctg gtg ctc atg ccc      816
Arg Gln Gln Tyr Arg Lys Leu Leu Lys Ser Thr Leu Val Leu Met Pro
            260                 265                 270 ctc ttt ggc gtc cac tac att gtc ttc atg gcc aca cca tac acc gag      864
Leu Phe Gly Val His Tyr Ile Val Phe Met Ala Thr Pro Tyr Thr Glu
        275                 280                 285 gtc tca ggg acg ctc tgg caa gtc cag atg cac tat gag atg ctc ttc      912
Val Ser Gly Thr Leu Trp Gln Val Gln Met His Tyr Glu Met Leu Phe
290                 295                 300 aac tcc ttc cag gga ttt ttt gtc gca atc ata tac tgt ttc tgc aat      960
Asn Ser Phe Gln Gly Phe Phe Val Ala Ile Ile Tyr Cys Phe Cys Asn
305                 310                 315                 320 ggc gag gta caa gct gag atc aag aaa tct tgg agc cgc tgg aca ctg     1008
Gly Glu Val Gln Ala Glu Ile Lys Lys Ser Trp Ser Arg Trp Thr Leu
                325                 330                 335 gca ctg gac ttc aag cga aag gca cgc agc ggg agc agc agc tat agc     1056
Ala Leu Asp Phe Lys Arg Lys Ala Arg Ser Gly Ser Ser Ser Tyr Ser
            340                 345                 350 tac ggc ccc atg gtg tcc cac aca agt gtg acc aat gtc ggc ccc cgt     1104
Tyr Gly Pro Met Val Ser His Thr Ser Val Thr Asn Val Gly Pro Arg
        355                 360                 365 gtg gga ctc ggc ctg ccc ctc agc ccc cgc cta ctg ccc act gcc acc     1152
Val Gly Leu Gly Leu Pro Leu Ser Pro Arg Leu Leu Pro Thr Ala Thr
370                 375                 380 acc aac ggc cac cct cag ctg cct ggc cat gcc aag cca ggg acc cca     1200
Thr Asn Gly His Pro Gln Leu Pro Gly His Ala Lys Pro Gly Thr Pro
385                 390                 395                 400 gcc ctg gag acc ctc gag acc aca cca cct gcc atg gct gct ccc aag     1248
Ala Leu Glu Thr Leu Glu Thr Thr Pro Pro Ala Met Ala Ala Pro Lys
                405                 410                 415 gac gat ggg ttc ctc aac ggc tcc tgc tca ggc ctg gac gag gag gcc     1296
Asp Asp Gly Phe Leu Asn Gly Ser Cys Ser Gly Leu Asp Glu Glu Ala
            420                 425                 430 tct ggg cct gag cgg cca cct gcc ctg cta cag gaa gag tgg gag aca     1344
Ser Gly Pro Glu Arg Pro Pro Ala Leu Leu Gln Glu Glu Trp Glu Thr
        435                 440                 445 gtc atg tga ccaggcgctg ggggctggac ctgctga                          1380
Val Met
    450
```

<210> SEQ ID NO 58
<211> LENGTH: 450
<212> TYPE: PRT
<213> ORGANISM: Artificial Sequence
<220> FEATURE:
<223> OTHER INFORMATION: Description of Artificial Sequence: modified
      PTH receptor sequence

<400> SEQUENCE: 58

```
Met Gly Thr Ala Arg Ile Ala Pro Gly Leu Ala Leu Leu Cys Cys
 1               5                  10                  15

Pro Val Leu Ser Ser Ala Tyr Ala Val Ser Glu Ile Gln Leu Met His
                20                  25                  30

Asn Arg Gly Gly Gly Glu Val Phe Asp Arg Leu Gly Met Ile Tyr
             35                  40                  45

Thr Val Gly Tyr Ser Val Ser Leu Ala Ser Leu Thr Val Ala Val Leu
     50                  55                  60

Ile Leu Ala Tyr Phe Arg Arg Leu His Cys Thr Arg Asn Tyr Ile His
 65                  70                  75                  80

Met His Leu Phe Leu Ser Phe Met Leu Arg Ala Val Ser Ile Phe Val
                85                  90                  95

Lys Asp Ala Val Leu Tyr Ser Gly Ala Thr Leu Asp Glu Ala Glu Arg
                100                 105                 110

Leu Thr Glu Glu Glu Leu Arg Ala Ile Ala Gln Ala Pro Pro Pro
         115                 120                 125

Ala Thr Ala Ala Ala Gly Tyr Ala Gly Cys Arg Val Ala Val Thr Phe
     130                 135                 140

Phe Leu Tyr Phe Leu Ala Thr Asn Tyr Tyr Trp Ile Leu Val Glu Gly
145                 150                 155                 160

Leu Tyr Leu His Ser Leu Ile Phe Met Ala Phe Phe Ser Glu Lys Lys
                165                 170                 175

Tyr Leu Trp Gly Phe Thr Val Phe Gly Trp Gly Leu Pro Ala Val Phe
                180                 185                 190

Val Ala Val Trp Val Ser Val Arg Ala Thr Leu Ala Asn Thr Gly Cys
                195                 200                 205

Trp Asp Leu Ser Ser Gly Asn Lys Lys Trp Ile Ile Gln Val Pro Ile
    210                 215                 220

Leu Ala Ser Ile Val Leu Asn Phe Ile Leu Phe Ile Asn Ile Val Arg
225                 230                 235                 240

Val Leu Ala Thr Lys Leu Arg Glu Thr Asn Ala Gly Arg Cys Asp Thr
                245                 250                 255

Arg Gln Gln Tyr Arg Lys Leu Leu Lys Ser Thr Leu Val Leu Met Pro
            260                 265                 270

Leu Phe Gly Val His Tyr Ile Val Phe Met Ala Thr Pro Tyr Thr Glu
            275                 280                 285

Val Ser Gly Thr Leu Trp Gln Val Gln Met His Tyr Glu Met Leu Phe
    290                 295                 300

Asn Ser Phe Gln Gly Phe Phe Val Ala Ile Ile Tyr Cys Phe Cys Asn
305                 310                 315                 320

Gly Glu Val Gln Ala Glu Ile Lys Lys Ser Trp Ser Arg Trp Thr Leu
                325                 330                 335

Ala Leu Asp Phe Lys Arg Lys Ala Arg Ser Gly Ser Ser Ser Tyr Ser
                340                 345                 350

Tyr Gly Pro Met Val Ser His Thr Ser Val Thr Asn Val Gly Pro Arg
            355                 360                 365

Val Gly Leu Gly Leu Pro Leu Ser Pro Arg Leu Leu Pro Thr Ala Thr
    370                 375                 380

Thr Asn Gly His Pro Gln Leu Pro Gly His Ala Lys Pro Gly Thr Pro
385                 390                 395                 400

Ala Leu Glu Thr Leu Glu Thr Thr Pro Ala Met Ala Ala Pro Lys
                405                 410                 415

Asp Asp Gly Phe Leu Asn Gly Ser Cys Ser Gly Leu Asp Glu Glu Ala
```

```
                    420             425             430
             Ser Gly Pro Glu Arg Pro Ala Leu Leu Gln Glu Glu Trp Glu Thr
                     435                     440                 445

Val Met
                 450

<210> SEQ ID NO 59
<211> LENGTH: 1380
<212> TYPE: DNA
<213> ORGANISM: Artificial Sequence
<220> FEATURE:
<223> OTHER INFORMATION: Description of Artificial Sequence: modified
      PTH receptor sequence
<220> FEATURE:
<221> NAME/KEY: CDS
<222> LOCATION: (28)..(1335)

<400> SEQUENCE: 59
tggatcccgc ggccctaggc ggtggcg atg ggg acc gcc cgg atc gca ccc ggc    54
                             Met Gly Thr Ala Arg Ile Ala Pro Gly
                               1               5 ctg gcg ctc ctg ctc tgc tgc ccc gtg ctc agc tcc gca tat gag gtg     102
Leu Ala Leu Leu Leu Cys Cys Pro Val Leu Ser Ser Ala Tyr Glu Val
 10              15                  20                  25 ttt gac cgc ctg ggc atg att tac acc gtg ggc tac tcc gtg tcc ctg     150
Phe Asp Arg Leu Gly Met Ile Tyr Thr Val Gly Tyr Ser Val Ser Leu
                 30                  35                  40 gcg tcc ctc acc gta gct gtg ctc atc ctg gcc tac ttt agg cgg ctg     198
Ala Ser Leu Thr Val Ala Val Leu Ile Leu Ala Tyr Phe Arg Arg Leu
             45                  50                  55 cac tgc acg cgc aac tac atc cac atg cac ctg ttc ctg tcc ttc atg     246
His Cys Thr Arg Asn Tyr Ile His Met His Leu Phe Leu Ser Phe Met
         60                  65                  70 ctg cgc gcc gtg agc atc ttc gtc aag gac gct gtg ctc tac tct ggc     294
Leu Arg Ala Val Ser Ile Phe Val Lys Asp Ala Val Leu Tyr Ser Gly
     75                  80                  85 gcc acg ctt gat gag gct gag cgc ctc acc gag gag gag ctg cgc gcc     342
Ala Thr Leu Asp Glu Ala Glu Arg Leu Thr Glu Glu Glu Leu Arg Ala
 90                  95                 100                 105 atc gcc cag gcg ccc ccg ccg cct gcc acc gcc gct gcc ggc tac gcg     390
Ile Ala Gln Ala Pro Pro Pro Pro Ala Thr Ala Ala Ala Gly Tyr Ala
                 110                 115                 120 ggc tgc agg gtg gct gtg acc ttc ttc ctt tac ttc ctg gcc acc aac     438
Gly Cys Arg Val Ala Val Thr Phe Phe Leu Tyr Phe Leu Ala Thr Asn
             125                 130                 135 tac tac tgg att ctg gtg gag ggg ctg tac ctg cac agc ctc atc ttc     486
Tyr Tyr Trp Ile Leu Val Glu Gly Leu Tyr Leu His Ser Leu Ile Phe
         140                 145                 150 atg gcc ttc ttc tca gag aag aag tac ctg tgg ggc ttc aca gtc ttc     534
Met Ala Phe Phe Ser Glu Lys Lys Tyr Leu Trp Gly Phe Thr Val Phe
     155                 160                 165 ggc tgg ggt ctg ccc gct gtc ttc gtg gct gtg tgg gtc agt gtc aga     582
Gly Trp Gly Leu Pro Ala Val Phe Val Ala Val Trp Val Ser Val Arg
170                 175                 180                 185 gct acc ctg gcc aac acc ggg tgc tgg gac ttg agc tcc ggg aac aaa     630
Ala Thr Leu Ala Asn Thr Gly Cys Trp Asp Leu Ser Ser Gly Asn Lys
                 190                 195                 200 aag tgg atc atc cag gtg ccc atc ctg gcc tcc att gtg ctc aac ttc     678
Lys Trp Ile Ile Gln Val Pro Ile Leu Ala Ser Ile Val Leu Asn Phe
             205                 210                 215 atc ctc ttc atc aat atc gtc cgg gtg ctc gcc acc aag ctg cgg gag     726
```

```
                                                                                 774
acc aac gcc ggc cgg tgt gac aca cgg cag cag tac cgg aag ctg ctc
Thr Asn Ala Gly Arg Cys Asp Thr Arg Gln Gln Tyr Arg Lys Leu Leu
        235                 240                 245

822
aaa tcc acg ctg gtg ctc atg ccc ctc ttt ggc gtc cac tac att gtc
Lys Ser Thr Leu Val Leu Met Pro Leu Phe Gly Val His Tyr Ile Val
250                 255                 260                 265

870
ttc atg gcc aca cca tac acc gag gtc tca ggg acg ctc tgg caa gtc
Phe Met Ala Thr Pro Tyr Thr Glu Val Ser Gly Thr Leu Trp Gln Val
                270                 275                 280

918
cag atg cac tat gag atg ctc ttc aac tcc ttc cag gga ttt ttt gtc
Gln Met His Tyr Glu Met Leu Phe Asn Ser Phe Gln Gly Phe Phe Val
            285                 290                 295

966
gca atc ata tac tgt ttc tgc aat ggc gag gta caa gct gag atc aag
Ala Ile Ile Tyr Cys Phe Cys Asn Gly Glu Val Gln Ala Glu Ile Lys
        300                 305                 310

1014
aaa tct tgg agc cgc tgg aca ctg gca ctg gac ttc aag cga aag gca
Lys Ser Trp Ser Arg Trp Thr Leu Ala Leu Asp Phe Lys Arg Lys Ala
315                 320                 325

1062
cgc agc ggg agc agc agc tat agc tac ggc ccc atg gtg tcc cac aca
Arg Ser Gly Ser Ser Ser Tyr Ser Tyr Gly Pro Met Val Ser His Thr
330                 335                 340                 345

1110
agt gtg acc aat gtc ggc ccc cgt gtg gga ctc ggc ctg ccc ctc agc
Ser Val Thr Asn Val Gly Pro Arg Val Gly Leu Gly Leu Pro Leu Ser
                350                 355                 360

1158
ccc cgc cta ctg ccc act gcc acc acc aac ggc cac cct cag ctg cct
Pro Arg Leu Leu Pro Thr Ala Thr Thr Asn Gly His Pro Gln Leu Pro
            365                 370                 375

1206
ggc cat gcc aag cca ggg acc cca gcc ctg gag acc ctc gag acc aca
Gly His Ala Lys Pro Gly Thr Pro Ala Leu Glu Thr Leu Glu Thr Thr
        380                 385                 390

1254
cca cct gcc atg gct gct ccc aag gac gat ggg ttc ctc aac ggc tcc
Pro Pro Ala Met Ala Ala Pro Lys Asp Asp Gly Phe Leu Asn Gly Ser
395                 400                 405

1302
tgc tca ggc ctg gac gag gag gcc tct ggg cct gag cgg cca cct gcc
Cys Ser Gly Leu Asp Glu Glu Ala Ser Gly Pro Glu Arg Pro Pro Ala
410                 415                 420                 425

1355
ctg cta cag gaa gag tgg gag aca gtc atg tga ccaggcgctg ggggctggac
Leu Leu Gln Glu Glu Trp Glu Thr Val Met
                430                 435 ctgctgacat agtggatgga cagat                                                      1380

<210> SEQ ID NO 60
<211> LENGTH: 435
<212> TYPE: PRT
<213> ORGANISM: Artificial Sequence
<220> FEATURE:
<223> OTHER INFORMATION: Description of Artificial Sequence: modified
      PTH receptor sequence

<400> SEQUENCE: 60

Met Gly Thr Ala Arg Ile Ala Pro Gly Leu Ala Leu Leu Leu Cys Cys
1               5                   10                  15

Pro Val Leu Ser Ser Ala Tyr Glu Val Phe Asp Arg Leu Gly Met Ile
                20                  25                  30

Tyr Thr Val Gly Tyr Ser Val Ser Leu Ala Ser Leu Thr Val Ala Val
            35                  40                  45

Leu Ile Leu Ala Tyr Phe Arg Arg Leu His Cys Thr Arg Asn Tyr Ile
        50                  55                  60
```

```
His Met His Leu Phe Leu Ser Phe Met Leu Arg Ala Val Ser Ile Phe
 65                  70                  75                  80

Val Lys Asp Ala Val Leu Tyr Ser Gly Ala Thr Leu Asp Glu Ala Glu
                 85                  90                  95

Arg Leu Thr Glu Glu Leu Arg Ala Ile Ala Gln Ala Pro Pro Pro Pro
            100                 105                 110

Pro Ala Thr Ala Ala Gly Tyr Ala Gly Cys Arg Val Ala Val Thr
        115                 120                 125

Phe Phe Leu Tyr Phe Leu Ala Thr Asn Tyr Tyr Trp Ile Leu Val Glu
    130                 135                 140

Gly Leu Tyr Leu His Ser Leu Ile Phe Met Ala Phe Phe Ser Glu Lys
145                 150                 155                 160

Lys Tyr Leu Trp Gly Phe Thr Val Phe Gly Trp Gly Leu Pro Ala Val
                165                 170                 175

Phe Val Ala Val Trp Val Ser Val Arg Ala Thr Leu Ala Asn Thr Gly
            180                 185                 190

Cys Trp Asp Leu Ser Ser Gly Asn Lys Lys Trp Ile Ile Gln Val Pro
        195                 200                 205

Ile Leu Ala Ser Ile Val Leu Asn Phe Ile Leu Phe Ile Asn Ile Val
    210                 215                 220

Arg Val Leu Ala Thr Lys Leu Arg Glu Thr Asn Ala Gly Arg Cys Asp
225                 230                 235                 240

Thr Arg Gln Gln Tyr Arg Lys Leu Leu Lys Ser Thr Leu Val Leu Met
                245                 250                 255

Pro Leu Phe Gly Val His Tyr Ile Val Phe Met Ala Thr Pro Tyr Thr
            260                 265                 270

Glu Val Ser Gly Thr Leu Trp Gln Val Gln Met His Tyr Glu Met Leu
        275                 280                 285

Phe Asn Ser Phe Gln Gly Phe Phe Val Ala Ile Ile Tyr Cys Phe Cys
    290                 295                 300

Asn Gly Glu Val Gln Ala Glu Ile Lys Lys Ser Trp Ser Arg Trp Thr
305                 310                 315                 320

Leu Ala Leu Asp Phe Lys Arg Lys Ala Arg Ser Gly Ser Ser Ser Tyr
                325                 330                 335

Ser Tyr Gly Pro Met Val Ser His Thr Ser Val Thr Asn Val Gly Pro
            340                 345                 350

Arg Val Gly Leu Gly Leu Pro Leu Ser Pro Arg Leu Leu Pro Thr Ala
        355                 360                 365

Thr Thr Asn Gly His Pro Gln Leu Pro Gly His Ala Lys Pro Gly Thr
    370                 375                 380

Pro Ala Leu Glu Thr Leu Glu Thr Thr Pro Pro Ala Met Ala Ala Pro
385                 390                 395                 400

Lys Asp Asp Gly Phe Leu Asn Gly Ser Cys Ser Gly Leu Asp Glu Glu
                405                 410                 415

Ala Ser Gly Pro Glu Arg Pro Pro Ala Leu Leu Gln Glu Glu Trp Glu
            420                 425                 430

Thr Val Met
        435

<210> SEQ ID NO 61
<211> LENGTH: 1363
<212> TYPE: DNA
<213> ORGANISM: Artificial Sequence
<220> FEATURE:
```

-continued

<223> OTHER INFORMATION: Description of Artificial Sequence: modified
     PTH receptor sequence
<220> FEATURE:
<221> NAME/KEY: CDS
<222> LOCATION: (1)..(1347)

<400> SEQUENCE: 61

| | | | | | | | | | | | | | | | | |
|---|---|---|---|---|---|---|---|---|---|---|---|---|---|---|---|---|
| atg | ggg | acc | gcc | cgg | atc | gca | ccc | ggc | ctg | gcg | ctc | ctg | ctc | tgc | tgc | 48 |
| Met | Gly | Thr | Ala | Arg | Ile | Ala | Pro | Gly | Leu | Ala | Leu | Leu | Leu | Cys | Cys | |
| 1 | | | | 5 | | | | | 10 | | | | | 15 | | |
| ccc | gtg | ctc | agc | tcc | gcg | tac | gcg | gtt | tcc | gaa | atc | cag | ctg | atg | cac | 96 |
| Pro | Val | Leu | Ser | Ser | Ala | Tyr | Ala | Val | Ser | Glu | Ile | Gln | Leu | Met | His | |
| | | | 20 | | | | | 25 | | | | | 30 | | | |
| ggc | gga | gga | ggc | gag | gtg | ttt | gac | cgc | ctg | ggc | atg | att | tac | acc | gtg | 144 |
| Gly | Gly | Gly | Gly | Glu | Val | Phe | Asp | Arg | Leu | Gly | Met | Ile | Tyr | Thr | Val | |
| | | 35 | | | | | 40 | | | | | 45 | | | | |
| ggc | tac | tcc | gtg | tcc | ctg | gcg | tcc | ctc | acc | gta | gct | gtg | ctc | atc | ctg | 192 |
| Gly | Tyr | Ser | Val | Ser | Leu | Ala | Ser | Leu | Thr | Val | Ala | Val | Leu | Ile | Leu | |
| | 50 | | | | | 55 | | | | | 60 | | | | | |
| gcc | tac | ttt | agg | cgg | ctg | cac | tgc | acg | cgc | aac | tac | atc | cac | atg | cac | 240 |
| Ala | Tyr | Phe | Arg | Arg | Leu | His | Cys | Thr | Arg | Asn | Tyr | Ile | His | Met | His | |
| 65 | | | | | 70 | | | | | 75 | | | | | 80 | |
| ctg | ttc | ctg | tcc | ttc | atg | ctg | cgc | gcc | gtg | agc | atc | ttc | gtc | aag | gac | 288 |
| Leu | Phe | Leu | Ser | Phe | Met | Leu | Arg | Ala | Val | Ser | Ile | Phe | Val | Lys | Asp | |
| | | | | 85 | | | | | 90 | | | | | 95 | | |
| gct | gtg | ctc | tac | tct | ggc | gcc | acg | ctt | gat | gag | gct | gag | cgc | ctc | acc | 336 |
| Ala | Val | Leu | Tyr | Ser | Gly | Ala | Thr | Leu | Asp | Glu | Ala | Glu | Arg | Leu | Thr | |
| | | | 100 | | | | | 105 | | | | | 110 | | | |
| gag | gag | gag | ctg | cgc | gcc | atc | gcc | cag | gcg | ccc | ccg | cct | gcc | acc | | 384 |
| Glu | Glu | Glu | Leu | Arg | Ala | Ile | Ala | Gln | Ala | Pro | Pro | Pro | Ala | Thr | | |
| | | 115 | | | | | 120 | | | | | 125 | | | | |
| gcc | gct | gcc | ggc | tac | gcg | ggc | tgc | agg | gtg | gct | gtg | acc | ttc | ttc | ctt | 432 |
| Ala | Ala | Ala | Gly | Tyr | Ala | Gly | Cys | Arg | Val | Ala | Val | Thr | Phe | Phe | Leu | |
| | 130 | | | | | 135 | | | | | 140 | | | | | |
| tac | ttc | ctg | gcc | acc | aac | tac | tac | tgg | att | ctg | gtg | gag | ggg | ctg | tac | 480 |
| Tyr | Phe | Leu | Ala | Thr | Asn | Tyr | Tyr | Trp | Ile | Leu | Val | Glu | Gly | Leu | Tyr | |
| 145 | | | | | 150 | | | | | 155 | | | | | 160 | |
| ctg | cac | agc | ctc | atc | ttc | atg | gcc | ttc | ttc | tca | gag | aag | aag | tac | ctg | 528 |
| Leu | His | Ser | Leu | Ile | Phe | Met | Ala | Phe | Phe | Ser | Glu | Lys | Lys | Tyr | Leu | |
| | | | | 165 | | | | | 170 | | | | | 175 | | |
| tgg | ggc | ttc | aca | gtc | ttc | ggc | tgg | ggt | ctg | ccc | gct | gtc | ttc | gtg | gct | 576 |
| Trp | Gly | Phe | Thr | Val | Phe | Gly | Trp | Gly | Leu | Pro | Ala | Val | Phe | Val | Ala | |
| | | | 180 | | | | | 185 | | | | | 190 | | | |
| gtg | tgg | gtc | agt | gtc | aga | gct | acc | ctg | gcc | aac | acc | ggg | tgc | tgg | gac | 624 |
| Val | Trp | Val | Ser | Val | Arg | Ala | Thr | Leu | Ala | Asn | Thr | Gly | Cys | Trp | Asp | |
| | | 195 | | | | | 200 | | | | | 205 | | | | |
| ttg | agc | tcc | ggg | aac | aaa | aag | tgg | atc | atc | cag | gtg | ccc | atc | ctg | gcc | 672 |
| Leu | Ser | Ser | Gly | Asn | Lys | Lys | Trp | Ile | Ile | Gln | Val | Pro | Ile | Leu | Ala | |
| | 210 | | | | | 215 | | | | | 220 | | | | | |
| tcc | att | gtg | ctc | aac | ttc | atc | ctc | ttc | atc | aat | atc | gtc | cgg | gtg | ctc | 720 |
| Ser | Ile | Val | Leu | Asn | Phe | Ile | Leu | Phe | Ile | Asn | Ile | Val | Arg | Val | Leu | |
| 225 | | | | | 230 | | | | | 235 | | | | | 240 | |
| gcc | acc | aag | ctg | cgg | gag | acc | aac | gcc | ggc | cgg | tgt | gac | aca | cgg | cag | 768 |
| Ala | Thr | Lys | Leu | Arg | Glu | Thr | Asn | Ala | Gly | Arg | Cys | Asp | Thr | Arg | Gln | |
| | | | | 245 | | | | | 250 | | | | | 255 | | |
| cag | tac | cgg | aag | ctg | ctc | aaa | tcc | acg | ctg | gtg | ctc | atg | ccc | ctc | ttt | 816 |
| Gln | Tyr | Arg | Lys | Leu | Leu | Lys | Ser | Thr | Leu | Val | Leu | Met | Pro | Leu | Phe | |
| | | | 260 | | | | | 265 | | | | | 270 | | | |
| ggc | gtc | cac | tac | att | gtc | ttc | atg | gcc | aca | cca | tac | acc | gag | gtc | tca | 864 |
| Gly | Val | His | Tyr | Ile | Val | Phe | Met | Ala | Thr | Pro | Tyr | Thr | Glu | Val | Ser | |
| | | 275 | | | | | 280 | | | | | 285 | | | | |

```
ggg acg ctc tgg caa gtc cag atg cac tat gag atg ctc ttc aac tcc      912
Gly Thr Leu Trp Gln Val Gln Met His Tyr Glu Met Leu Phe Asn Ser
    290                 295                 300 ttc cag gga ttt ttt gtc gca atc ata tac tgt ttc tgc aat ggc gag      960
Phe Gln Gly Phe Phe Val Ala Ile Ile Tyr Cys Phe Cys Asn Gly Glu
305                 310                 315                 320 gta caa gct gag atc aag aaa tct tgg agc cgc tgg aca ctg gca ctg     1008
Val Gln Ala Glu Ile Lys Lys Ser Trp Ser Arg Trp Thr Leu Ala Leu
                325                 330                 335 gac ttc aag cga aag gca cgc agc ggg agc agc agc tat agc tac ggc     1056
Asp Phe Lys Arg Lys Ala Arg Ser Gly Ser Ser Ser Tyr Ser Tyr Gly
    340                 345                 350 ccc atg gtg tcc cac aca agt gtg acc aat gtc ggc ccc cgt gtg gga     1104
Pro Met Val Ser His Thr Ser Val Thr Asn Val Gly Pro Arg Val Gly
355                 360                 365 ctc ggc ctg ccc ctc agc ccc cgc cta ctg ccc act gcc acc acc aac     1152
Leu Gly Leu Pro Leu Ser Pro Arg Leu Leu Pro Thr Ala Thr Thr Asn
    370                 375                 380 ggc cac cct cag ctg cct ggc cat gcc aag cca ggg acc cca gcc ctg     1200
Gly His Pro Gln Leu Pro Gly His Ala Lys Pro Gly Thr Pro Ala Leu
385                 390                 395                 400 gag acc ctc gag acc aca cca cct gcc atg gct gct ccc aag gac gat     1248
Glu Thr Leu Glu Thr Thr Pro Pro Ala Met Ala Ala Pro Lys Asp Asp
                405                 410                 415 ggg ttc ctc aac ggc tcc tgc tca ggc ctg gac gag gag gcc tct ggg     1296
Gly Phe Leu Asn Gly Ser Cys Ser Gly Leu Asp Glu Glu Ala Ser Gly
    420                 425                 430 cct gag cgg cca cct gcc ctg cta cag gaa gag tgg gag aca gtc atg     1344
Pro Glu Arg Pro Pro Ala Leu Leu Gln Glu Glu Trp Glu Thr Val Met
435                 440                 445 tga ccaggcgctg ggggct                                                1363

<210> SEQ ID NO 62
<211> LENGTH: 448
<212> TYPE: PRT
<213> ORGANISM: Artificial Sequence
<220> FEATURE:
<223> OTHER INFORMATION: Description of Artificial Sequence: modified
      PTH receptor sequence

<400> SEQUENCE: 62

Met Gly Thr Ala Arg Ile Ala Pro Gly Leu Ala Leu Leu Leu Cys Cys
 1               5                  10                  15

Pro Val Leu Ser Ser Ala Tyr Ala Val Ser Glu Ile Gln Leu Met His
            20                  25                  30

Gly Gly Gly Gly Glu Val Phe Asp Arg Leu Gly Met Ile Tyr Thr Val
        35                  40                  45

Gly Tyr Ser Val Ser Leu Ala Ser Leu Thr Val Ala Val Leu Ile Leu
    50                  55                  60

Ala Tyr Phe Arg Arg Leu His Cys Thr Arg Asn Tyr Ile His Met His
65                  70                  75                  80

Leu Phe Leu Ser Phe Met Leu Arg Ala Val Ser Ile Phe Val Lys Asp
                85                  90                  95

Ala Val Leu Tyr Ser Gly Ala Thr Leu Asp Glu Ala Glu Arg Leu Thr
            100                 105                 110

Glu Glu Glu Leu Arg Ala Ile Ala Gln Ala Pro Pro Pro Ala Thr
        115                 120                 125

Ala Ala Ala Gly Tyr Ala Gly Cys Arg Val Ala Val Thr Phe Phe Leu
```

```
                130             135             140
Tyr Phe Leu Ala Thr Asn Tyr Tyr Trp Ile Leu Val Glu Gly Leu Tyr
145                 150                 155                 160

Leu His Ser Leu Ile Phe Met Ala Phe Phe Ser Glu Lys Lys Tyr Leu
                165                 170                 175

Trp Gly Phe Thr Val Phe Gly Trp Gly Leu Pro Ala Val Phe Val Ala
                180                 185                 190

Val Trp Val Ser Val Arg Ala Thr Leu Ala Asn Thr Gly Cys Trp Asp
                195                 200                 205

Leu Ser Ser Gly Asn Lys Lys Trp Ile Ile Gln Val Pro Ile Leu Ala
210                 215                 220

Ser Ile Val Leu Asn Phe Ile Leu Phe Ile Asn Ile Val Arg Val Leu
225                 230                 235                 240

Ala Thr Lys Leu Arg Glu Thr Asn Ala Gly Arg Cys Asp Thr Arg Gln
                245                 250                 255

Gln Tyr Arg Lys Leu Leu Lys Ser Thr Leu Val Leu Met Pro Leu Phe
                260                 265                 270

Gly Val His Tyr Ile Val Phe Met Ala Thr Pro Tyr Thr Glu Val Ser
                275                 280                 285

Gly Thr Leu Trp Gln Val Gln Met His Tyr Glu Met Leu Phe Asn Ser
290                 295                 300

Phe Gln Gly Phe Phe Val Ala Ile Ile Tyr Cys Phe Cys Asn Gly Glu
305                 310                 315                 320

Val Gln Ala Glu Ile Lys Lys Ser Trp Ser Arg Trp Thr Leu Ala Leu
                325                 330                 335

Asp Phe Lys Arg Lys Ala Arg Ser Gly Ser Ser Ser Tyr Ser Tyr Gly
                340                 345                 350

Pro Met Val Ser His Thr Ser Val Thr Asn Val Gly Pro Arg Val Gly
                355                 360                 365

Leu Gly Leu Pro Leu Ser Pro Arg Leu Leu Pro Thr Ala Thr Thr Asn
                370                 375                 380

Gly His Pro Gln Leu Pro Gly His Ala Lys Pro Gly Thr Pro Ala Leu
385                 390                 395                 400

Glu Thr Leu Glu Thr Thr Pro Pro Ala Met Ala Ala Pro Lys Asp Asp
                405                 410                 415

Gly Phe Leu Asn Gly Ser Cys Ser Gly Leu Asp Glu Glu Ala Ser Gly
                420                 425                 430

Pro Glu Arg Pro Pro Ala Leu Leu Gln Glu Glu Trp Glu Thr Val Met
                435                 440                 445

<210> SEQ ID NO 63
<211> LENGTH: 15
<212> TYPE: PRT
<213> ORGANISM: Homo sapiens

<400> SEQUENCE: 63

Ser Met Glu Arg Val Glu Trp Leu Arg Lys Lys Leu Gln Asp Val
1               5                   10                  15

<210> SEQ ID NO 64
<211> LENGTH: 31
<212> TYPE: PRT
<213> ORGANISM: Artificial Sequence
<220> FEATURE:
<223> OTHER INFORMATION: Description of Artificial Sequence: modified
      PTH sequence
```

```
<400> SEQUENCE: 64

Ala Val Ser Glu His Gln Leu Leu His Gly Gly Gly Gly Ile Gln
 1               5                  10                  15

Asp Leu Arg Arg Arg Phe Phe Leu His His Leu Ile Ala Glu Ile
            20                  25                  30

<210> SEQ ID NO 65
<211> LENGTH: 31
<212> TYPE: PRT
<213> ORGANISM: Artificial Sequence
<220> FEATURE:
<223> OTHER INFORMATION: Description of Artificial Sequence: modified
      PTH sequence

<400> SEQUENCE: 65

Ala Val Ser Glu His Gly Gly Gly Gly Gly Gly Gly Gly Ile Gln
 1               5                  10                  15

Asp Leu Arg Arg Arg Phe Phe Leu His His Leu Ile Ala Glu Ile
            20                  25                  30

<210> SEQ ID NO 66
<211> LENGTH: 31
<212> TYPE: PRT
<213> ORGANISM: Artificial Sequence
<220> FEATURE:
<223> OTHER INFORMATION: Description of Artificial Sequence: modified
      PTH sequence

<400> SEQUENCE: 66

Ala Val Ser Glu His Gln Leu Leu His Gly Gly Gly Gly Gly Gly
 1               5                  10                  15

Asp Leu Arg Arg Arg Phe Phe Leu His His Leu Ile Ala Glu Ile
            20                  25                  30

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: modified
      PTH sequence

<400> SEQUENCE: 67

Ala Val Ser Glu Ile Gln Leu Met His Asn Leu
 1               5                  10

<210> SEQ ID NO 68
<211> LENGTH: 99
<212> TYPE: DNA
<213> ORGANISM: Artificial sequence
<220> FEATURE:
<223> OTHER INFORMATION: modified PTH sequence

<400> SEQUENCE: 68
ctctgctgcc ccgtgctcag ctccgcgtac gcggtttccg aaatccagct gatgcacggc    60
ggaggaggcg aggtgtttga ccgcctgggc atgatttac                           99

<210> SEQ ID NO 69
<211> LENGTH: 48
<212> TYPE: DNA
<213> ORGANISM: Artificial Sequence
<220> FEATURE:
<223> OTHER INFORMATION: modified PTH receptor sequence
<220> FEATURE:
<221> NAME/KEY: CDS
```

```
<222> LOCATION: (3)..(47)

<400> SEQUENCE: 69 cc gaa atc cag ctg atg cat aat cgt ggc gga gga ggc gag gtg ttt g        48
   Glu Ile Gln Leu Met His Asn Arg Gly Gly Gly Gly Glu Val Phe
   1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: modified PTH receptor sequence

<400> SEQUENCE: 70

Glu Ile Gln Leu Met His Asn Arg Gly Gly Gly Gly Glu Val Phe Asp
1               5                   10                  15

<210> SEQ ID NO 71
<211> LENGTH: 8
<212> TYPE: PRT
<213> ORGANISM: Artificial Sequence
<220> FEATURE:
<223> OTHER INFORMATION: synthetic

<400> SEQUENCE: 71

Pro Tyr Asp Val Pro Asp Tyr Ala
1               5

<210> SEQ ID NO 72
<211> LENGTH: 13
<212> TYPE: PRT
<213> ORGANISM: Artificial Sequence
<220> FEATURE:
<223> OTHER INFORMATION: modified PTH receptor sequence

<400> SEQUENCE: 72

Ala Val Ser Glu Ile Gln Leu Met His Gly Gly Gly Gly
1               5                   10

<210> SEQ ID NO 73
<211> LENGTH: 14
<212> TYPE: PRT
<213> ORGANISM: Homo sapiens

<400> SEQUENCE: 73

Ala Val Ser Glu Ile Gln Leu Met His Asn Leu Gly Lys His
1               5                   10

<210> SEQ ID NO 74
<211> LENGTH: 9
<212> TYPE: PRT
<213> ORGANISM: Rattus sp.

<400> SEQUENCE: 74

Ala Val Ser Glu Ile Gln Leu Met His
1               5
```

PTH FUNCTIONAL DOMAIN CONJUGATE PEPTIDES, DERIVATIVES THEREOF AND NOVEL TETHERED LIGAND-RECEPTOR MOLECULES

This application claims the benefit of the filing date of U.S. Provisional Application 60/114,577 filed Dec. 31, 1998. The contents of that application are incorporated herein by reference.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention is related to the fields of molecular biology, developmental biology, physiology, neurobiology, endocrinology and medicine.

2. Description of Related Art

Parathyroid hormone (PTH) is a major regulator of calcium homeostasis whose principal target cells occur in bone and kidney. Regulation of calcium concentration is necessary for the normal function of the gastrointestinal, skeletal, neurologic, neuromuscular, and cardiovascular systems. PTH synthesis and release are controlled principally by the serum calcium level; a low level stimulates and a high level suppresses both hormone synthesis and release. PTH, in turn, maintains the serum calcium level by directly or indirectly promoting calcium entry into the blood at three sites of calcium exchange: gut, bone, and kidney. PTH contributes to net gastrointestinal absorption of calcium by favoring the renal synthesis of the active form of vitamin D. PTH promotes calcium resorption from bone indirectly by stimulating differentiation of the bone-resorbing cells, osteoclasts. It also mediates at least three main effects on the kidney: stimulation of tubular calcium reabsorption, enhancement of phosphate clearance, and promotion of an increase in the enzyme that completes synthesis of the active form of vitamin D. PTH exerts these effects primarily through receptor-mediated activation of adenylate cyclase and phospholipase C.

Disruption of calcium homeostasis may produce many clinical disorders (e.g., severe bone disease, anemia, renal impairment, ulcers, myopathy, and neuropathy) and usually results from conditions that produce an alteration in the level of parathyroid hormone. Hypercalcemia is a condition that is characterized by an elevation in the serum calcium level. It is often associated with primary hyperparathyroidism in which an excess of PTH production occurs as a result of a lesion (e.g., adenoma, hyperplasia, or carcinoma) of the parathyroid glands. Another type of hypercalcemia, humoral hypercalcemia of malignancy (HHM) is the most common paraneoplastic syndrome. It appears to result in most instances from the production by tumors (e.g., squamous, renal, ovarian, or bladder carcinomas) of a class of protein hormone which shares amino acid homology with PTH. These PTH-related proteins (PTHrP) appear to mimic certain of the renal and skeletal actions of PTH and are believed to interact with the PTH receptor in these tissues. PTHrP is normally found at low levels in many tissues, including keratinocytes, brain, pituitary, parathyroid, adrenal cortex, medulla, fetal liver, osteoblast-like cells, and lactating mammary tissues. In many HHM malignancies, PTHrP is found in the circulatory system at high levels, thereby producing the elevated calcium levels associated with HHM.

The pharmacological profiles of PTH and PTHrP are nearly identical in most in vitro assay systems, and elevated blood levels of PTH (i.e., primary hyperparathyroidism) or PTHrP (i.e., HHM) have comparable effects on mineral ion homeostasis (Broadus, A. E. & Stewart, A. F., "Parathyroid hormone-related protein: Structure, processing and physiological actions," in Basic and Clinical Concepts, Bilzikian, J. P. et al., eds., Raven Press, New York (1994), pp. 259–294; Kronenberg, H. M. et al., "*Parathyroid hormone: Biosynthesis, secretion, chemistry and action*," in Handbook of Experimental Pharmacology, Mundy, G. R. & Martin, T. J., eds., Springer-Verlag, Heidelberg (1993), pp. 185–201). The similarities in the biological activities of the two ligands can be explained by their interaction with a common receptor, the PTH/PTHrP receptor, which is expressed abundantly in bone and kidney (Urena, P. et al., *Endocrinology* 134: 451–456 (1994)).

Native human parathyroid hormone is an unmodified polypeptide of 84 amino acids. It is secreted from the parathyroid glands in response to low blood calcium levels and acts on osteoblast (bone-building cells) in bone, and on tubular epithelial cells of kidney. The hormone interacts with a cell surface receptor molecule, called the PTH-1 receptor or PTH/PTHrP receptor, which is expressed by both osteoblast and renal tubular cells. PTHrP, the major cause of the humoral hypercalcemia of malignancy, also has normal functions that include roles in development. PTHrP has 141 amino acids, though variants also occur that result from alternative gene splicing mechanisms. PTHrP plays a key role in the formation of the skeleton through a process that also involves binding to the PTH-1 receptor (Karaplis, A. C., et al., *Genes and Dev.* 8:277–289 (1994) and Lanske, B., et al., *Science* 273:663–666 (1996)).

The PTH-1 receptor is homologous in primary structure to a number of other receptors that bind peptide hormones, such as secretin (Ishihara, T. et al., *EMBO J.* 10: 1635–1641 (1991)), calcitonin (Lin, H. Y. et al., *Science* 254:1022–1024 (1991)) and glucagon (Jelinek, L. J. et al., *Science* 259: 1614–1616 (1993)); together these receptors form a distinct family called receptor family B (Kolakowski, L. F., *Receptors and Channels* 2:1–7(1994)). Within this family, the PTH-1 receptor is unique, in that it binds two peptide ligands and thereby regulates two separate biological processes. A recently identified PTH receptor subtype, called the PTH-2 receptor, binds PTH but not PTHrP (Usdin, T., et al., *J. Biol. Chem.* 270:15455–15458 (1995)). This observation implied that structural differences in the PTH and PTHrP ligands determined selectivity for interaction with the PTH-2 receptor. The PTH-2 receptor has been detected by RNA methods in the brain, pancreas and vasculature, however, its biological function has not been determined (Usdin, T., et al., *J Biol. Chem.* 270:15455–15458 (1995)). It is hypothesized that the family B receptors use a common molecular mechanism to engage their own cognate peptide hormone (Bergwitz, C., et al., *J Biol. Chem.* 271:26469–26472 (1996)).

The binding of either radiolabeled PTH(1–34) or PTHrP (1–36) to the PTH-1 receptor is competitively inhibited by either unlabeled ligand (Jüppner, H. et al., *J Biol. Chem.* 263:8557–8560 (1988); Nissenson, R. A. et al, *J Biol. Chem.* 263:12866–12871 (1988)). Thus, the recognition sites for the two ligands in the PTH-1 receptor probably overlap. In both PTH and PTHrP, the 15–34 region contains the principal determinants for binding to the PTH-1 receptor.

Although these regions show only minimal sequence homology (only 3 amino acid identities), each 15–34 peptide can block the binding of either PTH(1–34) or PTHrP(1–34) to the PTH-1 receptor (Nussbaum, S. R. et al., *J Biol. Chem.* 255:10183–10187 (1980); Caulfield, M. P. et al., *Endocrinology* 127:83–87 (1990); Abou-Samra, A.-B. et al., *Endocrinology* 125:2215–2217 (1989)). Further, the amino terminal portion of each ligand is required for bioactivity, and these probably interact with the PTH-1 receptor in similar ways, since 8 of 13 of these residues are identical in PTH and PTHrP.

Both PTH and PTHrP bind to the PTH-1 receptor with affinity in the nM range; the ligand-occupied receptor transmits a "signal" across the cell membrane to intracellular effector enzymes through a mechanism that involves intermediary heterotrimeric GTP-binding proteins (G proteins). The primary intracellular effector enzyme activated by the PTH-1 receptor in response to PTH or PTHrP is adenylyl cyclase (AC). Thus, PTH induces a robust increase in the "second messenger" molecule, cyclic adenosine monophosphate (cAMP) which goes on to regulate the poorly characterized "downstream" cellular processes involved in bone-remodeling (both bone formation and bone resorption processes). In certain cell-based assay systems, PTH can stimulate effector enzymes other than AC, including phospholipase C (PLC), which results in production of inositol triphosphate ($IP_3$), diacylglycerol (DAG) and intracellular calcium ($iCa^{2+}$). The roles of these non-cAMP second messenger molecules in bone metabolism are presently unknown.

Osteoporosis is a potentially crippling skeletal disease observed in a substantial portion of the senior adult population, in pregnant women and even in juveniles. The disease is marked by diminished bone mass, decreased bone mineral density (BMD), decreased bone strength and an increased risk of bone fracture. At present, there is no effective cure for osteoporosis, though estrogen, calcitonin and the bisphosphonates, etidronate and alendronate are used to treat the disease with varying levels of success through their action to decrease bone resorption. Since parathyroid hormone regulates blood calcium and the phosphate levels, and has potent anabolic (bone-forming) effects on the skeleton, in animals (Shen, V., et al., *Calif. Tissue Int.* 50:214–220 (1992); Whitefild, J. F., et al., *Calif. Tissue Int* 56:227–231 (1995) and Whitfield, J. F., et al., *Calif. Tissue Int.* 60:26–29 (1997)) and humans (Slovik, D. M., et al., *J. Bone Miner. Res.* 1:377–381 (1986); Dempster, D. W., et al., *Endocr. Rev.* 14:690–709 (1993) and Dempster, D. W., et al., *Endocr. Rev.* 15:261 (1994)) when administered intermittently, PTH, or PTH derivatives, are prime candidates for new and effective therapies for osteoporosis.

Truncated PTH derivatives such as PTH(1–34) and PTH (1–31) are active in most assay systems and promote bone-formation (Whitfield, J. F., et al., *Calif. Tissue Int.* 56:227–231 (1995); Whitfield, J. F., et al., *Calif. Tissue Int.* 60:26–29 (1997; Slovik, D. M., et al., *J. Bone Miner. Res.* 1:377–381 (1986); Tregear, G. W., et al., *Endocrinology* 93:1349–1353 (1973); Rixon, R. H., et al., *J. Bone Miner. Res.* 9:1179–1189 (1994); Whitfield, J. F. and Morley, P., *Trends Pharmacol. Sci.* 16:372–386 (1995) and Whitfield, J. F., et al., *Calif. Tissue Int.* 58:81–87(1996)). But these peptides are still too large for efficient non-parenteral delivery and low cost. The discovery of an even smaller "minimized" version of PTH or PTHrP would be an important advance in the effort to develop new treatments for osteoporosis.

PTH and PTHrP derivatives that have amino acid substitutions or deletions in the 1–14 region usually exhibit diminished activity (Tregear, G. W., et al., *Endocrinology* 93:1349–1353 (1973); Goltzman, D., et al., *J. Biol. Chem.* 250:3199–3203 (1975); Horiuchi, N., et al., *Science* 220: 1053–1055 (1983) and Gardella, T. J., et al., *J. Biol. Chem.* 266:13141–13146 (1991)).

Several short $NH_2$-terminal PTH or PTHrP peptides have been investigated previously, but no activity was detected. For example, bPTH(1–12) was inactive in adenylyl cyclase assays performed in rat renal membranes (Rosenblatt, M., "*Parathyroid Hormone: Chemistry and Structure-Activity Relations*," in Pathobiology Annual, Ioachim, H. L., ed., Raven Press, New York (1981), pp. 53–84) and PTHrP (1–16) was inactive in AC assays performed in Chinese hamster ovary (CHO) cells expressing the cloned rat PTH-1 receptor (Azurani, A., et al, *J. Biol. Chem.* 271:14931–14936 (1996)). It has been known that residues in the 15–34 domain of PTH contribute importantly to receptor binding affinity, as the PTH(15–34) fragment binds weakly to the receptor, but this peptide does not activate AC (Naussbaum, S. R., et al., *J. Biol. Chem.* 255:10183–10187 (1980) and Gardella, T. J., et al., *Endocrinology* 132:2024–2030 (1993)).

SUMMARY OF THE INVENTION

The relatively large size of native PTH or PTHrP presents challenges to the use of these peptides as treatments for osteoporosis. In general, a protein of this size is not suitable for use as a drug, since it cannot be delivered effectively by simple methods such as nasal inhalation. Instead, injection is required, and in the case of PTH, daily, or almost daily injections would most likely be needed to achieve increases in bone formation rates. Additionally, larger peptides are technically difficult and expensive to prepare by conventional synthetic chemistry methods. Alternative methods employing recombinant DNA and cell-based expression systems are also expensive, potentially vulnerable to contamination by foreign proteins and do not circumvent the delivery problem.

Accordingly, it would be advantageous for those skilled in the art to be able to identify a small molecule analog (either peptide or non-peptide) that is based on the larger peptide and yet which still retains the desired biological activities. The activity may at first be weak relative to the intact peptide, but further optimization can lead to enhanced efficacy and potency.

The present invention relates to compound of the formula or structure $S-(L)_n-B$, wherein S is an amino-terminal signaling functional domain of PTH; L is a linker molecule present n times, where n is preferably an integer from 1–9; and B is any sequence corresponding to the carboxy-terminal functional domain of PTH(1–34) or PTHrP(1–34). A preferable embodiment comprises a B moiety that is 10–20 amino acids in length. A more preferable embodiment comprises PTH(15–31) or PTH(17–31). The compound is preferably an isolated peptide or polypeptide. This aspect of the invention also relates to peptide derivatives derived from these $S-(L)_n-B$ peptides by alteration in amino acid composition or amino acid chain length of the S and B moieties and derivatives thereof, pharmaceutically acceptable salts thereof, and — or C-derivatives thereof, are hereinafter collectively referred to as "$S-(L)_n-B$ compounds of the invention and derivatives thereof."

The invention further relates to and isolated polypeptide wherein S is X Val X Glu X X X X His (SEQ ID NO: 42), wherein X is an amino acid, L is 5–10 glycine residues, and B is X X X X X Arg X X Trp X Leu X Lys Leu X X Val (SEQ ID NO: 43), wherein X is an amino acid. The invention also related to an isolated polypeptide of claim 1, wherein S is Ser Val Ser Glu Ile Gln Leu Met His (SEQ ID NO: 44), L is 5–10 glycine residues; and B is as Leu Asn Ser Met Glu Arg Val Glu Trp Leu Arg Lys Lys Leu Gln Asp Val (SEQ ID NO: 45).

The invention is further directed to a compound or an isolated peptide for a tethered ligand/receptor, said compound or isolated peptide having the formula or structure $R_1$—S-(L)$_n$-R or S-(L)$_n$-R, wherein $R_1$ is the PTH-1 receptor signal sequence; S is an amino-terminal ligand signaling peptide; L is a linker molecule present N times, where N is a positive integer 1–10, most preferably 4, and R is PTH-1 receptor sequence or a portion of the receptor sequence.

The invention is further related to a nucleic acid sequence encoding the compound or polypeptide S-(L)$_n$-B, $R_1$—S-(L)$_n$-R or S-(L)$_n$-R.

The invention is further directed to an isolated polypeptide or a nucleic acid encoding the polypeptide of the formula S—R, wherein S is an amino-terminal signaling polypeptide; and R is a carboxy-terminal receptor polypeptide, and wherein said signaling polypeptide and said receptor polypeptide are linked to each other. A preferable embodiment of the claimed invention is directed a polypeptide wherein S is the amino-terminal signaling polypeptide X Val X Glu X X X X His, wherein X is an amino acid.

In accordance with yet a further aspect of the invention, this invention provides a novel approach to the development of agonists and antagonists of PTH-1 receptor function through the manipulation, i.e., substitution of amino acid residues, etc., of the separate functional domains of the compound S-(L)$_n$-B, either separately or in combination.

In accordance with yet a further aspect of the invention, this invention provides a method for the treatment of a patient having need of a biologically active peptide comprising administering a therapeutically effective amount of a S-(L)$_n$-B peptide, N- or C-derivatives, pharmaceutically acceptable salts thereof, and a pharmaceutically acceptable carrier.

In accordance with yet a further aspect of the invention, there is provided a method for treating a medical disorder that results from altered or excessive action of the PTH-1/PTH-2 receptor, comprising administering to a patient a therapeutically effective amount of a biologically active S-(L)$_n$-B peptide, pharmaceutically acceptable salts thereof or N- or C-derivatives thereof and a pharmaceutically acceptable carrier sufficient to inhibit activation of the PTH-1/PTH-2 receptor of said patient.

In accordance with yet a further aspect of the invention, this invention also provides a method for determining rates of bone reformation, bone resorption and/or bone remodeling comprising administering to a patient an effective amount of a labeled S-(L)$_n$-B peptide of the invention or a derivative thereof and determining the uptake of said peptide into the bone of said patient. The peptide may be labeled with a label selected from the group consisting of radiolabel, flourescent label, bioluminescent label, or chemiluminescent label. An example of a suitable radiolabel is $^{99m}$Tc.

In accordance with yet a further aspect of the invention, this invention provides novel PTH receptors useful in the development of agonists and antagonists of PTH receptor function.

The invention is further directed to a method for treating mammalian conditions characterized by decreases in bone mass, wherein said method comprises administering to a subject in need thereof an effective bone mass-increasing amount of the polypeptides of the invention. Another aspect of the invention involves treating the same condition by providing to the patient DNA encoding said peptide and expressing said peptide in vivo. Preferably the condition to be treated is osteoporosis. Administration of the polypeptide may be by any methods know to those of skill in the art preferably at an effective amount of said polypeptide from about 0.01 µg/kg/day to about 1.0 µg/kg/day.

The invention is further directed to a method of treating diseases and disorders associated with decreased Tether I activity comprising administering an effective amount of the polypeptide of the invention to a patient in need thereof.

The invention is further directed to increasing cAMP in a mammalian cell having PTH-1 receptors, comprising contacting said cell with a sufficient amount of the polypeptides of the invention to increase cAMP.

In all of the above embodiments of the invention the "S" component of the claimed polypeptides may also be used to treat the disease conditions.

Additionally, the invention is directed to a method for screening for a peptide or non-peptide PTH agonist comprising a) binding a polypeptide having the structure of formula $R_1$ —S-(L)$_n$-R or S-(L)$_n$-R, wherein: i) $R_1$ is the PTH-1 receptor signal sequence; ii) S is an amino-terminal ligand signaling peptide; iii) L is a linker molecule present n times, where n is a positive integer 1–10, most preferably 4; and iv) R is PTH-1 receptor sequence or a portion of the receptor sequence to a potential agonist; and b) isolating said potential agonist from said polypeptide. Preferably said polypeptide is Tether-1, [R11]-Tether(1–11) or rδNt. In an additional embodiment of the invention one obtains an isolated polypeptide by the above method and uses it to treat any of the above indicated conditions or one may alternatively use the S component from a preferred $R_1$—S-(L)$_n$-R or S-(L)$_n$-R polypeptide.

BRIEF DESCRIPTION OF THE FIGURES

FIG. 6. Alanine-scan of PTH(17–31). Shown are the results of competition binding analysis, expressed in $IC_{50}$ values of 15 different PTH(17–31) derivatives, each having a different amino acid of the native sequence (shown at bottom of figure) replaced by alanine. Peptides were chemically synthesized, purified and tested for ability to inhibit PTH(1–34) binding to COS-7 cells expressing the cloned human PTH-2 receptor. $IC_{50}$ is the dose of a peptide required to inhibit 50% of $^{125}I$ PTH(1–34) binding. This figure provides information relevant to bioactivities of amino acid residues in the PTH(17–31) peptide used in the invention.

FIG. 7. Presentation of the nucleic acid (SEQ ID NO:36) and amino acid sequence (SEQ ID NO:37) of the Tether-1 receptor.

Figures 8A-1, 8A-2, 8A-3:
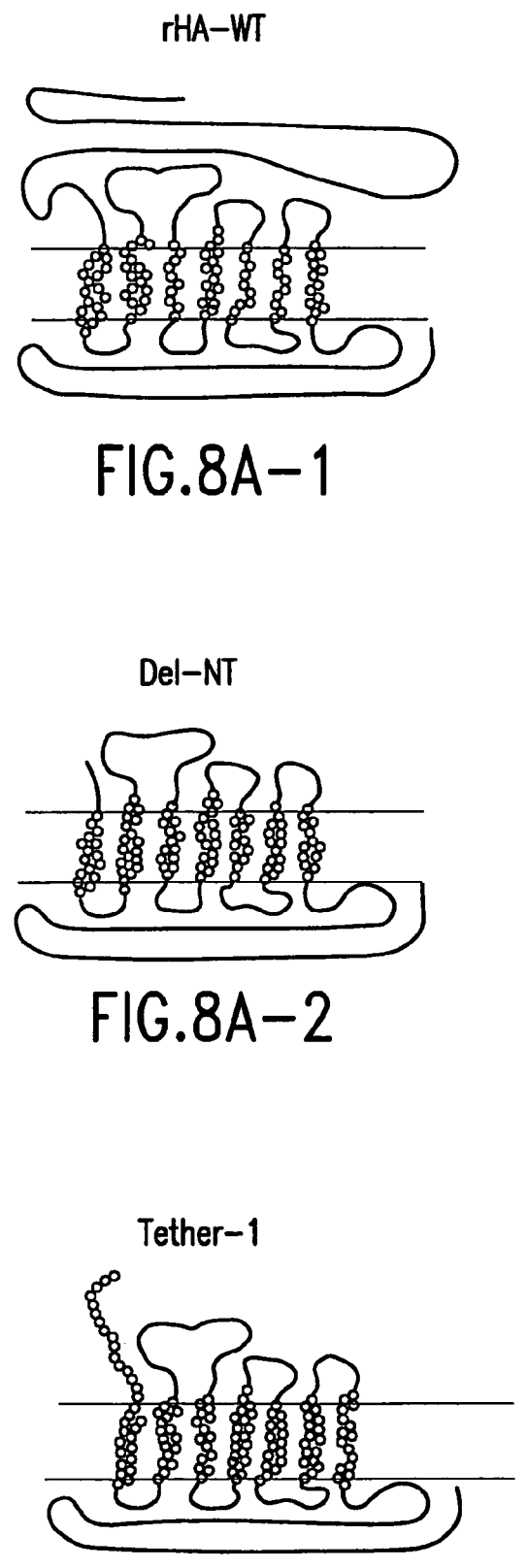

FIG. 8. A) Schematic representation of the rHA-Wt receptor (8A-1), rδNt receptor (also referred to in the application as Del-Nt, deINT or rΔNt) (8A-2), and the Tether-1 receptor (8A-3). B) Results of a cAmp accumulation assay testing the recombinant receptor molecules presented in 8A.

FIG. 9. Presentation of the nucleic acid (SEQ ID NO:38) and amino acid sequence (SEQ ID NO:39) of the Tether-1C receptor.

FIG. 10. Presentation of the nucleic acid (SEQ ID NO:40) and amino acid sequence (SEQ ID NO:41) of the rδNt/Ct receptor.

FIG. 11A–11G. Oligonucleotides and strategy for the construction of ligand/receptor chimeric molecules used in construction of chimeric rat PTH-1 receptor, rTether-1.

FIG. 11A shows the two flanking regions of the PTH receptor derived from wild-type PTH. SEQ ID NO:46 is the left side flanking region and SEQ ID NO:47 is the right side flanking region. The entire intervening sequence is not shown.

FIG. 11B shows the computer generated nucleotide sequence coding for PTH(1–9) (SEQ ID NO:48) used in the oligonucleotide.

FIG. 11C. Sequence of oligonucleotide E16631A1 (SEQ ID NO:49) used to construct rTether-1.

FIG. 11D. Flanking sequence and PTH insert(SEQ ID NO:50). The slash marks (|) indicates the flanking regions to the left and right of the PTH insert. Sequence of oligonucleotide E16631A and its protein translation. (note DNA sequence here is same as in FIG. 11C (SEQ ID NO:49).

FIG. 11E—NdeI restriction sites used in screening Tether-1 candidates.

FIG. 11F—Sequence of E16853A1 used to construct the control plasmid that contains the HA-EPITOPE TAG in place of the PTH(1–9) sequence of Tether-1.

FIG. 11G—DNA sequence and protein translation of oligo E16853A1 (note DNA sequence is same as in 11F (SEQ ID NO. 51)

FIG. 17A–17B. Nucleotide sequence (SEQ ID NO:61) and corresponding amino acid sequence (SEQ ID NO:62) of hP1R-Tether-1 (hP1R-Tether(1–9). Made from the human PTH-1 receptor by replacing Ala24 to Arg181 with Ala1 to His9 of PTH. HK-Tether-1: Sequence ID#: E20986A1 (99 nts) and its translation. Oligo to construct Tether-1 in hPTH-1 rec (HK). Join Ala-23 of rec to Val-2 of PTH(1–9)-Glyx4, -Glu-182 ctctgctgccccgtgctcagctccgcg-tacgcgGtttCCGAAAtCCAGCtGAtGCACggc-L C C P V L S S A Y A V S E I Q L M H G-ggaggaggcgaggtgtttgaccgc-ctgggcatgatctac (SEQ ID NO: 50) G G G E V F D R L G M I Y (SEQ ID NO: 55).

FIG. 18A–18B. Nucleotide sequence (SEQ ID NO:59) and corresponding amino acid sequence (SEQ ID NO:60) of hP1R-de11NT.

FIG. 19A–19B. Nucleotide sequence (SEQ ID NO:57) and corresponding amino acid sequence (SEQ ID NO:58) of hP1R-[R11]-Tether(1–11). Made from hTether-1 by inserting Asn 10-Arg11 between His9 and first Gly of linker. FIG. 19 Sequence ID#: E27309A 1. hThr-Arg 11:Insert Asn-10 and Arg11 into HK-Tether-1 *** Adds NSiI site at Met8/His9 (ATGCAt) CCGAAAtCCAGCtGAtGCAtAAtCGtg-gcggaggaggcgaggtgtttg (SEQ ID NO: 69) E I Q L M H N R G G G G E V F D(SEQ ID NO: 70).

DETAILED DESCRIPTION OF THE PREFERRED EMBODIMENTS

Figure 3B:
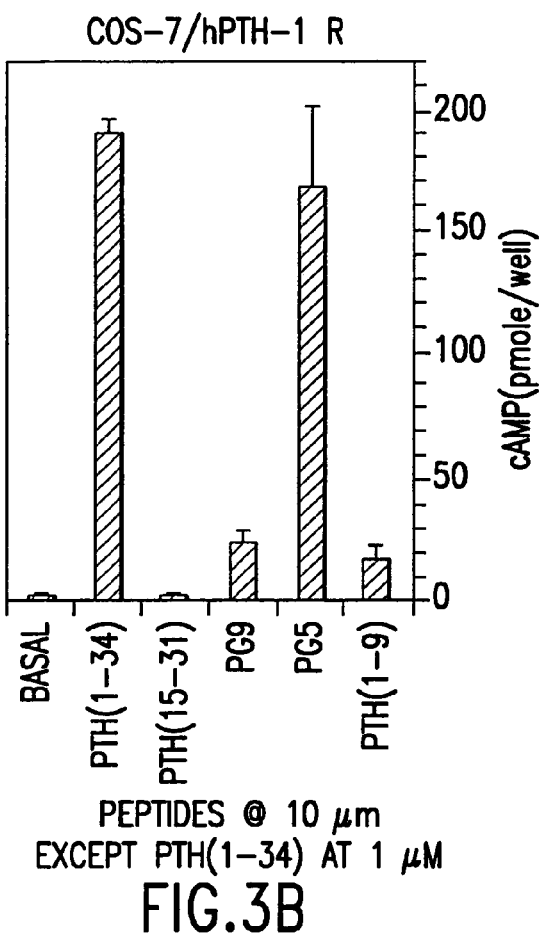
FIG. 3. Measurement of the total accumulation of cyclic AMP (cAMP) in COS cells in response to exposure to the indicated PTH peptides. A) Comparison of the accumulation of total cAMP in COS cells expressing human PTH-1 receptor (3A-1) and cells expressing a translation-stop, null PTH-1 receptor (3A-2). B) Presentation of a second experiment demonstrating the effect of PG5 and PG9 on the accumulation of cAMP in COS cells expressing the human PTH-1 receptor.

In order to provide a clearer understanding of the specification and claims, the following definitions are provided.

1. Definitions

In the description that follows, a number of terms used in recombinant DNA technology and peptide synthesis are utilized extensively. In order to provide a clear and consistent understanding of the specification and claims, including the scope to be given such terms, the following definitions are provided.

Cloning vector: A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector: A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Recombinant Host: According to the invention, a recombinant host may be any prokaryotic or eukaryotic host cell which contains the desired cloned genes on an expression vector or cloning vector. This term is also meant to include those prokaryotic or eukaryotic cells that have been genetically engineered to contain the desired gene(s) in the chromosome or genome of that organism. For examples of such hosts, see Sambrook et al., *Molecular Cloning: A Laboratory Manual*, Second Edition, Cold Spring Harbor Laboratory, Cold Spring Harbor, N.Y. (1989). Preferred recombinant hosts are eukaryotic cells transformed with the DNA construct of the invention. More specifically, mammalian cells are preferred.

Promoter: A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter. Examples of promoters include the CMV promoter (In Vitrogen, San Diego, Calif.), the SV40, MMTV, and hMTIIa promoters (U.S. Pat. No. 5,457,034), the HSV-1 4/5 promoter (U.S. Pat. No. 5,501,979), and the early intermediate HCMV promoter (WO92/17581). Also, tissue-specific enhancer elements may be employed. Additionally, such promoters may include tissue and cell-specific promoters of an organsim.

Polynucleotide: This term generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA, thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

Polypeptide: This term refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in the research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched and they may be cyclic, with or without branching. Cyclic, branched and branched cyclic polypeptides may result from post-translation natural processes or may be made by synthetic methods.

Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins-Structure and Molecular Properties,* 2nd Ed., T. E. Creighton, W. H. Freeman and Company, New York, 1993 and Wold, F., Posttranslational Protein Modifications: Perspectives and Prospects, pgs. 1–12 in *Posttranslational Covalent Modification of Proteins*, B. C. Johnson, Ed., Academic Press, New York, 1983; Seifter et al., "Analysis for protein modifications and nonprotein cofactors", *Methods in Enzymol.* 182:626–646 (1990) and Rattan et al., "Protein Synthesis: Posttranslational Modifications and Aging", *Ann NY Acad Sci* 663:48–62 (1992). The polypeptides of the invention have a free amino group at the N-terminus and a carboxy-amid at the C-terminus.

Homologous/Nonhomologous: Two nucleic acid molecules are considered to be "homologous" if their nucleotide sequences share a similarity of greater than 40%, as determined by HASH-coding algorithms (Wilber, W. J. and Lipman, D. J., *Proc. Natl. Acad. Sci.* 80:726–730 (1983)). Two nucleic acid molecules are considered to be "nonhomologous" if their nucleotide sequences share a similarity of less than 40%.

Isolated: A term meaning altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated for purposes of the present invention. Also intended as an "isolated polypeptide" or an "isolated polynucleotide" are polypeptides or polynucleotides that have been purified, partially or substantially, from a recombinant host cell or from a native source. For example, a recombinantly produced version of compounds of SEQ ID NO: 1 and derivatives thereof can be substantially purified by the one-step method described in Smith and Johnson, *Gene* 67:31–40 (1988).

By "isolated" is meant that the DNA is free of the coding sequences of those genes that, in the naturally-occurring genome of the organism (if any) from which the DNA of the invention is derived, immediately flank the gene encoding the DNA of the invention. The isolated DNA may be single-stranded or double-stranded, and may be genomic DNA, cDNA, recombinant hybrid DNA, or synthetic DNA. It may be identical to a native DNA sequence encoding compounds of SEQ ID NO: 1 and derivatives thereof, or may differ from such sequence by the deletion, addition, or substitution of one or more nucleotides. Single-stranded DNAs of the invention are generally at least 8 nucleotides long, (preferably at least 18 nucleotides long, and more preferably at least 30 nucleotides long) ranging up to full length of the DNA molecule encoding compounds of SEQ ID NO:1 and derivatives thereof (i.e., 42 nucleotides); they preferably are detectably labeled for use as hybridization probes, and may be antisense.

Isolated or purified as it refers to preparations made from biological cells or hosts should be understood to mean any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations, The procedures may include for example, but are not limited to, ammonium sulfate fractionation, gel filtration, ion exchange change chromatography, affinity chromatography, density gradient centrifugation and electrophoresis.

A preparation of DNA or protein that is "pure", or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

A cell extract that contains the DNA or protein of interest should be understood to mean a homogenate preparation or cell-free preparation obtained from cells that express the protein or contain the DNA of interest. The term "cell extract" is intended to include culture media, especially spent culture media from which the cells have been removed.

While many embodiments of the claimed invention use isolated or purified polynucleotides or polypeptides, this need not always be the case. For example, a recombinant host cell expressing the novel receptors of the invention may be used in screening assays to identify PTH agonists without being further isolating the expressed receptor proteins.

High Stringency: By "high stringency" is meant, for example, conditions such as those described for the isolation of cDNA (also see Current Protocols in Molecular Biology, John Wiley & Sons, New York (1989), hereby incorporated by reference). The DNA of the invention may be incorporated into a vector which may be provided as a purified preparation (e.g., a vector separated from the mixture of vectors which make up a library,) containing a DNA sequence encoding a peptide of the invention (e.g. compounds of SEQ ID NO:1 and derivatives thereof) and a cell or essentially homogenous population of cells (e.g., prokaryotic cells, or eukaryotic cells such as mammalian cells) which contain the vector (or the isolated DNA described above).

Identity: This term refers to a measure of the identity of nucleotide sequences or amino acid sequences. In general, the sequences are aligned so that the highest order match is obtained. "Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J. Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM J. Applied Math* 48:1073 (1988). Methods to determine identity and similarity are codified in computer programs. Preferred computer program methods to determine identity and similarity between two sequences include, but are not limited to, GCG program package (Devereux, J., et al., *Nucleic Acids Research* 12(i):387 (1984)), BLASTP, BLASTN, FASTA (Atschul, S. F., et al., *J. Molec Biol* 215:403 (1990)).

Therefore, as used herein, the term "identity" represents a comparison between a test and reference polypeptide. More specifically, reference test polypeptide is defined as any polypeptide that is 85% or more identical to a reference polypeptide. As used herein, the term at least 85% identical to refers to percent identities from 85 to 99.99 relative to the reference polypeptides. Identity at a level of 85% or more is indicative of the fact that, assuming for exemplification purposes a test and reference polynucleotide length of 100 amino acids, that no more than 15% (i.e., 15 out of 100) amino acids in the test polypeptides differ from that of the reference polypeptides. Such differences may be represented as point mutations randomly distributed over the entire length of the amino acid sequence of the invention or they may be clustered in one or more locations of varying length up to the maximum allowable 2/14 amino acid difference (approximately 85% identity). Differences are defined as amino acid substitutions, or deletions.

Fragment: A "fragment" of a molecule such as a compound of SEQ ID NO: 1 or derivative thereof is meant to refer to any polypeptide subset of these molecules.

Functional Derivative: The term "derivatives" is intended to include "variants," the "derivatives," or "chemical derivatives" of the molecule. A "variant" of a molecule such as a compound of SEQ ID NO: 1 or derivative thereof is meant to refer to a molecule substantially similar to either the entire molecule, or a fragment thereof. An "analog" of a molecule such as a compound of SEQ ID NO: 1 or derivative there of is meant to refer to a non-natural molecule substantially similar to either the SEQ ID NO: 1 molecules or fragments thereof.

A molecule is said to be "substantially similar" to another molecule if the sequence of amino acids in both molecules is substantially the same, and if both molecules possess a similar biological activity. Thus, provided that two molecules possess a similar activity, they are considered variants, derivatives, or analogs as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule 7 etc. Examples of moieties capable of mediating such effects are disclosed in *Remington's Pharmaceutical Sciences* (1980) and will be apparent to those of ordinary skill in the art.

Biological Activity of the Protein: This expression refers to the metabolic or physiologic function of compounds, for example, SEQ ID NO: 1 or derivatives thereof including similar activities or improved activities or those activities with decreased undesirable side-effects. Also included are antigenic and immunogenic activities of said compounds of, for example, SEQ ID NO: 1 or derivatives thereof.

Fusion protein: By the term "fusion protein" is intended a fused protein comprising compounds of for example, SEQ ID NO: 1 or derivatives thereof, either with or without a "selective cleavage site" linked at its N-terminus, which is in turn linked to an additional amino acid leader polypeptide sequence.

Selective cleavage site: The term "selective cleavage site" refers to an amino acid residue or residues which can be selectively cleaved with either chemicals or enzymes in a predictable manner. A selective enzyme cleavage site is an amino acid or a peptide sequence which is recognized and hydrolyzed by a proteolytic enzyme. Examples of such sites include, without limitation, trypsin or chymotrypsin cleavage sites.

Leader Sequence: By the term "leader sequence" is intended a polynucleotide sequence linked to for example, DNA encoding compounds of SEQ ID NO: 1, and expressed in host cells as a fusion protein fused to the selective cleavage site and compounds of SEQ ID NO: 1. The term "leader polypeptide" describes the expressed form of the "leader sequence" as obtained in the fusion protein.

The fusion protein, which is often insoluble and found in inclusion bodies when it is overexpressed, is purified from other bacterial protein by methods well known in the art. In a preferred embodiment, the insoluble fusion protein is centrifuged and washed after cell lysis, and resolubilized with guanidine-HCl. It can remain soluble after removal of the denaturant by dialysis. (For purification of refractile proteins, see Jones, U.S. Pat. No. 4,512,922; Olson, U.S. Pat. No. 4,518,526; and Builder et al., U.S. Pat. Nos. 4,511,502 and 4,620,948).

The recombinantly produced compounds of, for example, SEQ ID NO: 1 or derivatives thereof can be purified to be substantially free of natural contaminants from the solubilized fusion protein through the use of any of a variety of methodologies. As used herein, a compound is said to be "substantially free of natural contaminants" if it has been substantially purified from materials with which it is found following expression in bacterial or eukaryotic host cells. Compounds of SEQ ID NO: 1 or derivatives thereof may be purified through application of standard chromatographic separation technology.

Alternatively, the peptide may be purified using immunoaffinity chromatography (Rotman, A. et al., *Biochim. Biophys. Acta* 641:114–121 (1981); Sairam, M. R. J,. *Chromatog* 215:143–152 (1981); Nielsen, L. S. et al., *Biochemistry* 21:6410–6415 (1982); Vockley, J. et al., *Biochem. J.* 217:535–542 (1984); Paucha, E. et al., *J. Virol.* 51:670–681 (1984); and Chong, P. et al., *J. Virol. Meth.* 10:261–268 (1985)).

After partial or substantial purification, the fusion protein is treated enzymatically with the enzyme corresponding to the cleavage site. Alternatively, the fusion protein in its more impure state, even in refractile form, can be treated with the enzyme. If needed, the resulting mature compounds of SEQ ID NO: 1 or derivatives thereof, can be further purified. Conditions for enzymatic treatment are known to those of skill in the art.

Gene Therapy: A means of therapy directed to altering the normal pattern of gene expression of an organism. Generally, a recombinant polynucleotide is introduced into cells or tissues of the organism to effect a change in gene expression.

Host Animal: Transgenic animals, all of whose germ and somatic cells contain the DNA construct of the invention. Such transgenic animals are in general vertebrates. Preferred host animals are mammals such as non-human primates, mice, sheep, pigs, cattle, goats, guinea pigs, rodents, e.g. rats, and the like. The term Host Animal also includes animals in all stages of development, including embryonic and fetal stages.

Osteoporosis: Osteoporosis is a potentially crippling skeletal disease observed in a substantial portion of the senior adult population, in pregnant women and even in juveniles. The term osteoporosis refers to a heterogeneous group of disorders. Clinically, osteoporosis is separated into type I and type II. Type I osteoporosis occurs predominantly in middle aged women and is associated with estrogen loss at menopause, while osteoporosis type II is associated with advancing age. Patients with osteoporosis would benefit from new therapies designed to promote fracture repair, or from therapies designed to prevent or lessen the fractures associated with the disease.

2. Novel PTH Functional Domain Conjugate Peptides of the Formula $S\text{-}(L)_n\text{-}B$ In a first embodiment, the invention provides for novel PTH functional domain conjugate peptides that retain bioactivity. The new peptides correspond to the inventors' discovery and determination that amino-terminal and carboxy-terminal functional domains are present in PTH(1–34) peptide. This aspect of the invention enables the development of agonists of PTH receptor activity by selectively manipulating the biochemical properties of each functional domain, separately or in combination. The general formula of the peptide compounds of this aspect of the invention is $S\text{-}(L)_n\text{-}B$, wherein S is a amino-terminal signaling functional domain; L is a linker molecule present n times, where n is an integer from 1–9; and B is a carboxy-terminal functional domain of the peptide hormone. This aspect of the invention also relates to peptide derivatives derived from these $S\text{-}(L)_n\text{-}B$ peptides by alteration in amino acid composition or amino acid chain length of the S and B moieties.

As protein products, compounds and derivatives of the present invention are amenable to production by the technique of solution- or solid-phase peptide synthesis. The solid phase peptide synthesis technique, in particular, has been successfully applied in the production of human PTH and can be used for the production of $S\text{-}(L)_n\text{-}B$ compounds of the invention or derivatives (for guidance, see Kimura et al., supra, and see Fairwell et al., *Biochem.* 22:2691 (1983)). Success with producing human PTH on a relatively large scale has been reported by Goud et al., in *J. Bone Min. Res.* 6(8):781 (1991), incorporated herein by reference. The synthetic peptide synthesis approach generally entails the use of automated synthesizers and appropriate resin as solid phase, to which is attached the C-terminal amino acid of the desired compounds or derivatives of the invention. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984). It will be appreciated that the peptide synthesis approach is required for production of S-(L)$_n$-B compounds of the invention and derivatives and variants thereof which incorporate amino acids that are not genetically encoded.

In one specific embodiment, this invention provides a biologically active peptide useful for the design of agonists for the PTH-1 or PTH-2 receptor comprising the compound S-(L)$_n$-B, wherein S is the signaling peptide PTH(1–9)(Ala Val Ser Glu Ile Gln Leu Met His (SEQ ID NO: 1)); L is the linker molecule (Gly)$_5$; and B is a binding peptide PTH (15–31)(Leu Asn Ser Met Glu Arg Val Glu Trp Leu Arg Lys Lys Leu Gln Asp Val (SEQ ID NO:2)). The entire sequence being PG5: Ala Val Ser Glu Ile Gln Leu Met Mis Gly Gly Gly Gly Gly Leu Asn Ser Met Glu Arg Val Glu Trp Leu Arg Lys Lys Leu Gln Asp Val (SEQ ID NO:3).

In another specific embodiment, this invention provides a biologically active peptide useful for the design of agonists for the PTH1R or PTH2R receptor comprising the compound S-(L)$_n$-B, wherein S is the signaling peptide PTH (1–5)(Ala Val Ser Glu Ile (SEQ ID NO: 4)); L is the linker molecule (Gly)$_9$; and B is a binding peptide PTH(15–31) (Leu Asn Ser Met Glu Arg Val Glu Trp Leu Arg Lys Lys Leu Gln Asp Val (SEQ ID NO:2)). The entire sequence being PG9: Ala Val Ser Glu Ile Gly Gly Gly Gly Gly Gly Gly Gly Gly (Leu Asn Ser Met Glu Arg Val Glu Trp Leu Arg Lys Lys Leu Gin Asp Val (SEQ ID NO:5).

In another specific embodiment, this invention provides a biologically active peptide useful for the design of agonists for the PTH1R or PTH2R receptor comprising the compound S-(L)$_n$-B, wherein S is the signaling peptide PTH (1–9)(Ala Val Ser Glu Ile Gin Leu Met His (SEQ ID NO: 1)); L is the linker molecule (Gly)$_7$; and B is a binding peptide PTH(17–31)(Ser Met Glu Mrg Val Glu Trp Leu Mrg Lys Lys Leu Gin Asp Val (SEQ ID NO:63)). The entire sequence being PG7: Ala Val Ser Glu Ile Gin Leu Met His Gly Gly Gly Gly Gly Gly Gly Ser Met Glu Mrg Val Glu Trp Leu Mrg Lys Lys Leu Gin Asp Val (SEQ ID NO:6).

In one specific embodiment, this invention provides a biologically active peptide useful for the design of agonists for the PTH1R or PTH2R receptor comprising the compound S-(L)$_n$-B, wherein S is the signaling peptide PTHrP (1–9)(Ala Val Ser Glu His Gln Leu Leu His (SEQ ID NO: 7)); L is the linker molecule (Gly)$_5$; and B is a binding peptide PTHrP(15–31)(Ile Gln Asp Leu Arg Arg Ag Phe Phe Leu His His Leu Ile Ala Glu Ile (SEQ ID NO:8)). The entire sequence being PrPG5: Ala Val Ser Glu His Gn Leu Leu His Gly Gly Gly Gly Gly Ile Gln Asp Leu Arg Arg Arg Phe Phe Leu His His Leu Ile Ala Glu Ile (SEQ ID NO:64).

In another specific embodiment, this invention provides a biologically active peptide useful for the design of agonists for the PTH1R or PTH2R receptor comprising the compound S-(L)$_n$-B, wherein S is the signaling peptide PTHrP (1–5)(Ala Val Ser Glu His (SEQ ID NO:10)); L is the linker molecule (Gly)$_9$; and B is a binding peptide PTHrP(15–31) (Ile Gln Asp Leu Arg Arg Arg Phe Phe Leu His His Leu Ile Ala Glu Ile (SEQ ID NO:8)). The entire sequence being PrPG9: Ala Val Ser Glu His Gly Gly Gly Gly Gly Gly Gly Gly Gly (Ile Gin Asp Leu Arg Arg Arg Phe Phe Leu His His Leu Ile Ala Glu Ile (SEQ ID NO:65).

In another specific embodiment, this invention provides a biologically active peptide useful for the design of agonists for the PTH1R or PTH2R receptor comprising the compound S-(L)$_n$-B, wherein S is the signaling peptide PTHrP (1–9)(Ala Val Ser Glu His Gln Leu Leu His (SEQ ID NO:7)); L is the linker molecule (GlY)$_7$; and B is a binding peptide PTHrP(17–31)(Asp Leu Arg Arg Arg Phe Phe Leu His His Leu Ile Ala Glu Ile (SEQ ID NO:12)). The entire sequence being PrPG7: Ala Val Ser Glu His Gln Leu Leu His Gly Gly Gly Gly Gly Gly Gly Asp Leu Arg Arg Arg Phe Phe Leu His His Leu Ile Ala Glu Ile (SEQ ID NO:66).

In another specific embodiment, the S-(L)$_n$-B compound represented by PTH(1–9)-(Gly)$_5$-PTH(15–31) may be altered by amino acid substitution in the S and B peptides. Substitutions may be with either L or D sterioisomers of any selected amino acid, natural or synthetic.

Most preferred targeted sites and the preferred substitutions in the S peptide (PTH(1–9)) include the following:
1) Position 3 (serine) to alanine: shown in the alanine scan of PTH(1–4) to enhance activity.
2) Position 3 (serine) to other small amino acids (e.g. Gly, Thr, Asn, Cys), (note, bulky amino acids at 3 impair activity, as shown in Cohen, F. E., et al., *J. Biol. Chem.* 266:1997–2004 (1991).
3) Position 1 (alanine) to other small or charged amino acids (e.g. Gly, Pro. Val Thr, Asp or Lys), include L and D sterioisomers, (note, residue 1 of PTH shown to be important for activation (Tregear, G. W., et al., *Endocrinology* 93:1349–1353 (1973)).
4) Position 2 (valine) to other hydrophobic or small amino acids (e.g. Ile, Gly, Thr,) (note, residue 2 of PTH was shown earlier to be important for activation (Gardella, T. J., et al., *J. Biol. Chem.* 266:13141–13146 (1991)).
5) Position 4 (glutamate) to other charged or hydrophobic amino acids (e.g. Arg, Lys, Asp, Ile, Trp) (note, residue 4 of PTH was shown earlier to be important for activation (Gardella, T. J., et al., *J. Biol. Chem.* 266:13141–13146 (1991)).
6) Position 5 (isoleucine) to other charged or hydrophobic amino acids (e.g.
Val. Met, Trp, His, Arg, Lys, Asp,) include L and D sterioisomers, (note, residue 5 of PTH was shown earlier to be important for activation and binding (Gardella, T. J., et al., *J. Biol. Chem.* 270:6584–6588 (1995); Gardella, T., et al., *J. Biol. Chem.* 271:19888–19893 (1996)).
7) Position 6 (glutamine) to other small, charged or hydrophobic amino acids (e.g. Ala, Leu, Arg, Lys, Asp,) (note, residue 6 data of PTH was shown earlier to be important for activation (Cohen, F. B., et al., *J. Biol. Chem.* 266: 1997–2004 (1991)).

Most preferred targeted sites and the preferred substitutions in the B peptide (PTH(15–31)) include the following:
1) Position 19 (glutamate) to arginine: ER-19 substitution shown to improve binding of PTH(1–34) analogs (Gardella, T. J., et al., *J. Biol. Chem.* 270:6584–6588 (1995), Takasu et al., *Biochemistry* 38:13453–13460 (1999)).
2) Position 22 (glutamate) to alanine: EA-22 substitution shown to improve binding of PTH(17–31) (unpublished alanine scan data).

In another specific embodiment, the S-(L)$_n$-B compound represented by PTH(1–9)-(Gly)$_5$-PTH(15–31) or PTHrP (1–9)-(Gly)$_5$-PTHrP(15–31) may be altered by the substitution of any L or D amino acid stereoisomer, natural or synthetic. Such substitutions may be made in either the S or B peptide wherein no more than one amino acid is changed or substituted. The design and synthesis of such compounds are within the skill of those in the art.

In another specific embodiment, the S-(L)$_n$-B compound represented by PTH(1–9)-(Gly)$_5$-PTH(15–31) or PTHrP (1–9)-(Gly)$_5$-PTHrP(15–31) may be altered by the substitution of any L or D amino acid stereoisomer, natural or synthetic. Such substitutions may be made in either the S or B peptide wherein no more than two amino acids are changed or substituted. The design and synthesis of such compounds are within the skill of those in the aft.

In another specific embodiment, the S-(L)$_n$-B compound represented by PTH(1–9)-(Gly)$_5$-PTH(15–31) or PTHrP (1–9)-(Gly)$_5$-PTHrP(15–31) may be altered by the substitution of any L or D amino acid stereoisomer, natural or synthetic. Such substitutions may be made in either the S or B peptide wherein no more than three amino acids are changed or substituted. The design and synthesis of such compounds are within the skill of those in the art.

In another specific embodiment, the S-(L)$_n$-B compound represented by PTH(1–9)-(Gly)$_5$-PTH(15–31) or PTHrP (1–9)-(Gly)$_5$-PTHrP(15–31) may be altered by the substitution of any L or D amino acid stereoisomer, natural or synthetic. Such substitutions may be made in either the S or B peptide wherein no more than four amino acids are changed or substituted. The design and synthesis of such compounds are within the skill of those in the art.

In another specific embodiment, the S-(L)$_n$-B compound represented by PTH(1–9)-(Gly)$_5$-PTH(15–31) or PTHrP (1–9)-(Gly)$_5$-PTHrP(15–31) may be altered by the substitution of any L or D amino acid stereoisomer, natural or synthetic. Such substitutions may be made in either the S or B peptide wherein no more than five amino acids are changed or substituted. The design and synthesis of such compounds are within the skill of those in the art.

As those skilled in the art would know, other substitutions may be made in PTH(1–9)-(Gly)$_5$-PTH(15–31) or PTHrP (1–9)-(Gly)$_5$-PTHrP(15–31) such that all nine residues of the S peptide and all seventeen residues of the B peptide are substituted in pursuit of agonists of PTH receptor activity.

Additionally, another embodiment of the invention may use PTH (1–11) (Ala Val Ser Glu Ile Gln Leu Met His Asn Leu (SEQ ID NO:67) where a signaling peptide ("S") is called for.

The PTH-1 receptor is a member of the family B subgroup of G protein-coupled receptors, which also includes the receptors for calcitonin and secretin (Kolakowski, L. F., "GCRDb: A G-Protein-Coupled Receptor Database," *Receptors and Channels* 2:1–7 (1994)). Mutagenesis and crosslinking studies have indicated that multiple domains of these receptors contribute to ligand interaction, including the large amino-terminal extracellular domain, the extracellular loops and the transmembrane helices (Jüppner, H., et al., *Endocrinology* 134:879–884 (1994); Lee, C., et al., *Mol. Endo.* 9:1269–1278 (1995); Turner, P., et al., *J. Bone Min. Res.* 12(1):Abstract 121 (1997); Dautzenberg, F., et al., *Proc. Natl. Acad. Sci.* 95:4941–4946 (1998); Holtmann, M., et al., *J. Biol. Chem.* 270:14394–14398 (1995); DeAlmeida, V. and Mayo, K., *Mol Endo.* 12:750–765 (1998); Stroop, S., et al., *Biochem.* 34:1050–1057 (1994); Zhou, A., et al., *Proc. Natl. Acad. Sci. USA* 94:3644–3649 (1997); Bisello, A., et al., *J. Biol. Chem.* 273:22498–22505 (1998)). Studies using PTH/ calcitonin chimeric receptors and hybrid ligands have suggested a general topology of the interaction in which the amino-terminal extracellular domain of the receptor recognizes the carboxyl-terminal binding domain of the ligand, while the "core" region of the receptor containing the seven transmembrane helices and connecting loops recognizes the amino-terminal signaling portion of the ligand (Bergwitz, C., et al., *J. Biol. Chem.* 271:26469–26472 (1996)). Similar conclusions were derived from earlier receptor chimera studies (Jüppner, H., et al., *Endocrinology* 134:879–884 (1994); Stroop, S., et al., *Biochem.* 34:1050–1057 (1994); Gardella, T. J., et al., *Endocrinology* 135:1186–1194 (1994)) and from recent crosslinking studies with photoreactive PTH analogs (Bisello, A., et al., *J. Biol. Chem.* 273:22498–22505 (1998); Mannstadt, M., et al., *J. Biol. Chem.* 273:16890–16896 (1998)). Some recognition determinants for the family B receptors have been identified in the amino-terminal extracellular domain, the extracellular loops and the transmembrane helices (Turner, P., et al., Single Mutations Allow the PTH-2 Receptor to Respond to PTHrP J. Bone Min. Res. 12, Supplement 1, Abstract #121 (1997), Dautzenberg, F., et al., *Proc. Natl. Acad. Sci.* 95:4941–4946 (1998), Holtmann, M., et al., *J. Biol. Chem.* 270:14394–14398 (1995), Gardella, T. J., et al., *Endrocrinology* 135:1186–1194 (1994); Bergwitz, C., et al., *J. Biol. Chem.* 272:288619–28868; Turner, P. R., et al., *J Biol. Chem.* 271(16):9205–9208 (1996)). Thus, G protein coupled receptor ligand systems, and the B family in particular, function through similar ligand/receptor interactions as the PTH/PTH receptor system.

Figures 1, 8B:
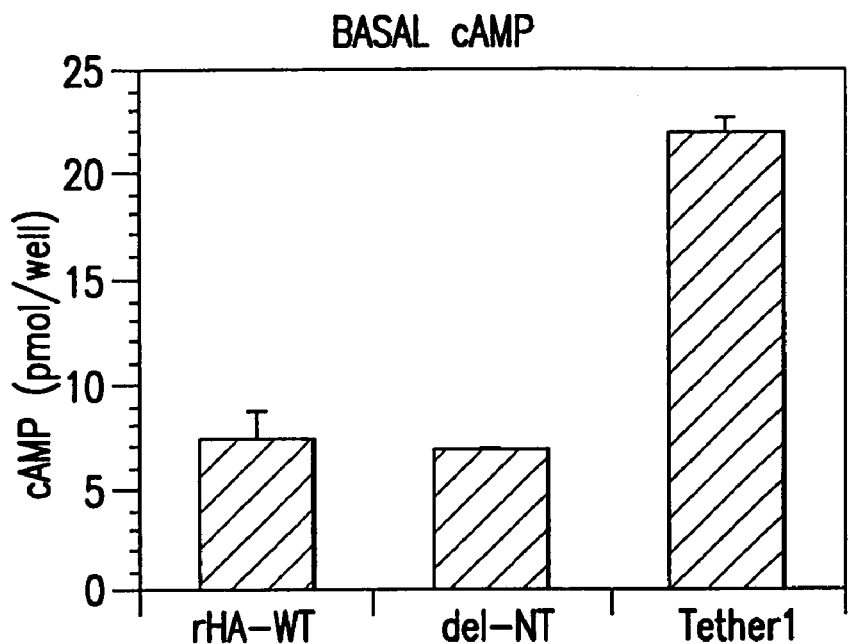
FIG. 1, Presentation of PG5 (PTH(1–9)-(Gly)$_5$-PTH (15–31)) amino acid (SEQ ID NO:9) and nucleic acid (SEQ ID NO:14) sequence; PG7 (PTH (1–9)-(Gly)$_7$-PTH(17–31)) amino acid (SEQ ID NO:11) and nucleic acid (SEQ ID NO:15) sequence; and PG9 (PTH (1–5)-(Gly)$_9$-PTH (15–31)) amino acid (SEQ ID NO:13) and nucleic acid (SEQ ID NO:16) sequence.
Figures 2, 8B:
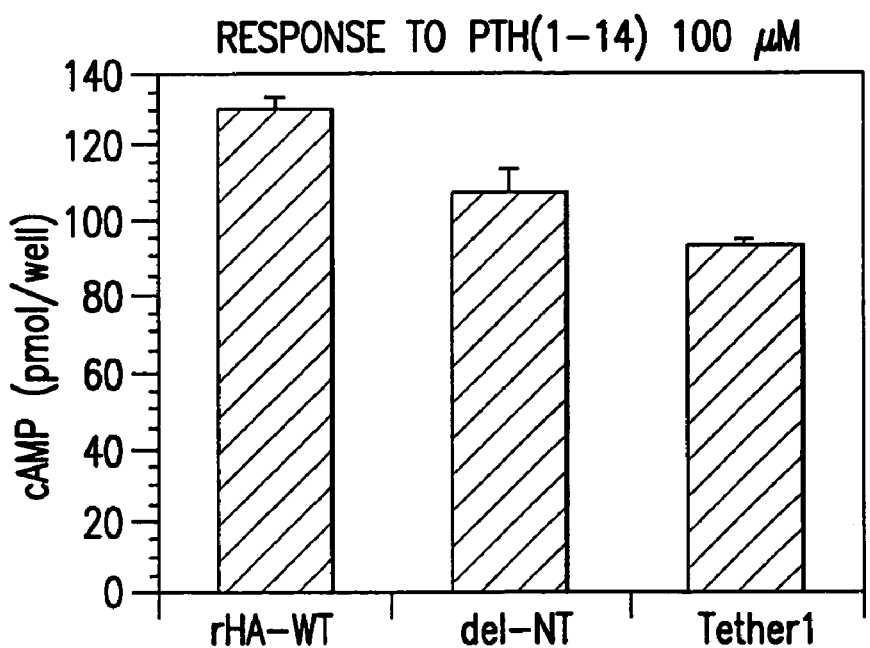
FIG. 2. Presentation of the G protein receptor coupled B family ligand amino-terminal sequences.

In another embodiment of the invention, the general formula S-(L)$_n$-B composition of the invention may be extended to other ligand/receptor family members of which PTH is a member, e.g., calcitonin, secretin, etc. In FIG. 2, the amino-terminal sequence of several ligands in this family is presented. Such information is useful in the design of functional domain conjugate peptides (S-(L)$_n$-B) for these ligands. Those skilled in the art are knowledgeable in the properties of the sequences presented and may select S peptides and B peptides from the sequence provided in FIG. 3.

In accordance with another aspect of the present invention, substituents may be attached to the free amine of the N-terminal amino acid of S-(L)$_n$-B compounds of the invention or derivatives thereof by standard methods known in the art in the making of a bioactive peptide. For example, alkyl groups, e.g., $C_{1-12}$ alkyl, may be attached using reductive alkylation. Hydroxyalkyl groups, e.g. $C_{1-12}$ hydroxyalkyl, may also be attached using reductive alkylation wherein the free hydroxy group is protected with a t-butyl ester. Acyl groups, e.g., $COE_1$, may be attached by coupling the free acid, e.g., $E_1COOH$, to the free amino of the N-terminal amino acid. Also contemplated within the scope of this invention are those S-(L)$_n$-B compounds of the invention or derivatives thereof that alter secondary or tertiary structure, or stability of S-(L)$_n$-B compounds of the invention or derivatives thereof which still retain biological activity. Such derivatives might be achieved through lactam cyclization, disulfide bonds, or other means known to a person of ordinary skill in the art.

In the above general structure, S-(L)$_n$-B, L is a linker sequence of any useful length. Preferably it is an amino acid residue (L)$_n$, wherein n is an integer greater than or equal to 1, preferably an integer of from 5 to 9. Where two or more residues are present, they may be the same or different. The amino acid(s) of which the spacer sequence is comprised may be any of those well-known to those skilled in the art, either essential or non-essential. For example, L may be, either alone or in combination, glycine, arginine, glutamic acid, lysine, aspartic acid, valine, cysteine, leucine, isoleucine, norleucine, methionine, histidine, proline, tryptophan, tyrosine, asparagine, glutamine, serine, threonine, alanine, glycine, or phenylalanine. Preferred amino acid residues for use as a linker sequence in the practice of the present invention are, either alone or in combination, glycine, norleucine, tyrosine, aspartic acid, lysine, leucine, and phenylalanine. L may also be an aliphatic diamine, preferably an aliphatic diamine from 1 to 6 carbon atoms, e.g., methylene diamine, ethylene diamine, propylene diamine, tetramethylene diamine, pentamethylene diamine, and hexamethylene diamine. Additionally L may be an aliphatic diamine having from 4 to 6 carbon atoms, e.g., tetramethylene diamine (also known as cadaverine), pentamethylene diamine (also known as putrescine, hereinafter Pu), and hexamethylene diamine.

Other linker molecules will be known to those skilled in the art and may be utilized for $(L)_n$ in the general formula $S-(L)_n-B$ for the making of bio active peptides of the invention.

3. Screen for $S-(L)_n-B$ Activity on PTH Receptor

Functional characterization of the biological properties of the $S-(L)_n-B$ compounds of the invention and derivatives thereof may be performed by bioassays that measure ligand-stimulated cAMP accumulation.

A. Stimulation of Cyclic AMP Accumulation by $S-(L)_n-B$ Compounds of the Invention Intracellular cAMP accumulation is measured as described previously (Abou-Samra et al., *J. Biol. Chem.* 262:1129, 1986). Cells grown in 24-well plates are rinsed with culture medium containing 0.1% BSA and 2 mM IBMX. The cells are then incubated with an $S-(L)_n-B$ compound or derivatives thereof for 60 min. at 21° C. The supernatant is removed and the cells immediately frozen by placing the whole plate in dry ice powder. Intracellular cAMP is extracted by thawing the cells in 1 ml of 50 mM HCl and analyzed by a specific radioimmunoassay using an anti-cAMP antibody (e.g., Sigma, St. Louis, Mo.). A cAMP analog (2'-O-monosuccinyl-adenosine 3':5'-cyclic monophosphate tyrosyl methyl ester, obtained from Sigma) which is used a tracer for cAMP is iodinated by the chloramine T method. Free iodine is removed by adsorbing the iodinated cAMP analog onto a C18Sep-pak cartridge (Waters, Milford, Mass.). After washing with $dH_2 0$, the iodinated cAMP analog is eluted from the Sep-pak Cartridge with 40% acetonitrille (ACN) and 0.1% trifluoroacetic acid (TFA). The iodinated cAMP analog is lyophilized, reconstituted in 1 ml 0.1% TFA, and injected into a C18 reverse phase HPLC column (Waters). The column is equilibrated with 10% ACN in 0.1% TFA, and eluted with gradient of 10–30% ACN in 0.1% TFA. This allows separation of the mono-iodinated cAMP analog from the non-iodinated cAMP analog. The tracer is stable for up to 4 months when stored at –20° C. The standard used for the assay, adenosine 3':5'-cyclic monophosphate, may be purchased from Sigma. Samples (1–10 82 1 of HCl extracts) or standards (0.04–100 mol/tube) are diluted in 50 Mm Na-acetate (pH 5.5), and acetylated with 10 µl of mixture of triethylamine and acetic anhydride (2:1 vol:vol). After acetylation, cAMP antiserum (100 µl) is added from a stock solution (1:4000) made in PBS (pH 7.4), 5 mM EDTA and 1% normal rabbit serum. The tracer is diluted in PBS (pH 7.4) with 0.1% BSA, and added (20,000 cpm/tube). The assay is incubated at 4° C. overnight. The bound tracer is precipitated by adding 100 µl of goat anti-rabbit antiserum (1:20 in PBS) and 1 ml of 7% polyethyleneglycol (MW 5 000–6000), centrifuging at 2000 rpm for 30 min. at 4° C. The supernatant is removed and the bound radioactivity is counted in a gamma-counter (Micromedic). To compute the cAMP data, logit calculations are performed in Excel spreadsheets. Typically, the assay sensitivity is 0.1 fmol/tube, and the standard concentration that displaces 50% of tracer is 5 fmol/tube.

B. Binding of $S-(L)_n-B$ Compounds of the Invention or Derivatives Thereof to Cloned Receptors Expressed on COS Cells In addition to the cAMP accumulation assay described below, it is possible that $S-(L)_n-B$ compounds of the invention or derivatives thereof may also be iodinated and used in a radioreceptor-based assay in transiently transfected COS cells. COS-7 cells are grown in 15 cm plates in DMEM, 10% heat-inactivated FBS, 10 mg/L gentamycin until 80–90% confluent. Twenty-four hours after transfection by the DEAE/Dextran method (Sambrook et al., supra), with 1–2 µg of plasmid DNA, the cells are trypsinized and replated in multiwell plastic dishes (16 or 35 mm diameter, Costar, Cambridge, Mass.) at a cell concentration of $5 \times 10^4$ cells/$cm^2$. Cell number increased only slightly after transfection. After continuing culture for another 48 h, radioreceptor assays are performed. The culture medium is replaced with buffer containing 50 mM Tris-HCL (pH 7.7), 100 mM NaCl, 2 mM $CaCl_2$, 5 mM KCL, 0.5% heat-inactivated fetal bovine serum (GIBCO), and 5% heat-inactivated horse serum (KC Biological Inc., Lenexa, Kans.) immediately before studies are initiated. Unless otherwise indicated, studies are conducted with cells incubated in this buffer at 15° C. for 4 h with $4 \times 10^5$ cpm/ml ($9.6 \times 10^{-11}$ M) of $^{125}I$-labeled [$Ala^1$]PTH(1–14) amide or $^{125}I$-labeled [$Nle^8$]PTH (1–14). Alternatively, more convention radioligands such as [nel8,21, Tyr34]-rPTH(1–34)$NH_2$ may also be used.

4. Vectors, Host Cells, and Recombinant Expression

The present invention also relates to vectors that comprise a $S(L)_n-B$ polynucleotide of the present invention, i.e. polynucleotides that encode the polypeptides of the invention. Such polynucleotide sequences are easily designed by those skilled in the art using the $S-(L)_n-B$ peptide sequences provided herein. Host cells which are genetically engineered with vectors of the invention may be used in the production of $S-(L)_n-B$ polypeptides of the invention by recombinant techniques. Cell-free translation systems can also be employed to produce such proteins using RNAs derived from the DNA constructs of present invention.

For recombinant production, host cells can be genetically engineered to incorporate expression systems or portions thereof for $S-(L)_n-B$ polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., Molecular Cloning: A Laboratory Manual (supra).

RNA vectors may also be utilized for the expression of the nucleic acids encoding S-$(L)_n$-B compounds or derivatives thereof disclosed in this invention. These vectors are based on positive or negative strand RNA viruses that naturally replicate in a wide variety of eukaryotic cells (Bredenbeek, P. J. & Rice, C. M., *Virology* 3: 297–310, 1992). Unlike retroviruses, these viruses lack an intermediate DNA lifecycle phase, existing entirely in RNA form. For example, alpha viruses are used as expression vectors for foreign proteins because they can be utilized in a broad range of host cells and provide a high level of expression; examples of viruses of this type include the Sindbis virus and Semliki Forest virus (Schlesinger, S., TIBTECH 11: 18–22, 1993; Frolov, I., et al, Proc. Natl. Acad. Sci. (USA) 93: 11371–11377, 1996). As exemplified by Invitrogen's Sinbis expression system, the investigator may conveniently maintain the recombinant molecule in DNA form (pSinrep5 plasmid) in the laboratory, but propagation in RNA form is feasible as well. In the host cell used for expression, the vector containing the gene of interest exists completely in RNA form and may be continuously propagated in that state if desired.

For secretion of the translated protein into the lumen of the endoplasmic reticulum, into the periplasmic space or into the extracellular environment appropriate secretion signals may be incorporated into the desired S-$(L)_n$-B polypeptide. These signals may be endogenous to the polypeptide or they may be heterologous signals.

The expression of a DNA sequence requires that the DNA sequence be "operably linked" to DNA sequences which contain transcriptional and translational regulatory information. An operable linkage is a linkage in which the control or regulatory DNA sequences and the DNA sequence sought to be expressed are connected in such a way as to permit gene expression. The precise nature of the "control regions" needed for gene expression may vary from organism to organism, but shall in general include a promoter region which, in prokaryotic cells, contains both the promoter (which directs the initiation of RNA transcription) as well as DNA sequences which, when transcribed into RNA, will signal the initiation of protein synthesis. Regulatory regions in eukaryotic cells will in general include a promoter region sufficient to direct the initiation of RNA synthesis.

Two DNA sequences are said to be operably linked if the nature of the linkage between the two DNA sequences does not (1) result in the introduction of a frame shift mutation, (2) interfere with the ability of the promoter region sequence to direct the transcription of the fusion protein-encoding sequence or (3) interfere with the ability of the fusion protein-encoding sequence to be transcribed by the promoter region sequence. Thus, a promoter region would be operably linked to a DNA sequence if the promoter were capable of transcribing that DNA sequence.

The joining of various DNA fragments, to produce the expression vectors of this invention is performed in accordance with conventional techniques, employing blunt-ended or staggered-ended termini for ligation, restriction enzyme digestion to provide appropriate termini, filling in of cohesive ends as appropriate, alkali and phosphatase treatment to avoid undesirable joining, and ligation with appropriate ligates. In the case of a fusion protein, the genetic construct encodes an inducible promoter which is operably linked to the 5' gene sequence of the fusion protein to allow efficient expression of the fusion protein.

To express S-$(L)_n$-B compounds of the invention or a derivative thereof in a prokaryotic cell (such as, for example, *E. coli, B. subtilis, Pseudomonas*, Streptomyces, etc.), it is necessary to operably link the SEQ ID NO: 1-encoding DNA sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pBR325, etc. Examples of inducible prokaryotic promoters include the major right and left promoters of bacteriophage λ, (PL and PR), the trp, recA, lacZ, lacI, and gal promoters of *E. coli*, the α-amylase (Ulmanen, I. et al., *J. Bacteriol.* 162:176–182 (1985)), and the σ-28-specific promoters of *B. subtilis* (Gilman, M. Z. et al., *Gene* 32:11–20 (1984)), the promoters of the bacteriophages of *Bacillius* (Gryczan, T. J., In: *The Molecular Biology of the Bacilli*, Academic Press, Inc., NY (1982)), and *Streptomyces* promoters (Ward, J. M. et al., *Mol Gen. Genet.* 203:468–478 (1986)). Prokaryotic promoters are reviewed by Glick, B. R., *J. Ind. Microbiol.* 1:277–282 (1987); Cenatiempo, Y., *Biochimie* 68:505–516 (1986)); and Gottesman, S., *Ann. Rev. Genet.* 18:415–442 (1984)).

The preferred prokaryotic promoter for this invention is the *E. coli* trp promoter, which is inducible with indole acrylic acid.

If expression is desired in a eukaryotic cell, such as yeast, fungi, mammalian cells, or plant cells, then it is necessary to employ a promoter capable of directing transcription in such a eukaryotic host. Preferred eukaryotic promoters include the promoter of the mouse metallothionein I gene (Hamer, D. et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981)); and the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)).

Preferably, the introduced gene sequence will be incorporated into a plasmid or viral vector capable of autonomous replication in the recipient host. Any of a wide variety of vectors may employed for this purpose. Factors of importance in selecting a particular plasmid or viral vector include: the case with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColE1, PSC101, pACYC 184, πVX. Such plasmids are, for example, disclosed by Maniatis, T., et al., *In: Molecular Cloning*, A Laboratory Manual, Cold Spring Harbor Press, Cold Spring Harbor, N.Y. (1982)). Preferred plasmid expression vectors include the pGFP-1 plasmid described in Gardella et al., *J. Biol. Chem.* 265:15854–15859 (1989), or a modified plasmid based upon one of the pET vectors described by Studier and Dunn, *Methods in Enzymology* 185: 60–89 (1990). Bacillus plasmids include pC194, pC221, pT127, etc. Such plasmids are disclosed by Gryczan, T. In: The Molecular Biology of the Bacilli, Academic Press, NY pp. 307–329 (1982). Suitable *Streptomyces* plasmids include pIJIOI (Kendall, K. J. et al., *J. Bacteriol.* 169:4177–4183 (1987)), and *streptomyces* bacteriophages such as φC31 (Chater, K. F. et al., *In: Sixth International Symposium on Actinomycetales Biology*, Akademiai Kaido, Budapest, Hungary, pp. 45–54 (1986)). *Pseudomonas* plasmids are reviewed by John, J. F. et al., *Rev. Infect. Dis.* 8:693–704 (1986)), and Izaki, K., *Jon. J. Bacteriol.* 33:729–742 (1978)).

Preferred eukaryotic expression vectors include, without limitation, BPV, vaccinia, 2-micron circle etc. Such expression vectors are well known in the art (Botstein, D., et al., *Miami Wntr. Symp.* 19:265–274 (1982); Broach, J. R., *In: The Molecular Biology of the Yeast Saccharomyces: Life Cycle and Inheritance*, Cold Spring Harbor Laboratory, Cold Spring Harbor, N.Y. pp. 445–470 (1981); Broach, J. R., *Cell* 28:203–204 (1982); Bollon, D. P., et al., *J. Clin. Hematol. Oncol.* 10:39–48 (1980); Maniatis, T., *In: Cell Biology: A Comprehensive Treatise*, Vol. 3, Gene Expression, Academic Press, NY, pp. 563–608 (1980)).

In addition to microorganisms, cultures of cells derived from multicellular organisms may also be used as hosts. In principle, any such cell culture is workable, whether from vertebrate or invertebrate cellular sources. Interest, however, has been greater with cells from vertebrate sources. Examples of useful vertebrate host cell lines are VERO and HeLa cells, Chinese hamster ovary (CHO) cell lines, WI38, BHK, COS-7, and MDCK cell lines. Expression vectors for such cells ordinarily include (if necessary) an origin of replication, a promoter located in front of or upstream to the gene to be expressed, along with any necessary ribo some binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Simian Virus 40 (SV40) and cytomegalovirus. The early and late promoters of SV40 virus are particularly useful because both are obtained easily from the virus as a fragment which also contains the SV40 vial origin of replication (Fiers et al, *Nature* 273:113 (1978)).

An origin of replication may be provided either by construction of the vector to include an exogenous origin, such as may be derived from SV40 or other viral (e.g. Polyoma, Adeno, VSV, BPV) source or may be provided by the host cell chromosomal replication mechanism. If the vector is integrated into the host cell chromosome, the latter is often sufficient.

If cells without formidable cell membrane barriers are used as host cells, transfection is carried out by the calcium phosphate precipitation method as described by Graham and Van der Erb, *Virology* 52:546 (1978). However, other methods for introducing DNA into cells, such as by nuclear injection or by protoplast fusion may also be used. In the case of gene therapy, the direct naked plasmid or viral DNA injection method, with or without transfection-facilitating agents such as, without limitation, liposomes, provides an alternative approach to the current methods of in vivo or in vitro transfection of mammalian cells. If prokaryotic cells or cells which contain substantial cell wall constructions are used, the preferred method of transfection is calcium treatment, using calcium chloride as described in Cohen et al., *Proc. Natl. Acad. Sci. USA* 69:2110 (1972).

5. Utility and Administration of S-(L)$_n$-B Compounds of the Invention or Derivatives Thereof S-(L)$_n$-B Compounds of the invention or derivatives thereof are useful for the prevention and treatment of a variety of mammalian conditions manifested by loss of bone mass. In particular, the compounds of this invention are indicated for the prophylaxis and therapeutic treatment of osteoporosis and osteopenia in humans. Furthermore, the compounds of this invention are indicated for the prophylaxis and therapeutic treatment of other bone diseases. The compounds of this invention are indicated for the prophylaxis and therapeutic treatment of hypoparathyroidism. Finally, the compounds of this invention are indicated for use as agonists for fracture repair and as antagonists for hypercalcemia.

In general, S-(L)$_n$-B compounds or derivatives thereof of this invention, or salts thereof, are administered in amounts between about 0.01 and 1 μg/kg body weight per day, preferably from about 0.07 to about 0.2 μg/kg body weight per day. For a 50 kg human female subject, the daily dose of biologically active compounds of SEQ ID NO: 1 or derivatives thereof is from about 0.5 to about 50 μgs, preferably from about 3.5 to about 10 μgs. In other mammals, such as horses, dogs, and cattle, higher doses may be required. This dosage may be delivered in a conventional pharmaceutical composition by a single administration, by multiple applications, or via controlled release, as needed to achieve the most effective results, preferably one or more times daily by injection. For example, this dosage may be delivered in a conventional pharmaceutical composition by nasal insufflation.

The selection of the exact dose and composition and the most appropriate delivery regimen will be influenced by, inter alia, the pharmacological properties of the selected S-(L)$_n$-B compounds of the invention or derivatives thereof, the nature and severity of the condition being treated, and the physical condition and mental acuity of the recipient.

Representative preferred delivery regimens include, without limitation, oral, parenteral (including subcutaneous, transcutaneous, intramuscular and intravenous), rectal, buccal (including sublingual), transdermal, and intranasal insufflation.

Pharmaceutically acceptable salts retain the desired biological activity of the S-(L)$_n$-B compounds of the invention or derivatives thereof without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like.

A further aspect of the present invention relates to pharmaceutical compositions comprising as an active ingredient S-(L)$_n$-B compounds of or derivatives thereof of the present invention, or pharmaceutically acceptable salt thereof, in admixture with a pharmaceutically acceptable, non-toxic carrier. As mentioned above, such compositions may be prepared for parenteral (subcutaneous, transcutaneous, intramuscular or intravenous) administration, particularly in the form of liquid solutions or suspensions; for oral or buccal administration, particularly in the form of tablets or capsules; for rectal, transdermal administration; and for intranasal administration, particularly in the form of powders, nasal drops or aerosols.

The S-(L)$_n$-B compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985), incorporated herein by reference. Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acylcarnitines. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for the most preferred route of administration, nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Delivery of the S-(L)$_n$-B compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the polypeptide or its salt dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189, incorporated by reference herein. The compounds or, preferably, their relatively insoluble salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J. R. Robinson ed., Marcel Dekker, Inc., New York, 1978, and R. W. Baker, Controlled Release of Biologically Active Agents, John Wiley & Sons, New York, 1987, incorporated by reference herein.

Like PTH, the S-(L)$_n$-B variants may be administered in combination with other agents useful in treating a given clinical condition. When treating osteoporosis and other bone-related disorders for example, the S-(L)$_n$-B variants may be administered in conjunction with a dietary calcium supplement or with a vitamin D analog (see U.S. Pat. No. 4,698,328). Alternatively, the S-(L)$_n$-B variant may be administered, preferably using a cyclic therapeutic regimen, in combination with bisphosphonates, as described for example in U.S. Pat. No. 4,761,406, or in combination with one or more bone therapeutic agents such as, without limitation, calcitonin and estrogen.

V Receptor-Signaling Activities of S-(L)$_n$-B Compounds of the Invention or Derivatives Thereof A crucial step in the expression of hormonal action is the interaction of hormones with receptors on the plasma membrane surface of target cells. The formation of hormone-receptor complexes allows the transduction of extracellular signals into the cell to elicit a variety of biological responses.

A. Screening for PTH-1 Receptor Antagonists and Agonists

S-(L)$_n$-B polypeptides of the invention may be screened for their agonistic or antagonistic properties using the cAMP accumulation assay. Cells expressing PTH-1 receptor on the cell surface are incubated with native PTH(1–84) for 5–60 minutes at 37° C., in the presence of 2 mM IBMX (3-isobutyl-1-methyl-xanthine, Sigma, St. Louis, Mo.). Cyclic AMP accumulation is measured by specific radio-immuno assay, as described above. An S-(L)$_n$-B compound of the invention or a derivative thereof that competes with native PTH(1–84) for binding to the PTH-1 receptor, and that inhibits the effect of native PTH(1–84) on cAMP accumulation, is considered a competitive antagonist. Such a compound would be useful for treating hypercalcemia.

Conversely, a An S-(L)$_n$-B compound of the invention or a derivative thereof that does not compete with native PTH(1–84) for binding to the PTH-1 receptor, but which still prevents native PTH(1–84) activation of cAMP accumulation (presumably by blocking the receptor activation site) is considered a non-competitive antagonist. Such a compound would be useful for treating hypercalcemia.

An S-(L)$_n$-B compound of the invention or a derivative thereof that competes with native PTH(1–84) for binding to the PTH-1 receptor, and which stimulates cAMP accumulation in the presence or absence of native PTH(1–84) is a competitive agonist. An S-(L)$_n$-B compound of the invention or a derivative thereof that does not compete with native PTH(1–84) for binding to the PTH-1 receptor but which is still capable of stimulating cAMP accumulation in the presence or absence of native PTH(1–84), or which stimulates a higher cAMP accumulation than that observed by a compound of SEQ ID NO: 1 or a derivative thereof alone, would be considered a non-competitive agonist.

6. Therapeutic Uses of S-(L)$_n$-B Compounds of the Invention or Derivatives Thereof Some forms of hypercalcemia and hypocalcemia are related to the interaction between PTH and PTHrP and the PTH-1 and PTH-2 receptors. Hypercalcemia is a condition in which there is an abnormal elevation in serum calcium level; it is often associated with other diseases, including hyperparathyroidism, osteoporosis, carcinomas of the breast, lung and prostate, epidermoid cancers of the head and neck and of the esophagus, multiple myeloma, and hypernephroma. Hypocalcemia, a condition in which the serum calcium level is abnormally low, may result from a deficiency of effective PTH, e.g., following thyroid surgery.

Nucleic acids of the invention which encode an S-$(L)_n$-B compound of the invention or derivatives thereof may also be linked to a selected tissue-specific promoter and/or enhancer and the resultant hybrid gene introduced, by standard methods (e.g., as described by Leder et al., U.S. Pat. No. 4,736,866, herein incorporated by reference), into an animal embryo at an early developmental stage (e.g., the fertilized oocyte stage), to produce a transgenic animal which expresses elevated levels of an S-$(L)_n$-B compound of the invention or derivatives thereof in selected tissues (e.g., the osteocalcin promoter for bone). Such promoters are used to direct tissue-specific expression of compounds of SEQ ID NO: 1 or derivatives thereof in the transgenic animal.

In addition, any other amino-acid substitutions of a nature, which do not destroy the ability of the an S-$(L)_n$-B compound of the invention to antagonize or agonize the PTH-1/PTH-2 receptor (as determined by assays known to the skilled artisan and discussed below), are included in the scope of the present invention.

By "agonist" is intended a ligand capable of enhancing or potentiating a cellular response mediated by the PTH-1 receptor. By "antagonist" is intended a ligand capable of inhibiting a cellular response mediated by the PTH-1 receptor. Whether any candidate "agonist" or "antagonist" of the present invention can enhance or inhibit such a cellular response can be determined using art-known protein ligand/receptor cellular response or binding assays, including those described elsewhere in this application.

In accordance with yet a further aspect of the invention, there is provided a method for treating a medical disorder that results from altered or excessive action of the PTH-1 receptor, comprising administering to a patient a therapeutically effective amount of an S-$(L)_n$-B compound of the invention of a derivative thereof sufficient to inhibit activation of the PTH-1 receptor of said patient.

In this embodiment, a patient who is suspected of having a disorder resulting from altered action of the PTH-1 receptor may be treated using an S-$(L)_n$-B compound of the invention or derivatives thereof of the invention which are a selective antagonists of the PTH-1 receptor. Such antagonists include an S-$(L)_n$-B compound of the invention or derivatives thereof of the invention which have been determined (by the assays described herein) to interfere with PTH-1 receptor-mediated cell activation or other derivatives having similar properties.

To administer the antagonist, the appropriate an S-$(L)_n$-B compound of the invention or a derivative thereof is used in the manufacture of a medicament, generally by being formulated in an appropriate carrier or excipient such as, e.g., physiological saline, and preferably administered intravenously, intramuscularly, subcutaneously, orally, or intranasally, at a dosage that provides adequate inhibition of an S-$(L)_n$-B compound of the invention or a derivative thereof binding to the PTH-1 receptor. Typical dosage would be 1 ng to 10 mg of the peptide per kg body weight per day.

In accordance with yet a further aspect of the invention, there is provided a method for treating osteoporosis, comprising administering to a patient a therapeutically effective amount of an S-$(L)_n$-B compound of the invention or a derivative thereof, sufficient to activate the PTH-1 receptor of said patient. Similar dosages and administration as described above for the PTH/PTHrP antagonist, may be used for administration of a PTH/PTHrP agonist, e.g., for treatment of conditions such as osteoporosis, other metabolic bone disorders, and hypoparathyroidism and related disorders.

It will be appreciated to those skilled in the art that the invention can be performed within a wide range of equivalent parameters of composition, concentration, modes of administration, and conditions without departing from the spirit or scope of the invention or any embodiment thereof.

7. Novel PTH Receptor Molecules of the Invention

In one embodiment, the invention provides nucleic acid and polypeptide sequences for novel PTH receptor molecules that are useful for the identification of agonists and antagonists of PTH receptor function.

Thus in one specific embodiment, the invention provides novel ligand/receptor chimeric molecules, referred to herein as tethered ligand/receptor molecules. This aspect of the invention advances the art by establishing that the majority of the extracellular amino-terminal domain of the PTH-1 receptor is not absolutely required for ligand signaling as measured by cAMP production. This result is unexpected given that there are six highly conserved cysteine residues present in the extracellular domain that ostensibly constrain the molecule structurally. Moreover, the "tethering" of ligand peptide to the deletion mutant rδNt amino-terminus provides an unanticipated and surprising result of creating an auto-stimulating receptor molecule that will be useful in the identification of agonists and antagonists of PTH receptor function. Since the majority of known antagonists of the PTH receptor bind to the carboxyl-terminal fragment of the ligand, Tether 1 should prove useful in the identification of antagonists that act on the amino-terminal or signaling domain of the ligand.

The general formula of the tethered ligand/receptor of the invention is $R_1$—S-$(L)_n$—R, wherein R1 is the PTH-1 receptor signal sequence; S is an amino-terminal ligand signaling peptide; L is a linker molecule present N times, where N is a positive integer 1–10, most preferably 4, and R is PTH-1 receptor sequence. It should be clear that in instances where specific examples of tethered receptors are mentioned below, such as for example Tether-1, other tethered receptors may be substituted, such as, but not limited to, for example [R11]-Tether(1–11).

In a specific embodiment, the invention provides Tether-1 (also referred to as Tether(1–9)) presented in FIG. 7 (SEQ ID NO:36). The $R_1$—S-$(L)_n$-R composition formula for Tether-1 is defined as $R_1$ being PTH-1 receptor(1–25) peptide; S being the PTH(1–9) peptide; L being Gly, wherein N is 4; and R is the PTH-1 receptor (182-end). Thus, the entire sequence is defined as the following: PTH-1 receptor (1–25)—PTH(1–9)-(Gly)$_4$-PTH-1 receptor(182-end).

The invention also covers the mature form of the Tether-1 receptor, defined by the formula S-$(L)_n$-R, wherein the $R_1$ moiety has been cleaved by signal processing.

Tether-1 receptor may be constructed using common knowledge in the art of molecular biology. Substitution of the PTH(1–9) (SEQ ID NO:1) amino-terminal fragment for the wild-type sequence represented by amino acid residues 26–181 of the native rat PTH-1 receptor is easily accomplished. The resultant clone will have the structure of Tether-1, wherein amino acid residues 1–22 represent a signal peptide that is cleaved. It should be noted that $Tyr^{23}$ was originally believed to be the site of cleavage, but the evidence indicates that this residue remains attached and cleavage occurs between position 22 and 23; the removal of this $Tyr^{23}$ residue may provide increased activity for the peptides described herein.

In another specific embodiment, the invention provides the Tether-1C receptor, which is similar to the Tether-1 receptor except that there is a truncation of the intracellular carboxy-terminal domain, an area that is thought to be important in the down regulation of the receptor, possibly through a phosphorylation mechanism. The structure of Tether-1C is identical to Tether-1 with the exception of a stop codon being introduced at amino acid position 481 of the PTH-1 receptor moiety. This receptor should increase sensitivity of screening for agonists and enable a more pure screen of agonists acting at the signaling/transmembrane region of the ligand/receptor complex.

In another specific embodiment, the invention provides the rδNt/Ct receptor, a double mutant receptor lacking the extracellular amino terminal domain of the receptor, important for ligand interaction, and the intracellular carboxy-terminal domain of the receptor, important for down regulation.

Thus, the novel receptors of the invention should be important for the identification of novel agonists and antagonists of the PTH receptor function. Such agonists or antagonists may be variants of the PTH ligand or structurally different mimetics.

a) Novel Receptor Nucleic Acid Molecules

Unless otherwise indicated, all nucleotide sequences determined by sequencing a DNA molecule herein were determined by manual sequencing, and all amino acid sequences of polypeptides encoded by DNA molecules determined herein were predicted by translation of a DNA sequence determined as above. Therefore, as is known in the art for any DNA sequence determined by this approach, any nucleotide sequence determined herein may contain some errors. Nucleotide sequences determined by manual sequencing are typically at least about 95% to at least about 99.9% identical to the actual nucleotide sequence of the sequenced DNA molecule. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 7, 9 and 10, a nucleic acid molecule of the present invention encoding a Tether-1 receptor, Tether-1C receptor, and rδNt/Ct receptor polypeptide, respectively, may be obtained using standard techniques. Cloning and screening procedures are known for the isolation of the wild-type PTH1R sequence, such as those for cloning cDNAs using mRNA as starting material. Subsequent to cloning the wild-type receptor, the appropriate deletion in the sequence may be made as described herein. Illustrative of the invention, the nucleic acid molecule described in SEQ ID NO:36, SEQ ID NO:38 and SEQ ID NO:40 was obtained by using standard restriction enzyme digestion and cloning techniques in the art. The determined nucleotide sequences of Tether-1 receptor (SEQ ID NO:36), Tether-1C receptor (SEQ ID NO:10), and rδNt/Ct (SEQ ID NO:40) contains an open reading frame encoding a protein predicted leader sequence of about 22 amino acid residues. The amino acid sequence of the predicted mature Tether-1 receptor, Tether-1C receptor, and rδNt/Ct receptor is shown in FIGS. 7, 9 and 10.

As indicated, the present invention also provides the mature form(s) of the Tether-1 receptor, Tether-1C receptor, and rδNt/Ct receptor of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, in one embodiment the present invention provides, for example, a nucleotide sequence encoding the mature Tether-1 receptor, Tether-1 receptor, and rδNt/Ct receptor polypeptides having the amino acid sequences of SEQ ID NO:37, SEQ ID NO:39 and SEQ ID NO:41 respectively. Additional embodiments may include the nucleotide sequences encoded by any of the deposited plasmids. Embodiments of the claimed invention may be drawn for example to human or rat receptor sequences.

Several plasminds encoding receptors have been deposited as follows:

| Strain # | | Receptor |
|---|---|---|
| TG-98 | E.coli MC1061/P3/Flac/p98 | rP1R-delNt |
| TG-422 | E.coli MC1061/P3/Flac/p422 | rP1R-Tether-1 |
| TG-433 | E.coli MC1061/P3/p433 | rP1R-Tether-(1–9) |
| TG-454 | E.coli MC1061/P3/Flac/p454 | hP1R-delNt |
| TG-462 | E.coli MC1061/P3/Flac/p462 | hP1R-Tether[R11]-(1–11) |
| TG-449 | E.coli MC1061/P3/Flac/p449 | hTether-1C (hTether-stop481) |
| TG-376 | E.coli MC1061/P3/Flac/p376 | rP1RdelNt/Ct | under the Budapest Treaty at the American Type Culture Collection, Manassas, Va. deposited on Dec. 28, 1999 and Dec. 30, 1999 and given accession numbers PTA-1136, PTA-1138, PTA-1139. PTA-1140, PTA-1142, PTA-1137 and PTA-1141, respectively.

By the mature receptors, e.g. Tether-1 receptor (Tether1–9 receptor), [R11]-Tether(1–11) receptor, Tether-1C receptor, and rde1Nt/Ct receptor protein having the amino acid sequence is meant the mature form(s) of the Tether-1 receptor (Tether (1–9) receptor), Tether-1C receptor, [R11]-Tether (1–11) and rde1Nt/Ct receptor produced by expression in a mammalian cell (e.g., COS cells, as described below) of the complete open reading frame encoded by the DNA sequence of the clone contained in the vector in the deposited host. As indicated below, the mature Tether-1 receptor, Tether-1C receptor, and rδNt/Ct receptor having the amino acid sequence encoded by cDNA clones, may or may not differ from the predicted "mature" Tether-1 receptor, Tether-1C receptor, and rδNt/Ct receptor protein shown in for example, FIGS. 7, 9 and 10 depending on the accuracy of the predicted cleavage.

Methods for predicting whether a protein has a secretory leader as well as the cleavage point for that leader sequence are available. For instance, the methods of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein. A computational method may be found in the computer program "PSORT" (K. Nakai and M. Kanehisa, Genomics 14:897–911 (1992)), which is an expert system for predicting the cellular location of a protein based on the amino acid sequence. As part of this computational prediction of localization, the methods of McGeoch and von Heinje are incorporated.

In the present case, the predicted amino acid sequence of the complete Tether-1 receptor, Tether-1C receptor, and rδNt/Ct receptor polypeptide of the present invention was analyzed for structural properties by comparison to the rat PTH-1 receptor sequence. This analysis provided predicted a cleavage site between amino acids 22 and 23 in SEQ ID NO:37, SEQ ID NO:39 and SEQ ID NO:41. Thus, the leader sequence for the Tether-1 receptor, Tether-1C receptor, and rδNt/Ct receptor protein is predicted to consist of amino acid residues 1–22 in SEQ ID NO:37, SEQ ID NO:39 and SEQ ID NO:41, while the predicted mature Tether-1 receptor, Tether-1C receptor, and rδNt/Ct receptor proteins begins at residues SEQ ID NO:37, SEQ ID NO:39 and SEQ ID NO:41.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

As one of ordinary skill would appreciate, however, due to the possibilities of sequencing errors, the Tether-1 receptor, Tether-1C receptor, and rδNt/Ct receptor polypeptide comprises about 435 amino acids, but may vary slightly in length; and the leader sequence of this protein is about 22 amino acids, but may be anywhere in the range of about 10 to about 30 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in SEQ ID NO:36, SEQ ID NO:38 and SEQ ID NO:40; DNA molecules comprising the coding sequence for the Tether-1 receptor, Tether-1C receptor, and rδNt/Ct receptor shown in SEQ ID NO:37, SEQ ID NO:39 and SEQ ID NO:41; and DNA molecules which comprise a sequence substantially different from those described above but which, due to the degeneracy of the genetic code, still encode the Tether-1 receptor, Tether-1C receptor, and rδNt/Ct receptor. Of course, the genetic code is well known in the art. Thus, it would be routine for one skilled in the art to generate such degenerate variants.

In another aspect, the invention provides isolated nucleic acid molecules encoding the Tether-1 receptor, Tether-1C receptor, and rδNt/Ct receptor polypeptide having an amino acid sequence encoded by the cDNA clones of the invention. Preferably, the nucleic acid molecules may be encoded by the mature polypeptide encoded by the above-described deposited cDNA clones. In a further embodiment, a nucleic acid molecule is provided encoding the Tether-1 receptor, Tether-1C receptor, and rδNt/Ct receptor polypeptide or the Tether-1 receptor, Tether-1C receptor, and rδNt/Ct receptor polypeptide lacking the N-terminal methionine. The invention also provides an isolated nucleic acid molecule having the nucleotide sequence shown in SEQ ID NO:1 or the nucleotide sequence of the Tether-1 receptor, Tether-1C receptor, and rδNt/Ct receptor cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the Tether-1 receptor, Tether-1C receptor, and rδNt/Ct receptor gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNAs or the nucleotide sequence shown in SEQ ID NO:36, SEQ ID NO:38 and SEQ ID NO:40 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments of about 50–1550 nt in length, and more preferably at fragments least about 600 nt in length are also useful according to the present invention as are fragments corresponding to most, if not all, of the nucleotide sequence of the deposited cDNAs or as shown in SEQ ID NO:36, SEQ ID NO:38 and SEQ ID NO:40. By a fragment at least 20 nt in length, for example, is intended fragments which include 20 or more contiguous bases from the nucleotide sequence of the deposited cDNAs or the nucleotide sequence as shown in SEQ ID NO:37, SEQ ID NO:39 and SEQ ID NO:41.

Preferred nucleic acid fragments of the present invention include nucleic acid molecules encoding: a polypeptide comprising the Tether-1 receptor, Tether-1C receptor, or rδNt/Ct receptor extracellular domain; a polypeptide comprising the Tether-1 receptor, Tether-1C receptor, or rδNt/Ct receptor transmembrane domain; and a polypeptide comprising the Tether-1 receptor, Tether-1C receptor, or rδNt/Ct receptor extracellular domain with all or part of the transmembrane domain deleted. As above with the leader sequence, the amino acid residues constituting the Tether-1 receptor, Tether-1C receptor, and rδNt/Ct receptor extracellular and transmembrane domains have been predicted. Thus, as one of ordinary skill would appreciate, the amino acid residues constituting these domains may vary slightly (e.g., by about 1 to about 15 amino acid residues) depending on the criteria used to define each domain.

In another aspect, the invention provides an isolated nucleic acid molecule comprising a polynucleotide which hybridizes under stringent hybridization conditions to a portion of the polynucleotide in a nucleic acid molecule of the invention described above. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1×SSC at about 65° C.

By a polynucleotide which hybridizes to a "Portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below. By a portion of a polynucleotide of "at least 20 nt in length," for example, is intended 20 or more contiguous nucleotides from the nucleotide sequence of the reference polynucleotide (e.g., the deposited cDNAs or the nucleotide sequence as shown in SEQ ID NO:37, SEQ ID NO:39 and SEQ ID NO:41.

Of course, a polynucleotide which hybridizes only to a poly A sequence (such as the 3' terminal poly(A) tract of the Tether-1 receptor, Tether-1C receptor, and rδNt/Ct receptor cDNA shown in SEQ ID NO:36, SEQ ID NO:38 and SEQ ID NO:40, or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a Tether-1 receptor, Tether-1C receptor, and rδNt/Ct receptor polypeptide may include, but are not limited to those encoding the amino acid sequence of the mature polypeptides, by themselves; the coding sequence for the mature polypeptides and additional sequences, such as those encoding the amino acid leader or secretory sequence, such as a pre-, or pro- or prepro-protein sequence, the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the Tether-1 receptor, Tether-1C receptor, and rδNt/Ct receptor fused to Fc at the—or C-terminus.

The present invention further relates to variants of the nucleic acid molecules of the present invention, which encode portions, analogs or derivatives of the Tether-1 receptor, Tether-1C receptor, and rδNt/Ct receptor. Variants may occur naturally, such as a natural allelic variant. By an "allelic variant" is intended one of several alternate forms of a gene occupying a given locus on a chromosome of an organism. *Genes II*, Lewin, B., ed., John Wiley &Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the Tether-1 receptor, Tether-1C receptor, and rδNt/Ct receptor or portions thereof. Also especially preferred in this regard are conservative substitutions.

Further embodiments of the invention include isolated nucleic acid molecules comprising a polynucleotide having a nucleotide sequence at least 95%, 96%, 97%, 98% or 99% identical to (a) a nucleotide sequence encoding the full-length Tether-1 receptor, Tether-1C receptor, or rδNt/Ct receptor polypeptide having the complete amino acid sequence in SEQ ID NO:37, SEQ ID NO:39 or SEQ ID NO:41, including the predicted leader sequence; (b) a nucleotide sequence encoding the polypeptide having the amino acid sequence in SEQ ID NO:37, SEQ ID NO:39 or SEQ ID NO:41, but lacking the N-terminal methionine; (c) a nucleotide sequence encoding the mature Tether-1 receptor, Tether-1C receptor, or rδNt/Ct receptor (full-length polypeptide with the leader removed) having the amino acid sequence indicated FIG. 7, 9 or 10 (SEQ ID NO:37, SEQ ID NO:39 or SEQ ID NO:41; (d) a nucleotide sequence encoding the full-length Tether-1 receptor, Tether-1C receptor, and rδNt/Ct receptor polypeptide having the complete amino acid sequence including the leader encoded by the cDNA; or (e) a nucleotide sequence encoding the mature Tether-1 receptor, Tether-1C receptor, and rδNt/Ct receptor having the amino acid sequence encoded by the cDNA; (f) a nucleotide sequence encoding the Tether-1 receptor, Tether-1C receptor, and rδNt/Ct receptor extracellular domain; (g) a nucleotide sequence encoding the Tether-1 receptor, Tether-1C receptor, and rδNt/Ct receptor transmembrane domain; (h) a nucleotide sequence encoding the Tether-1 receptor, Tether-1C receptor, and rδNt/Ct receptor extracellular domain with all or part of the transmembrane domain deleted; and (i) a nucleotide sequence complementary to any of the nucleotide sequences in (a), (b), (c), (d), (e), (f), (g) or (h).

By a polynucleotide having a nucleotide sequence at least, for example, 95% "identical" to a reference nucleotide sequence encoding a Tether-1 receptor, Tether-1C receptor, and rδNt/Ct receptor polypeptide is intended that the nucleotide sequence of the polynucleotide is identical to the reference sequence except that the polynucleotide sequence may include up to five point mutations per each 100 nucleotides of the reference nucleotide sequence encoding the Tether-1 receptor, Tether-1C receptor, or rδNt/Ct receptor. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in FIG. 1A or to the nucleotides sequence of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in FIG. 7, 9 or 10, or to the nucleic acid sequence of the deposited cDNAs, irrespective of whether they encode a polypeptide having Tether-1 receptor, Tether-1C receptor, and rδNt/Ct receptor activity. This is because even where a particular nucleic acid molecule does not encode a polypeptide having Tether-1 receptor, Tether-1C receptor, or rδNt/Ct receptor activity, one of skill in the art would still know how to use the nucleic acid molecule, for instance, as a hybridization probe or a polymerase chain reaction (PCR) primer. Uses of the nucleic acid molecules of the present invention that do not encode a polypeptide having Tether-1 receptor, Tether-1C receptor, or rδNt/Ct receptor activity include, inter alia, (1) isolating the Tether-1 receptor, Tether-1C receptor, or rδNt/Ct receptor gene or allelic variants thereof in a cDNA library; (2)/in situ hybridization (e.g., "FISH") to metaphase chromosomal spreads to provide precise chromosomal location of the Tether-1 receptor, Tether-1C receptor, or rδNt/Ct receptor gene, as described in Verma et al, *Human Chromosomes: A Manual of basic Techniques*, Pergamon Press, New York (1988); and (3) Northern Blot analysis for detecting Tether-1 receptor, Tether-1C receptor, or rδNt/Ct receptor mRNA expression in specific tissues.

Preferred, however, are nucleic acid molecules having sequences at least 95%, 96%, 97%, 98% or 99% identical to the nucleic acid sequence shown in SEQ ID NO:36, SEQ ID NO:38 and SEQ ID NO:40 or to the nucleic acid sequence of the deposited cDNA which do, in fact, encode a polypeptide having Tether-1 receptor, Tether-1C receptor, or rδNt/Ct receptor activity. By "a polypeptide having Tether-1 receptor, Tether-1C receptor, or rδNt/Ct receptor receptor activity" is intended polypeptides exhibiting activity similar, but not necessarily identical, to an activity of the Tether-1 receptor, Tether-1C receptor, or rδNt/Ct receptor of the invention, as measured in a particular biological assay. For example, Tether-1 receptor, Tether-1C receptor, or rδNt/Ct receptor activity can be measured using competition binding experiments of labeled PTH or PTHrP to cells expressing the candidate Tether-1 receptor, Tether-1C receptor, or rδNt/Ct receptor polypeptide as described herein.

Any cell line expressing the Tether-1 receptor, Tether-1C receptor, or rδNt/Ct receptor, or variants thereof, may be used to assay ligand binding and second messenger activation as described herein. Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence of the deposited cDNAs or the nucleic acid sequence shown in SEQ ID NO:36, SEQ ID NO:38 or SEQ ID NO:40 will encode a polypeptide "having Tether-1 receptor, Tether-1C receptor, or rδNt/Ct receptor activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Tether-1 receptor, Tether-1C receptor, or rδNt/Ct receptor protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

b) Vectors and Host Cells

The present invention also relates to vectors which include the isolated DNA molecules of the present invention, host cells which are genetically engineered with the recombinant vectors, and the production of Tether-1 receptor, Tether-1C receptor, or rδNt/Ct receptor polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The Tether-1 receptor, Tether-1C receptor, or rδNt/Ct receptor can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

c) Tether-1 receptor, Tether-1C receptor, and rδNt/Ct receptor Polypeptides and Fragments The invention further provides an isolated Tether-1 receptor, Tether-1C receptor, and rδNt/Ct receptor polypeptide having the amino acid sequence encoded by the deposited cDNAs, or the amino acid sequence in SEQ ID NO:37, SEQ ID NO:39 and SEQ ID NO:41 or a peptide or polypeptide comprising a portion of the above polypeptides.

It will be recognized in the art that some amino acid sequences of the Tether-1 receptor, Tether-1C receptor, and rδNt/Ct receptor can be varied without significant effect of the structure or function of the protein. If such differences in sequence are contemplated, it should be remembered that there will be critical areas on the protein which determine activity. Thus, the invention further includes variations of the Tether-1 receptor, Tether-1C receptor, and rδNt/Ct receptor which show substantial Tether-1 receptor, Tether-1C receptor, or rδNt/Ct receptor activity or which include regions of Tether-1 receptor, Tether-1C receptor, or rδNt/Ct receptor protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:37, SEQ ID NO:39 and SEQ ID NO:41 or that encoded by the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the Tether-1 receptor, Tether-1C receptor, and rδNt/Ct receptor protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., Nature 361:266–268 (1993) describes certain mutations resulting in selective binding of TNF-α to only one of the two known types of TNF receptors. Thus, the Tether-1 receptor, Tether-1C receptor, and rδNt/Ct receptor of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the Tether-1 receptor, Tether-1C receptor, and rδNt/Ct receptor protein of the present invention that are essential for function can be identified by methods known in the art, such as site-directed mutagenesis or alanine-scanning mutagenesis (Cunningham and Wells, Science 244: 1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallization, nuclear magnetic resonance or photo affinity labeling (Smith et al., J Mol. Biol. 224:899–904 (1992) and de Vos et at Science 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention.

Also intended as an "isolated polypeptide" are polypeptides that have been purified, partially or substantially, from a recombinant host cell. For example, a recombinantly produced version of the antimicrobial peptide polypeptide can be substantially purified by the one-step method described in Smith and Johnson, Gene 67:31–40 (1988).

The polypeptides of the present invention are preferably provided in an isolated form, and preferably are substantially purified. A recombinantly produced version of the Tether-1 receptor, Tether-1C receptor, or rδNt/Ct receptor can be substantially purified by the one-step method described in Smith and Johnson, Gene 67:31–40 (1988).

The polypeptides of the present invention also include the polypeptide encoded by the deposited Tether-1 receptor, Tether-1C receptor, and rδNt/Ct receptor cDNA including the leader, the polypeptide encoded by the deposited the cDNA minus the leader (i.e., the mature protein), the polypeptide of SEQ ID NO:37, SEQ ID NO:39 and SEQ ID NO:41 including the leader, the polypeptide of SEQ ID NO:37, SEQ ID NO:39 and SEQ ID NO:41 minus the leader, the extracellular domain, the transmembrane domain, a polypeptide comprising amino acids about 1 to about 435 in SEQ ID NO:37, SEQ ID NO:39 and SEQ ID NO:41, and a polypeptide comprising amino acids about 2 to about 435 in SEQ ID NO:37, SEQ ID NO:39 and SEQ ID NO:41, as well as polypeptides which are at least 95% identical, still more preferably at least 96%, 97%, 98% or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a Tether-1 receptor, Tether-1C receptor, or rδNt/Ct receptor polypeptide is intended that the amino acid sequence of the polypeptide is identical to the reference sequence except that the polypeptide sequence may include up to five amino acid alterations per each 100 amino acids of the reference amino acid of the Tether-1 receptor, Tether-1C receptor, or rδNt/Ct receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:37, SEQ ID NO:39 and SEQ ID NO:41 to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

7. PTH Agonist and Antagonist Screening Methods Utilizing Tethered Ligand/Receptor Molecules Properties of the tethered ligand/receptor chimeric molecules of the invention make them particularly useful in screening for agonists and antagonists of PTH receptor activity. Screening methods are well known in the art and have been described fully herein for the purposes of identifying novel PTH functional domain conjugate peptides with agonistic and antagonistic PTH receptor properties. Such screening methods measure the effectiveness of a candidate agonist or antagonist by examining the effect on cAMP production or by examining binding to the receptor. Cells utilized in a screening assay, e.g., COS cells, may express the novel receptor of the invention either transiently or permanently. Knowledge regarding the establishment and maintenance of cell lines for this purpose is well known in the art. Candidate agonists and antagonists may be peptide variants of PTH or may constitute structurally distinct molecules, e.g., a mimetic.

Having now fully described the invention, the same will be more readily understood by reference to specific examples which are provided by way of illustration, and are not intended to be limiting of the invention, unless herein specified.

EXAMPLE 1

Construction of PTH Functional Domain Conjugate Peptides

PTH functional conjugate peptides may be constructed using well known methods in the art of molecular biology. The inventors constructed the ligand amino-terminal fragment used herein, PTH(1–9), based upon other studies related to the first 14 amino acids of native human PTH. To optimize activity of this fragment, the inventors replaced the serine at position one by alanine; a substitution which corresponds to the amino acid found at position 1 in rat and bovine PTH, as well as in all PTHrP molecules reported so far (human, bovine, dog, rat, mouse, chicken). This change results in a measurable increase in bioactivity over the background level of bioactivity of the native PTH(1–14) peptide. The C-terminal residue of this new peptide, herein called [Ala$^1$] PTH(1–14), is amidated. The amino-terminal functional domain of PTH(1–9) is based on this sequence. The carboxy-terminal functional domain of PTH(15–31) (Leu Asn Ser Met Glu Arg Val Glu Trp Leu Arg Lys Lys Leu Gin Asp Val) (SEQ ID NO:2) is detailed herein, as well as other variations used in the construction of the peptides. Peptides were created synthetically following procedures well known in the art. Alternatively, the peptides may be created via recombinant DNA techniques by reverse translation. Depending on the organism being used, co don usage charts are helpful in determining the appropriate code. For an example see FIG. 8, wherein the DNA and protein sequences of PG5, PG7 and PG9 are detailed.

EXAMPLE 2

Accumulation of cAMP in Cells Exposed to PTH Functional Domain Conjugate Peptides In order to screen for agonist activity, functional domain conjugate peptides of the invention were utilized in in vitro assays designed to measure cellular response via cAMP accumulation. Intracellular cAMP accumulation is measured as described previously (Abou-Samra et al., *J. Biol. Chem.* 262:1129, 1986).

Cells grown in 24-well plates are rinsed with culture medium containing 0.1% BSA and 2 mM IBMX. The cells are then incubated with an S-(L)$_n$-B compound or derivatives thereof for 60 min. at 21° C. The supernatant is removed and the cells immediately frozen by placing the whole plate in dry ice powder. Intracellular cAMP is extracted by thawing the cells in 1 ml of 50 mM HCl and analyzed by a specific radioimmunoassay using an anti-cAMP antibody (e.g., Sigma, St. Louis, Mo.). A cAMP analog (2'-O-monosuccinyl-adenosine 3',5'-cyclic monophosphate tyrosyl methyl ester, obtained from Sigma) which is used a tracer for cAMP is iodinated by the chloramine T method. Free iodine is removed by adsorbing the iodinated cAMP analog onto a C18 Sep-pak cartridge (Waters, Milford, Mass.). After washing with dH$_2$0, the iodinated cAMP analog is eluted from the Sep-pak Cartridge with 40% acetonitrile (ACN) and 0.1% trifluoroacetic acid (TFA). The iodinated cAMP analog is lyophilized, reconstituted in 1 ml 0.1% TFA, and injected into a C18 reverse phase HPLC column (Waters). The column is equilibrated with 10% ACN in 0.1% TFA, and eluted with gradient of 10–30% ACN in 0.1% TFA. This allows separation of the mono-iodinated cAMP analog from the non-iodinated cAMP analog. The tracer is stable for up to 4 months when stored at –20° C. The standard used for the assay, adenosine 3':5'-cyclic monophosphate, may be purchased from Sigma. Samples (1–10 821 of HCl extracts) or standards (0.04–100 fmol/tube) are diluted in 50 mM Na-acetate (pH 5.5), and acetylated with 10 µl of mixture of triethylamine and acetic anhydride (2:1 vol:vol). After acetylation, cAMP antiserum (100 µl) is added from a stock solution (1:4000) made in PBS (pH 7.4), 5 mM EDTA and 1% normal rabbit serum. The tracer is diluted in PBS (pH 7.4) with 0.1% BSA, and added (20,000 cpm/tube). The assay is incubated at 4° C. overnight. The bound tracer is precipitated by adding 100 µl of goat anti-rabbit antiserum (1:20 in PBS) and 1 ml of 7% polyethyleneglycol (MW 5000–6000), centrifuging at 2000 rpm for 30 min. at 4° C. The supernatant is removed and the bound radioactivity is counted in a gamma-counter (Micromedic). To compute the cAMP data, logit calculations are performed in Excel spreadsheets. Typically, the assay sensitivity is 0.1 fmol/tube, and the standard concentration that displaces 50% of tracer is 5 fmol/tube.

Figure 4A:
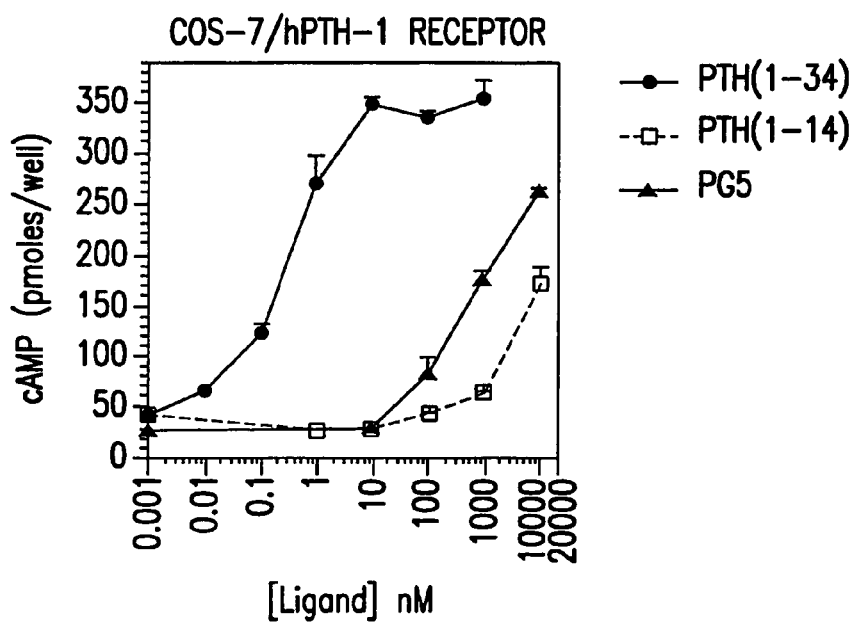
FIG. 4. cAMP dose response curves of short amino-terminal PTH analogs in COS cells transfected with the human PTH-1 receptor (COS7/hPTH-1 cells). COS cells in 24 plates were treated with the indicated peptides for 60 mins at 21° C., and then intracellular cAMP levels were measured. All PTH peptides shown are based on the rat PTH sequence and are carboxy-terminally amidated. 4A, 4B and 4C represent separate experiments.
Figure 4B:
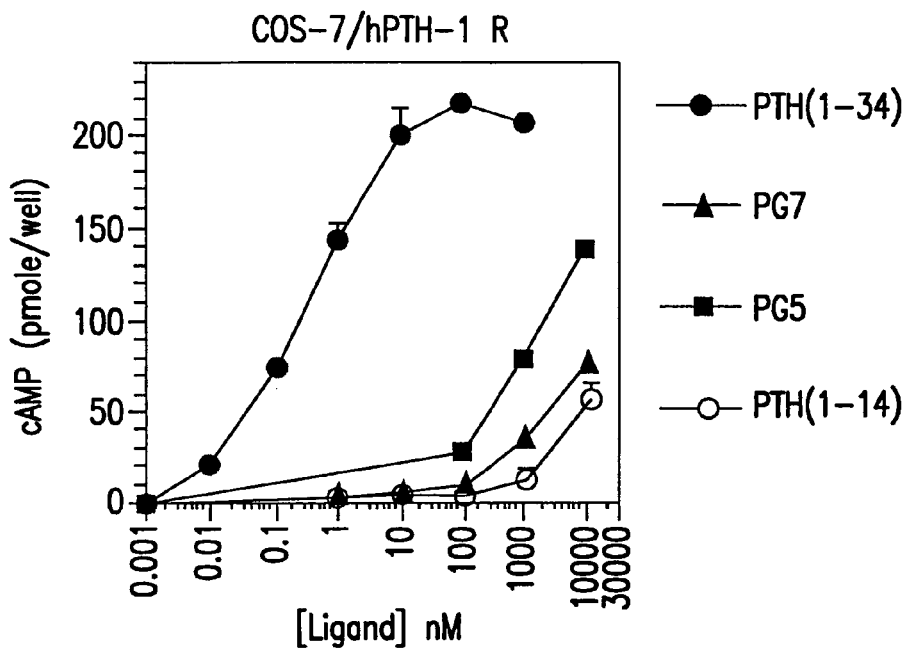
Figure 4C:
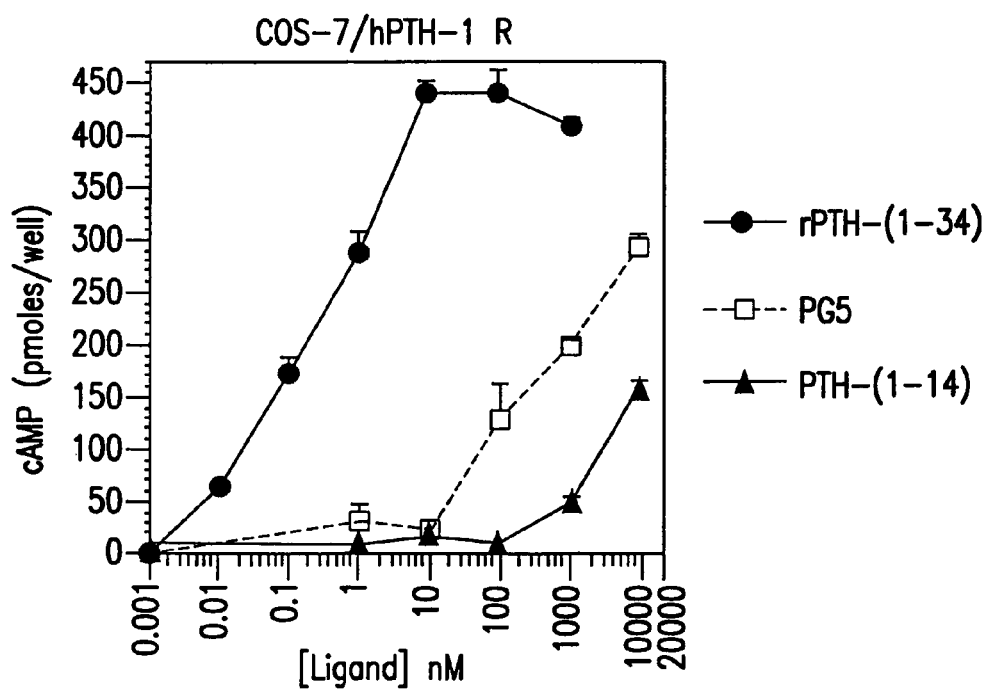

Results of cAMP accumulation experiments are presented in FIGS. 3 and 4. FIG. 3 presents data for the total accumulation of cAMP, while FIG. 4 presents a PTH peptide dose response curve for cAMP accumulation. Importantly, the PTH functional domain peptides PG5, PG7 and PG9 all demonstrate increased levels of cAMP accumulation as compared to basal levels in un-stimulated cells.

EXAMPLE 3

Alanine Scans of PTH(1–14) and PTH(17–31)

Figure 5:
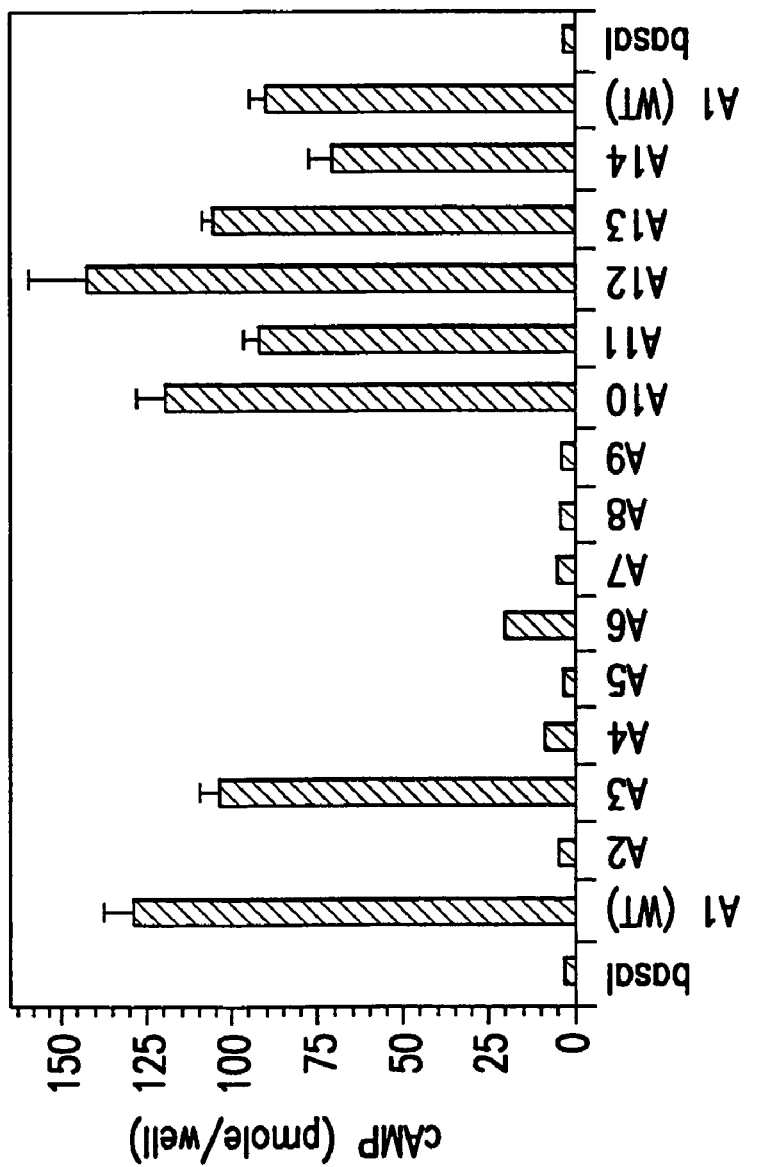
FIG. 5. Alanine-scan of PTH(1–14). Shown are the bioactivities of 14 different PTH(1–14) derivatives, each having a different amino acid of the native sequence (SEQ ID. NO:73; shown at bottom of figure) replaced by alanine. Peptides were chemically synthesized, purified and tested for ability to stimulate cAMP formation in COS-7 cells expressing the cloned human PTH-1 receptor. Pepdites were tested in duplicate (± s.e.m.) At a dose of 67 μM. As a control, untreated cells, indicated by basal, were measured. The PTH(1–14) containing alanine at position 1 was used as the wild-type reference. Cells were stimulated for 30 minutes at 21° C. This figure provides information relevant to bioactivities of amino acid residues in the PTH(1–9) peptide used in the invention.

In order to determine the bioactivity of each amino acid residue in amino-terminal PTH(1–9) signaling peptide and carboxy-terminal PTH(17–31) binding peptide, alanine was substituted for each individual amino acid residue of the two functional domain peptides. The synthesized peptides were used to determine bio activity of the native amino acid residue by either by cAMP accumulation or competitive binding as described herein. Results for PTH(1–9) are presented in FIG. 5, the alanine scan of PTH(1–14). Results for PTH(17–31) are presented in FIG. 6. The results are useful for the design of agonists and antagonists of PTH receptor function and may be used in the construction of S-(L)$_n$-B peptides of the invention.

EXAMPLE 4

Construction of the Novel Tether Receptors

The novel receptors of the invention were constructed using standard techniques in the art of molecular biology. Tether-1 has a deletion of PTH-1 receptor amino terminal sequence; residue 24 and 181. Residues 26–181 indicate the endpoints of the deletion in rδNt. Based on the predicted signal peptide cleavage site between Ala$^{22}$ and Tyr23, residues 23–25 in rδNt are joined to residue 182. Tether-1C is identical to Tether 1 except that a stop codon has been introduced at residue 481. The rδNt/Ct receptor is constructed from PTH-1 with both the 26–181 deletion and the 481 stop codon; It lacks both the extracellular amino terminal ligand binding domain and the intracellular carboxy-terminal domain of the PTH receptor.

Depicted in FIG. 11 is the chemically synthesized oligonucleotide (oligo) (#E16631 A1) that was used to construct the chimeric rat PTH-1 receptor, rTether-1, which contains at its N-terminus residues (1–9) of rat PTH (A-V-S-E-I-Q-L-M-H-) (SEQ ID NO: 74) fused to Glu-182 of the receptor via a tetraglycine linker. The oligo thus encodes the rPTH (1–9) ligand sequence and four Gly residues in its central portion, and rPTH receptor residues as flanking portions. Also shown is the control oligo (E16853A1) that is similar to E16631A1 but in place of rPTH(1–9) there is the amino acid sequence (P-Y-D-V-P-D-Y-A-) (SEQ ID) NO: 71) corresponding to the HA epitope tag; this will yield a receptor construct that we described previously (Luck et al., 1999 Mol. Endo, 13; 670–680).

These oligos were used in the conventional site-directed mutagenesis protocol described by Kunkel (1985, Proc. Natl. Acad. Sci. USA 82;488–492). In brief, the single-stranded oligo was annealed to uracil-containing single-stranded plasmid DNA encoding the rde1NT PTH-1 receptor (described in Luck et al., 1999 Mol. Endo, 13; 670–680), the heteroduplex was subjected to complete second strand synthesis using T7 DNA polymerase, and the reaction products were used to transform E. coli by the electroporation method. Plasmid DNAs from the resulting from the antibiotic resistant colonies were isolated, verified for correct DNA sequence, and then used for subsequent transfection of COS-7 cells and functional assays.

Figure 19B:
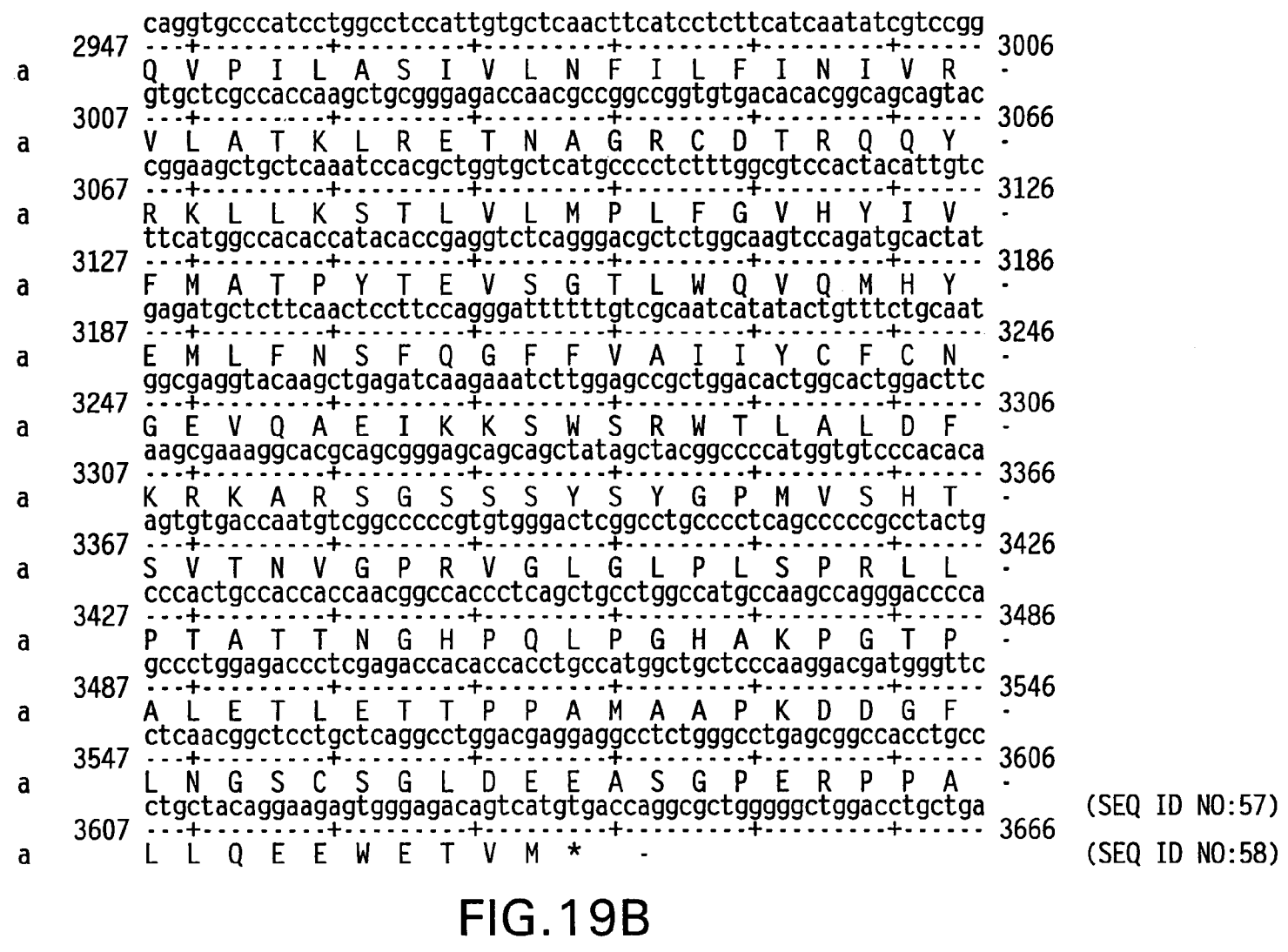

Nucleic acid and amino acid sequences are show in FIGS. 17, 18 and 19 for hTether-1, hde1NT and hTether-R11, respectively.

EXAMPLE 5

Bioactivity of the Tether-1 Receptor cAMP accumulation was used to determine the activity of the Tether-1 receptor. A positive control receptor was constructed by the addition of the HA antigen to the amino-terminus of the native human PTH-1 receptor; the purpose of this control is to test whether the addition of a heterologous sequence to the amino-terminus of the PTH-1 receptor results in anomalous activation of the receptor and/or to determine that the receptor is properly incorporated into the cell membrane via antibody recognition of the HA antigen. The negative control utilized was the rδNt receptor (described in U.S. Patent Application No. 60/105,530). This receptor is a PTH-1 deletion mutant that lacks the extracellular amino-terminus domain of the PTH-1 receptor.

EXAMPLE 6

Autoactivation of PTH-1 Receptors Containing a Tethered Ligand

The analysis of how peptide hormones interact with membrane-bound receptors is obfuscated by the degrees of freedom inherent in such bimolecular systems involving large proteins of uncertain three-dimensional structure. Human parathyroid hormone (hPTH) is an 84 amino acid that plays the vital role of maintaining blood calcium concentrations to within a narrow viable range (Kronenberg, H., et al., in *Genetics of Endocrine and Metabolic Disorders*, Thakker, R., ed., Chapman & Hall, London, U.K. (1997), pp. 389–420). The hormone also has potent anabolic effects on bone (Dempster, D. W., et al., *Endocr. Rev.* 14:690–709 (1993); and Dempster, D. W., et al., *Endocr. Rev.* 15:261 (1994)). These actions are mediated by the PTH-1 receptor, a class B G protein-coupled receptor (Juppner, H., et al., *Science* 254:1024–1026 (1991). Structure-activity analysis of PTH peptides has shown that the (1–34) fragment is sufficent for full biological activity, and that within this peptide, the N-terminal residues are most critical for receptor activation, and that the C-terminal residues contribute the majority of receptor binding energy (Tregear, G. W., et al., *Endocrinol*, 93:1349–1353 (1973); Nussbaum, S. R., et al., *J. Biol. Chem.* 255:10183–10187 (1980)).

Receptor mutagenesis and photochemical crosslinking approaches have suggested that residues within (15–3 4) of PTH interact with the relatively large (~170 amino acids) amino-terminal extracellular domain of the PTH receptor, and that the N-terminal residues of PTH interact with the seven transmembrane domains and extracellular loops (Bergwitz, C., et al., *J. Biol. Chem.* 272:28861–28868 (1997); Lee. C., et al., *Mol. Endo.* 9:1269–1278 (1995); Bissello, A., et al., *J. Biol. Chem.* 273:22498–22505 (1998)). In support of the latter component of this hypothesis, it was recently shown that a peptide as small as PTH(1–14) could stimulate cAMP formation with both the wildtype PTH receptor and a truncated PTH receptor that lacked most of the N-terminal domain (Luck, M., et al., *Molec. Endocrinol*, 13:670–680 (1999)). The potency of PTH(1–14) was low with both the intact and truncated receptor (EC$_{50}$=ca. 100 μM); in contrast, while PTH(1–34) was a potent agonist with the wildtype receptor (EC$_{50}$ ca. 3 nM 4), its potency was severly diminished with the truncated receptor. Both of these results are consistent with the notion that the interactions between the N-terminal domain of the receptor and the C-terminal domain of PTH(1–34) are important in stabilizing the ligand/receptor complex. An alanine-scanning anlaysis performed on PTH(1–14) revealed that residues (1–9), excluding Ser$^3$, were critical for interacting with the hepta-helical and extracellular loop region of the receptor (Luck, M., et al., *Molec. Endocrinol* 13:670–680 (1999)).

Based on the above results, the possibility was considered that the N-terminal (1–9) residues of PTH would be sufficient for receptor activation if they were restrained to within the region of the receptor containing the seven transmembrane domains and extracellular loops. As described herein, it has been shown that this can be accomplished by tethering the N-terminal residues of PTH directly to a truncated receptor lacking the N-terminal extracellular domain; the resulting tethered ligand/receptor constructs are active and exhibit a similar, but not identical, mutational profile as seen previously with PTH(1–14) and PTH(1–34). This system provides a novel approach for analyzing PTH residues involved in receptor signaling without having to generate ligands with high binding affinity.

Material and Methods

Peptides: The peptide [Ala$^{1,3,10,12}$,Arg$^{11}$, Tyr$_{34}$]hPTH (1–34)NH$_2$ {Q-PTH(1–34)} was prepared on an Applied Biosystems model 431A peptide synthesizer using N-(9-fluorenyl)methoxycarbonyl (Fmoc) main-chain protection and TFA-mediated cleavage/deprotection (MGH Biopolymer Synthesis Facility, Boston, Mass.). The peptide was reconstituted in 10 mM acetic acid, and stored at −80° C. The purity, identity, and stock concentration of Q-PTH (1–34) was secured by analytical HPLC, MALDI mass spectrometry and amino acid analysis.

Cell Culture: COS-7 cells were cultured at 37° C. in T-75 flasks (75 mm$^2$ in Dulbecco's modified Eagle's medium (DMEM) supplemented with fetal bovine serum (10%), penicillin G (20 units/ml), streptomycin sulfate (20 µg/ml) and amphotericin B (0.05 µg/ml) in a humidified atmosphere containing 5% $CO_2$. Cells were sub-cultured in 24-well plates and, when confluent, were treated with fresh media and shifted to 33° C. for 12 to 24 h prior to the assay (Bergwitz, C., et al., *J. Biol. Chem.* 272:28861–28868 (1997); Abell, A., et al., *J. Biol. Chem.* 271:4518–4527 (1996)).

PTH Receptor mutagenesis and COS-7 cell expression: The pcDNA-1-based plasmid encoding the intact HPTH-1 receptor (HK-WT in reference (Schipani, E., et al., *Endocrinol.* 132:2157–2165 (1993)) and herein called hP1R-WT) was used for studies in COS-7 cells. The truncated human PTH-1 receptor (hP1R-de1Nt) (FIG. 18) was constructed from the HK-WT plasmid by oligonucleotide-directed mutagenesis (Kunkel, T. A., *Proc. Natl. Acad. Sci. USA* 82:488–492 (1985)). This mutant receptor is deleted for residues 24 to 181 and, assuming that signal peptidase cleavage occurs between Ala$^{22}$ and Tyr$^{23}$ (Nielsen, H., et al., *Protein Engineering* 10:1–6 (1997)), is predicted to have Tyr$^{23}$ as the N-terminal residue joined directly to Glu$^{182}$ located at or near the boundary of the first transmembrane domain. A similarly truncated rat PTH receptor was described by us previously (Luck, M., et al., *Molec. Endocrinol.* 13:670–680 (1999)). The tethered human PTH-1 receptor [hP1R-Tether(1–9)] (hTether-1 in FIG. 17) is based on the hP1R-de1NT construct, and has PTH(1–9) and a four glycine spacer (AVSEIQLMHGGGG) (SEQ ID NO: 72) inserted between residues 23 and 182. Assuming that signal peptidase cleavage occurs between Ala$^{22}$ and Tyr$^{23}$, hP1R-Tether(1–9) is predicted to have Tyr$^{23}$ as the N-terminal residue joined directly to Ala of the ligand. Analogs of hP1R-Tether(1–9) were made in a similar fashion. Transient transfections of COS-7 cells were performed using DEAE-dextran and 200 ng of cesium chloride-purified plasmid DNA per well of a 24-well plate, as described previously (Bergwitz, C., et al., *J. Biol. Chem.* 272:28861–28868 (1997)).

cAMP Stimulation: Stimulation of cells with peptide analogs was performed in 24-well plates. Cells were rinsed with 0.5 mL of binding buffer (50 mM Tris-HCl, 100 mM NaCl, 5 mM KCl, 2 mM $CaCl_2$, 5% heat-inactivated horse serum, 0.5% fetal bovine serum, adjusted to pH 7.7 with HCl) and treated with 200 µL of cAMP assay buffer (Dulbecco's modified Eagle's medium containing 2 mM 3-isobutyl-1-methylxanthine, 1 mg/mL bovine serum albumin, 35 mM Hepes-NaOH, pH 7.4) and 100 µL of binding buffer containing varying amounts of peptide analog (final volume=300 µL). The medium was removed after incubation for 1 h at room temperature, and the cells were frozen (−80° C.), lysed with 0.5 mL 50 mM HCl, and refrozen (−80° C.). The cAMP content of the diluted lysate was determined by radioimmunoassay.

Data Calculation: Calculations were performed using Microsoft Excel. The statistical significance between two data sets was determined using a one-tailed Student's t-test assuming unequal variances for the two sets.

Results

The study began with the construction of the targeted tethered ligand/receptor constructs, which utilized a previously reported de1NT receptor as a point of departure (Luck, M., et al., *Molec. Endocrinol.* 13:670–680 (1999)). This mutant receptor lacks residues 24–181 of the extracellular N-terminal ligand-binding domain, and is predicted to have Tyr$^{23}$ as the N-terminal residue joined directly to Glu$^{182}$ following signal peptidase cleavage. In order to construct a tethered ligand/receptor construct (hTether), the following 13 amino acid sequence was inserted between Tyr$^{23}$ and Glu$^{182}$: Ala-Val-Ser-Glu-Ile-Gln-Leu-Met-His-(Gly)$_4$ (SEQ ID NO: 72). Thus, after signal peptidase cleavage, it is predicted that hP1R-Tether(1–9) should contain (C-term to N-term) the intracellular C-terminal domain, the seven transmembrane helices (and accompanying loops), a short glycine spacer and [Tyr$^{-1}$]-rPTH(1–9). Other tethered ligand/receptor constructs were made in the same fashion, wherein only the sequence corresponding to rPTH(1–9) was expanded in the C-terminal direction by one or two amino acids as in hP1R-[R(1–11) (FIG. 19).

Figure 12A:
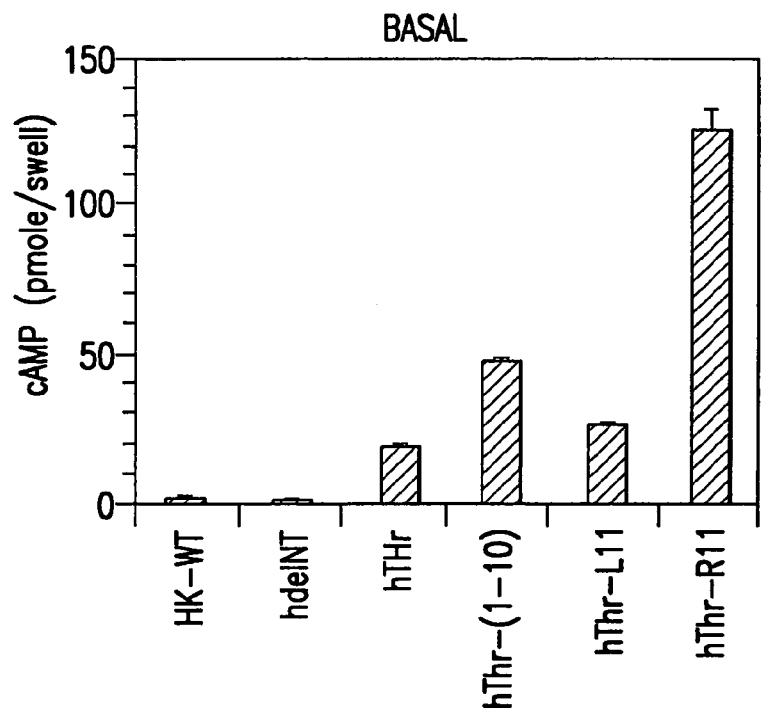
FIG. 12A–12B. Characterization of the signaling properties of hP1R-Tether(1–9) and several of its analogs in transiently transfected COS-7 cells.
Figure 12B:
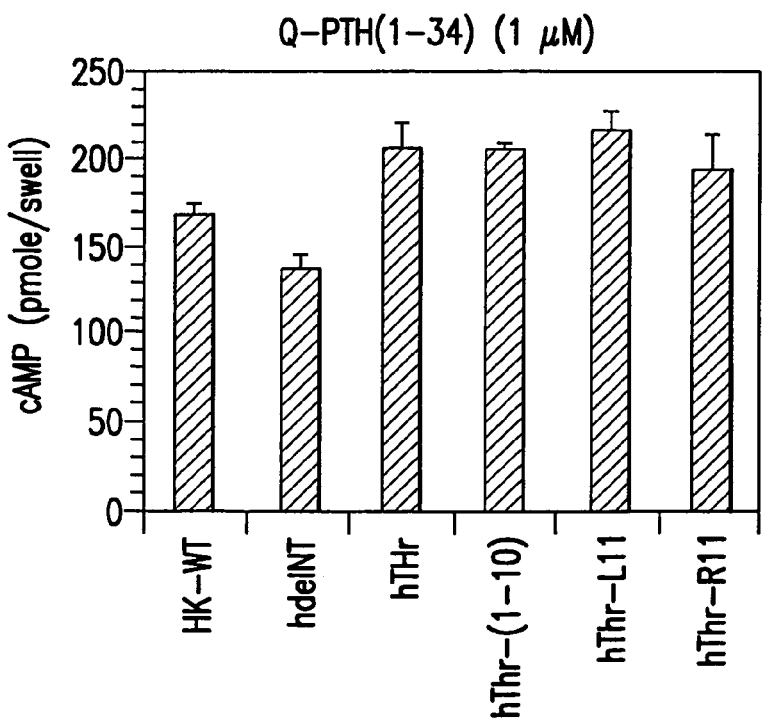
Figure 13:
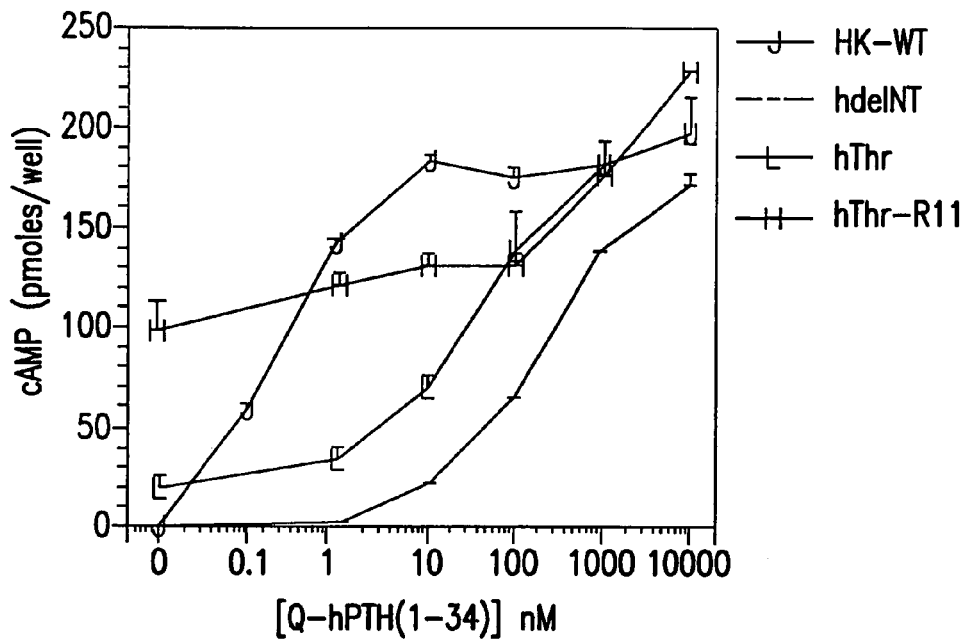
FIG. 13. Dose-response analysis of the truncated receptors hP1R-de1NT, hP1R-Tether(1–9), and hP1R-[$R^{11}$]-Tether(1–11).

Initial characterization of the signaling properties of hP1R-Tether(1–9) and several of its analogs in transiently transfected COS-7 cells is shown in FIGS. 12A–12B. In the absence of any agonist peptide, hP1R-Tether(1–9) shows ca. a 5-fold enhancement in the basal level of cAMP, relative to that seen with hde1NT (FIG. 12A). Extension of the ligand chain (hP1R-Tether(1–10) and (1–11)) resulted in moderate, but significant, improvements in the levels of basal cAMP signaling. This basal signaling could be increased still further by replacement of the leucine at position 11 of hP1R-Tether(1–11) with arginine; we have recently reported that this same modification also dramatically enhances the cAMP potency of short PTH peptides (Shimizu, M., et al., *J. B. M R.* 14: abstract F396 (1999). All of the hP1R-Tether constructs responded to a 1 µM dose of the fully potent analog [Ala$^{1,3,10,12}$, Arg$^{11}$, Tyr$^{34}$]-PTH(1–34)$NH_2$[Q-PTH (1–34)] to a similar extent (FIG. 2B). Dose-response analysis revealed that the truncated receptors hP1r-de1NT, hP1R-Tether(1–9), and hP1R-[R$^{11}$]-Tether(1–11) all exhibited a right-shifted response to Q-PTH(1–34) relative to the intact wildtype receptor; each of these receptors was capable of producing a maximum cAMP response (FIG. 13). The Q-PTH(1–34) dose-response curves for the hP1R-Tether constructs were parallel and left-shifted relative to hP1R-de1NT.

Figure 14:
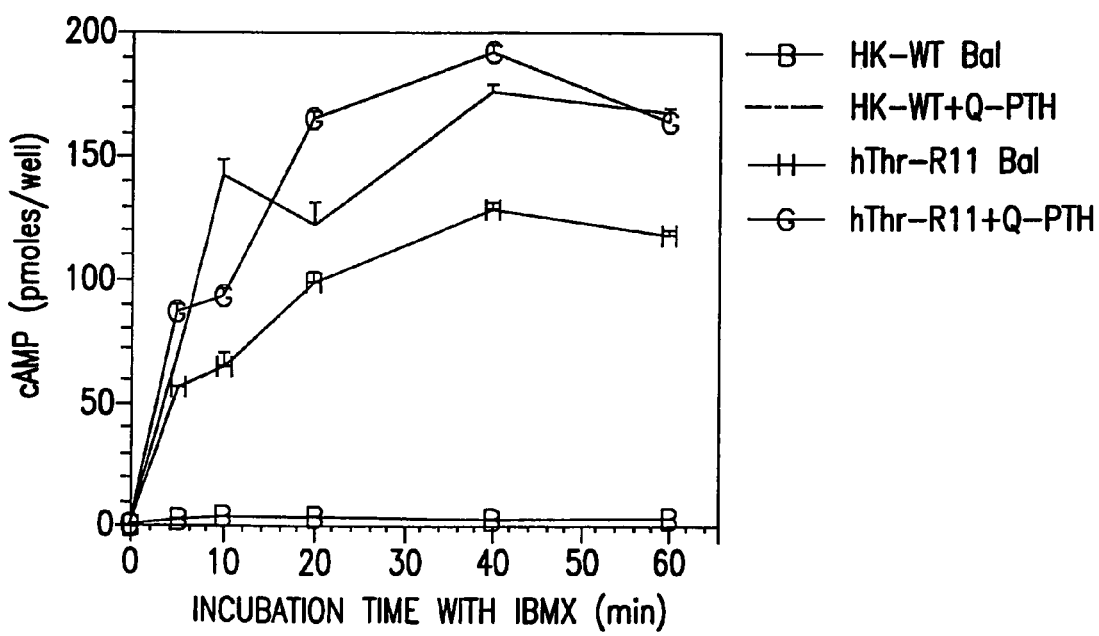
FIG. 14. Time-dependence and DNA-dependence of basal and agonist-induced cAMP signaling for hP1R-[$R^{11}$]-Tether (1–11).
Figure 15:
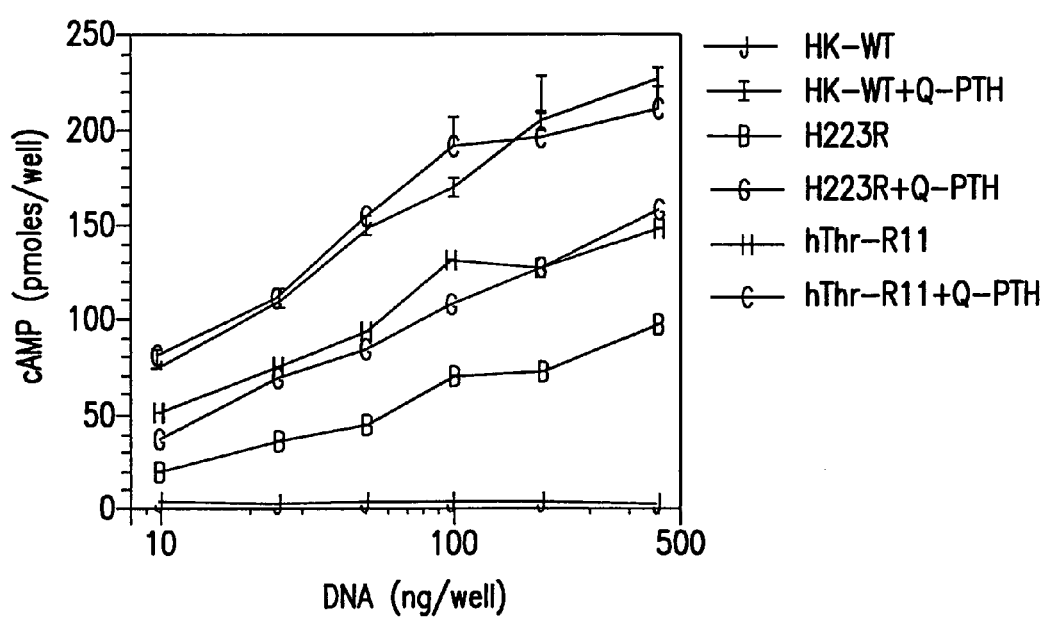
FIG. 15. Basal and agonist-induced signaling of hP1R-[$R^{11}$]-Tether(1–11) is critically dependent on the amount of plasmid DNA used for the transient transfection of the COS-7 cells.

In order to further characterize the constitutive activation of the hP1R-Tether constructs, the time-dependence and DNA-dependence of the basal and agonist-induced cAMP signaling was tested. As shown in FIG. 14, the maximum level of basal cAMP signaling for hP1R-[R$^{11}$]-Tether(1–11) was observed at 40 minutes; this was also the time point at which maximal agonist-induced signaling was observed for both hP1R-WT and hP1R-[R$^{11}$]-Tether(1–11). Both the basal and agonist-induced signaling of hP1R-[R$^{11}$]-Tether (1–11) was critically dependent on the amount of plasmid DNA used for the transient transfection of the COS-7 cells (FIG. 15). This DNA-dependence was parallel to the DNA-dependence observed with the both the basal and agonist-induced signaling of both the hP1R-WT and another constitutively active PTH-1 receptor containing the H223R point mutation at the cytoplasmic end of transmembrane helix 2.

Figure 16A:
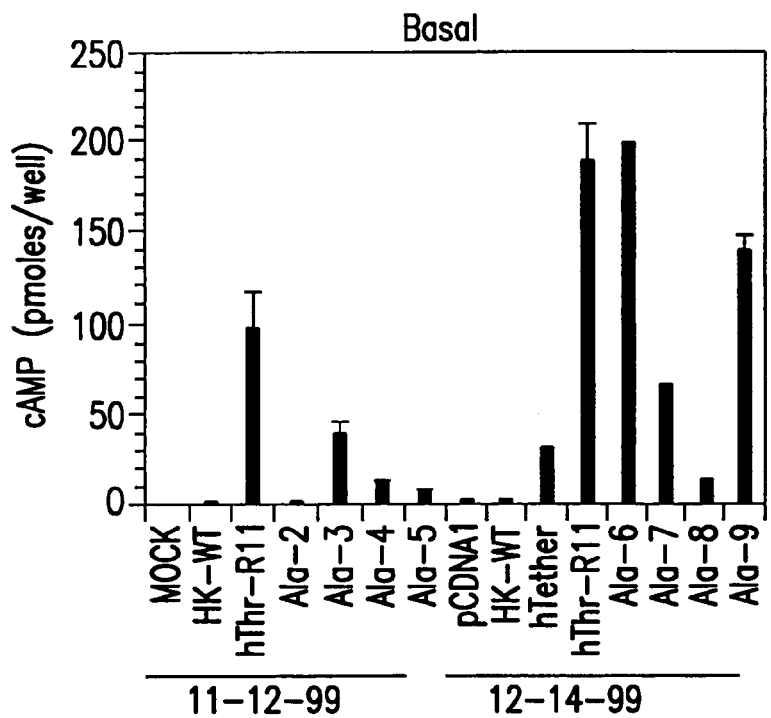
FIG. 16A–16B. Structure-activity profile of PTH peptides and the PTH-portion of hP1R-[$R^{11}$]-Tether(1–11).
Figure 16B:
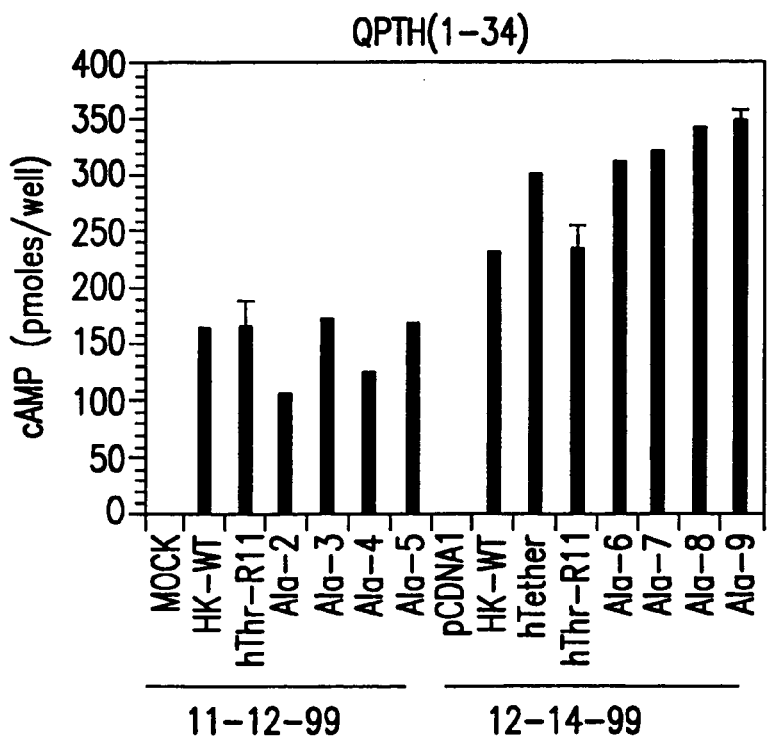

As described above, the level of basal signaling for the hP1R-Tether constructs could be improved by capitalizing on a substitution, Leu→Arg$^{11}$, that we originally discovered in the context of short PTH(1–14) peptides. In order to investigate whether other similarities existed between the structure-activity profile of PTH peptides and the PTH-portion of hP1R-[R$^{11}$]-Tether(1–11), an alanine scan analysis (FIGS. 16A–16B) was performed. As illustrated, replacement of each of the first nine amino acids of the PTH sequence in hP1R-[R$^{11}$]-Tether(1–11) resulted in position-specific effects on the level of basal signaling (FIG. 1 6A), but did not dramatically effect the levels of agonist-induced cAMP signaling (FIG. 1 6B).

Discussion

This study describes a series of novel tethered PTH ligand-receptor conjugates that contain the body of the heptahelical G protein-coupled PTH-1 receptor tethered to the N-terminal "activation core" of the PTH ligand. Each of the tethered receptors in the study exhibited an elevated level of basal cAMP signaling, and hP1R-[R$^{11}$]-Tether(1–11) showed levels of basal signaling that approached the maximum response attained by hP1R-WT when treated with agonist ligand. This ability of a small peptide derived from the activation domain of PTH to stimulate G-protein coupling when tethered to the body of the PTH receptor bears strong similarity to the naturally designed intramolecular mechanism of activation utilized by the protease activated receptors, best represented by the thrombin receptor (Chen, J., et al., *J. Biol. Chem.* 269:16041–16045 (1994)).

For the tethered PTH receptors we observed enhanced responsiveness to exogenous PTH ligands relative to their hP1R-de1NT counterpart. The mechanisms underlying this enhanced responsiveness to exogenous ligands is currently unclear, but it may be that the some proportion of tethered receptor is in an unoccupied yet pre-activated state that is more easily stimulated by PTH(1–34). Such a pre-activated state could, in principle, resemble one of the metastable states observed in the photo-cycle of rhodopsin (Khorana, H. G., *J. Biol. Chem.* 267:1–4 (1992)). In any case, it is clear that enhanced responsivenes to agonist peptides is not a general characteristic of constitutively active PTH receptors (Schipani, E., et al., *J. Clin. Endocrin. Metab.* 84:3052–3057 (1999)). This unique property of the tethered ligand system could yield new insights into the mechanism of PTH receptor activation and potentially offer advantages for screening libraries for novel PTH-1 receptor agonists.

As tethered ligands, the native sequences of PTH(1–10), PTH(1–19), PTH(1–11) were found to be weaker than the tethered PTH(1–11) sequence containing the Leu$^{11}$➔Arg substitution, even though each of these tethered ligands was present at the same equimolar ratio, relative to the concentration of the membrane-embedded portion of the receptor. The level of expression of these receptors was likely to b e comparable, given that each stimulated similar maximum levels of cAMP formation in response to high doses of Q-PTH(1–34). The improved basal signaling of the Arg$^{11}$-containing tethered ligand is consistent with the favorable effect that this same substitution had on the potency of PTH(1–11) and (1–14) analogs. This observation speaks to one of the fundamental questions raised by the tethered ligand-receptor system: do exogenous and tethered ligands utilize the same contact points for activating the receptor?

In order to examine the above question further, an alanine scan analysis of the PTH(1–19) region of hP1R-[R$^{11}$]-Tether(1–11) was performed. The results revealed some differences from the alanine scans performed on PTH(1–14) peptide (Luck, M., et al., *Molec. Endocrinol.* 13:670–680 (1999)) and PTH(1–36) (Gombert, F., et al., in *Peptides: Chemistry, Structure and Biology. Proceedings of the 14th American Peptide Sumposium, June* 18–23, Kamaya, P. and Hodges, R., eds., Mayflower Scientific Limited, Kingswinford, UK (1996), pp. 661–662), but there were compelling similarities to these prior studies. In the case of PTH(1–14), the Ser$^3$➔Ala mutation produced a peptide that was slightly more potent than native PTH(1–14); whereas Ala substitution at any other position in the (2–9) region reduced activity to below detectable levels (position 1 is alanine in the sequence) (Luck, M., et al., *Molec. Endocrinol.* 13:670–680 (1999)). In the case of hP1R-[R$^{11}$]-Tether(1–11), alanine substitution of Ser$^3$ and Leu$^7$ yielded mutants that had ca. 33% of the basal signaling activity seen with the substituted construct, while substitution of Gln$^6$ and His$^9$ yielded mutants that were nearly as active as hP1R-[R$^{11}$]-Tether (1–11). Importantly, alanine substitutions at Val$^2$, Ile$^5$, and Met$^8$ yielded receptors with severely impaired basal signaling. A recent computer modeling effort has predicted that these three residues penetrate the heptahelical core of the receptor (Mierke, D. F. and Pelligrini, M., *Curr. Pharm. Des.* 5:21–36 (1999)). Since all of these mutants responded well to exogenous Q-PTH(1–34), it is unlikely that the effects on signaling are explainable by differences in receptor expression. In order to probe further the hypothesis that the tethered ligand interaction mimics that used by PTH, the influence of certain receptor mutations in the third extracellular loop that are known to effect interactions with the N-terminal residues of exogenous ligands (Lee. C., et al., *Mol. Endo.* 9:1269–1278 (1995)) may be undertaken.

One explanation for the greater mutational tolerance of certain PTH residues in hP1R-[R$^{11}$]-Tether(1–11) (e.g, Gln$^6$, Leu$^7$ and His$^9$), in comparison to similarly substituted PTH (1–14) peptides, is that the high effective molarity of the tethered ligand allows for a discrimination between those residues that principally affect receptor signaling (i.e. Val$^2$, Ile$^5$, and Met$^8$) and those that principally affect ligand binding. The ability to elucidate such a structure/function relationship within the N-terminus of PTH peptides has not been available previously, because the cAMP potency of a given analog is inextricably linked with its affinity for the receptor (Colquhoun, D., *Brit. J. Pharmacol.* 125:924–947 (1998)).

Regardless of whether or not the tethered and exogenous ligands are utilizing the same receptor contacts, the ability to eliminate the need for high affinity binding has significant advantages. The tethered ligand/receptor system described herein likely represents another critical step towards the discovery of a small molecule PTH mimetic.

The tethered receptors (S-L-R's) of the invention may be used in screening assays for PTH agonists. Such agonists might come from libraries of compounds (peptide or non-peptide) that are added exogenously to S-L-Rs expressed in cells or they might come from mutational variations of the S-component of the S-L-R that lead to enhanced autoactivation, in which case the mutant S-component sequence could be synthesized by means known in the art, as a short isolated peptide and this could then be used as a new drug.

Summary of Example 6

Interaction between the N-terminal residues of PTH and the region of the PTH receptor containing the extracellular loops and transmembrane domains is thought to be a critical step in receptor activation. This hypothesis was evaluated by replacing the N-terminal extracellular domain of the HPTH-1 receptor with residues (1–9) of rPTH (AVSEIQLMH) (SEQ ID NO: 74) using a tetraglycine linker between His-9 and Glu-182 at the extracellular end of the first transmembrane domain to yield hP1R-Tether(1–9). Expression of hP1R-Tether(1–9) in COS-7 cells resulted in basal cAMP levels that were 4- to 5-fold higher than those seen in control cells transfected with hP1R-wildtype. Extending the ligand sequence to position-11 and including the activity-enhancing substitution of Leu-11→Arg yielded hP1R-[$R^{11}$]Tether-(1–11) which resulted in a 20-fold increase in basal cAMP signaling, which approached the maximum agonist-stimulated response attained by hP1R-wildtype. Alanine-scan of hP1R-[$R^{11}$]Tether-(1–11) revealed that Val-2, Ile-5 and Met-8 were crucial for auto-activation. Thus, tethered-ligand receptor constructs can be used for analyzing how PTH interacts with its receptor and induces G protein coupling, and should help to constrain models of the overall topological orientation of PTH complexed with its receptor.

The foregoing specification, including the specific embodiments and examples, is intended to be illustrative of the present invention and is not to be taken as limiting. Numerous other variations and modifications can be effected without departing from the true spirit and scope of the present invention. All publications, patents and patent applications cited herein are incorporated by reference in their entirety into the present disclosure.

What is claimed is:

1. An isolated polypeptide of the structure or formula S-(L)$_n$-B wherein:

(a) S is selected from the group consisting of PTH(1–9) (AlaValSerGluIleGlnLeuMetHis) (SEQ ID NO: 1), PTH(1–5) (AlaValSerGluIle) (SEQ ID NO: 4) or PTH (1–11) (AlaValSerGluIleGlnLeuMetHisAsnLeu) (SEQ ID NO: 46);

(b) L is a glycine present n times;

(c) n is 5 to 10; and (d) B is a carboxy terminal binding domain of PTH(1–34) or PTHrP(1–34), wherein said carboxy terminal binding domain binds to a PTH-receptor 1 molecule wherein said polypeptide stimulates intracellular accumulation of cyclic cAMP.

2. The isolated polypeptide of claim 1, wherein L is selected from the group consisting of Gly$_5$, Gly$_7$ and Gly$_9$.

3. The isolated polypeptide of claim 1, wherein B is selected from the group consisting of PTH(15–31) (LeuAsnSerMetGluArgValGluTrpLeuArgLysLysLeuGln-AspVal) (SEQ ID NO:2), PTH(17–31) (SerMetGluArgVal-GluTrpLeuArgLysLysLeuGlnAspVal) (SEQ ID NO:63), PTHrP (15–31) (IleGlnAspLeuArgArgArgPhePheLeuHis-HisLeuIleAlaGluIle) (SEQ ID NO:8), and PTHrP(17–31) (AspLeuArgArgArgPhePheLeuHisHisLeuIleAlaGluIle) (SEQ ID NO:12).

4. An isolated polypeptide selected from the group consisting of: PG5: AlaValSerGluIleGlnLeuMetHisG-lyGlyGlyGlyGlyLeuAsnSer MetGluArgValGluTrpLeuArgLysLysLeuGlnAspVal (SEQ ID NO:3), PG9: AlaVal-SerGluIleGlyGlyGlyGlyGlyGlyGlyGlyLeuAsnSerMet-GluArgValGluTrpLeuArgLysLysLeuGlnAspVal (SEQ ID NO:5), PG7: AlaValSerGluIleGlnLeu MetHisGlyGlyGlyG-lyGlyGlyGlySerMetGluArgValGluTrpLeuArgLysLysLeu-GlnAsp Val (SEQ ID NO:6), PrPG5:AlaValSerGluHisGln-LeuLeuHisGlyGlyGlyGlyGlyIleGlnAspLeuArgArgArg-PhePheLeuHisHisLeuIleAlaGluIle (SEQ ID NO:64), PrPG9: AlaValSerGluHisGlyGlyGlyGlyGlyGlyGlyGlyGly-IleGlnAspLeuArgArgArg PhePheLeuHisHisLeuIleAlaGlu-Ile (SEQ ID NO:65) and PrPG7: AlaValSerGlu HisGln-LeuLeuHisGlyGlyGlyGlyGlyGlyGlyAspLeuArgArgaArg-PhePheLeuHisHisLeuIle AlaGluIle (SEQ ID NO:66).

5. An isolated polypeptide selected from the group consisting of PG5: AlaValSerGluIleGlnLeuMetHisGlyGly-GlyGlyGlyLeuAsnSerMetGluArgValGluTrpLeuArgLys-LysLeuGlnAspVal (SEQ ID NO:3), PG9: AlaValSerGluI-leGlyGlyGlyGlyGlyGlyGlyGlyGlyLeuAsnSerMetGlu-ArgValGluTrpLeuArgLysLysLeuGlnAspVal (SEQ ID NO:5), PG7: AlaValSerGluIleGlnLeu MetHisGlyGlyGly-GlyGlyGlyGlySerMetGluArgValGluTrpLeuArgLysLys-Leu-GlnAsn Val (SEQ ID NO:6).

6. An isolated polypeptide of the structure or formula S-(L)$_n$-B wherein:

(a) S is X Val X Glu X X X X His (SEQ ID NO: 42), wherein X is an amino acid;

(b) L is glycine and n equals 5–10; and (c) B is a carboxy terminal binding domain of PTH(1–34) or PTHrP(1–34), wherein said carboxy terminal binding domain binds to a PTH-receptor 1 molecule, wherein said polypeptide stimulates intracellular accumulation of cyclic cAMP.

7. An isolated polypeptide of the structure or formula S-(L)$_n$-B wherein:

(a) S is Ser Val Ser Glu Ile Gln Leu Met His (SEQ ID NO: 44);

(b) L is 5–10 glycine residues; and (c) B is Leu Asn Ser Met Glu Arg Val Glu Trp Leu Arg Lys Lys Leu Gln Asp Val (SEQ ID NO: 45).

8. An isolated polypeptide encoded by a nucleic acid sequence selected from the group consisting of: SEQ ID NO:14, SEQ ID NO:15 and SEQ ID NO:16.

9. The isolated polypeptide of claim 4, wherein said polypeptide is modified to improve the solubility, absorption, or biological half-life of said polypeptide and wherein said modification is selected from the group consisting of the addition Of $C_{1-12}$ alkyl groups, the addition Of $C_{1-12}$ hydroxyalkyl groups, the addition of acyl groups, and lactam cyclization.

10. The isolated polypeptide of claim 5, wherein said polypeptide is modified to improve the solubility, absorption, or biological half-life of said polypeptide and wherein said modification is selected from the group consisting of the addition Of $C_{1-12}$ alkyl groups, the addition Of $C_{1-12}$ hydroxyalkyl groups, the addition of acyl groups, and lactam cyclization.

11. The isolated polypeptide of claim 1, wherein n is an integer from 5 to 9.

* * * * *

UNITED STATES PATENT AND TRADEMARK OFFICE
CERTIFICATE OF CORRECTION

PATENT NO. : 7,057,012 B1  
APPLICATION NO. : 09/475158  
DATED : June 6, 2006  
INVENTOR(S) : Gardella et al.

Page 1 of 1

It is certified that error appears in the above-identified patent and that said Letters Patent is hereby corrected as shown below:

Column 5, line 7, "Gin" should be replaced with "Gln."
Column 6, line 47, "G protein receptor coupled" should be replaced with "G protein-coupled receptor."
Column 15, line 45, "Gin" should be replaced with "Gln."
Column 15, line 54, "Ag" should be replaced with "Arg."
Column 15, line 56, "Gn" should be replaced with "Gln."

Signed and Sealed this

Fourteenth Day of November, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,057,012 B1 |
| APPLICATION NO. | : 09/475158 |
| DATED | : June 6, 2006 |
| INVENTOR(S) | : Gardella et al. |

It is certified that error appears in the above-identified patent and that said Letters Patent is hereby corrected as shown below:

Column 1, Line 9: after "Statement as to Rights to Inventions Made Under Federally-Sponsored Research and Development" replace "Part of the work performed during development of this invention utilized U.S. Government funds."

with

--This invention was made with Government support under Grant No. DK011794 awarded by the National Institutes of Health.--

Signed and Sealed this

Thirtieth Day of June, 2009

JOHN DOLL
*Acting Director of the United States Patent and Trademark Office*